United States Patent
Esfandyarpour et al.

(10) Patent No.: US 10,544,456 B2
(45) Date of Patent: Jan. 28, 2020

(54) SYSTEMS AND METHODS FOR NUCLEIC ACID SEQUENCING

(71) Applicant: GenapSys, Inc., Redwood City, CA (US)

(72) Inventors: Hesaam Esfandyarpour, Redwood City, CA (US); Kosar Parizi, Redwood City, CA (US); Saurabh Paliwal, Mountain View, CA (US); Seth Stern, Menlo Park, CA (US); Paul Kenney, Sunnyvale, CA (US); Meysam R. Barmi, Menlo Park, CA (US); Ali Nabi, Belmont, CA (US); Hamid Rategh, Cupertino, CA (US)

(73) Assignee: GENAPSYS, INC., Redwood City, CA (US)

( * ) Notice: Subject to any disclaimer, the term of this patent is extended or adjusted under 35 U.S.C. 154(b) by 0 days.

(21) Appl. No.: 15/655,616

(22) Filed: Jul. 20, 2017

(65) Prior Publication Data
US 2018/0100190 A1    Apr. 12, 2018

Related U.S. Application Data

(60) Provisional application No. 62/364,489, filed on Jul. 20, 2016, provisional application No. 62/375,197, filed on Aug. 15, 2016, provisional application No. 62/418,101, filed on Nov. 4, 2016, provisional application No. 62/444,700, filed on Jan. 10, 2017.

(51) Int. Cl.
*C12Q 1/6869* (2018.01)

(52) U.S. Cl.
CPC ................. *C12Q 1/6869* (2013.01)

(58) Field of Classification Search
CPC ..... C12Q 1/6869; C07H 21/04; G01N 33/551
See application file for complete search history.

(56) References Cited

U.S. PATENT DOCUMENTS

| | | | |
|---|---|---|---|
| 2,014,761 A | 9/1935 | Faust | |
| 4,072,576 A | 2/1978 | Arwin et al. | |
| 5,344,545 A | 9/1994 | Tsukada et al. | |
| 5,407,799 A | 4/1995 | Studier et al. | |
| 5,466,348 A | 11/1995 | Holm-Kennedy | |
| 5,602,042 A | 2/1997 | Farber | |
| 5,612,181 A | 3/1997 | Fourmentin-Guilbert | |
| 5,795,782 A | 8/1998 | Church et al. | |
| 5,834,197 A | 11/1998 | Parton | |
| 6,046,097 A | 4/2000 | Hsieh et al. | |
| 6,087,095 A | 7/2000 | Rosenthal et al. | |
| 6,210,891 B1 | 4/2001 | Nyren et al. | |
| 6,327,410 B1 | 12/2001 | Walt et al. | |
| 6,632,655 B1 | 10/2003 | Mehta et al. | |
| 6,833,246 B2 | 12/2004 | Balasubramanian | |
| 6,870,235 B2 | 3/2005 | Abstreiter et al. | |
| 6,953,958 B2 | 10/2005 | Baxter et al. | |
| 7,081,192 B1 | 7/2006 | Wang et al. | |
| 7,095,010 B2 | 8/2006 | Scherer et al. | |
| 7,223,540 B2 | 5/2007 | Pourmand et al. | |
| 7,238,536 B1 | 7/2007 | Schlenoff | |
| 7,242,241 B2 | 7/2007 | Toumazou et al. | |
| 7,270,981 B2 | 9/2007 | Armes et al. | |
| 7,282,370 B2 | 10/2007 | Bridgham et al. | |
| 7,291,496 B2 | 11/2007 | Holm-Kennedy | |
| 7,312,085 B2 | 12/2007 | Chou et al. | |
| 7,317,216 B2 | 1/2008 | Holm-Kennedy | |
| 7,323,305 B2 | 1/2008 | Leamon et al. | |
| 7,361,466 B2 | 4/2008 | Korlach et al. | |
| 7,399,590 B2 | 7/2008 | Piepenburg et al. | |
| 7,435,561 B2 | 10/2008 | Piepenburg et al. | |
| 7,485,428 B2 | 2/2009 | Armes et al. | |
| 7,615,382 B2 | 11/2009 | Wang et al. | |
| 7,645,596 B2 | 1/2010 | Williams et al. | |
| 7,649,358 B2 | 1/2010 | Toumazou et al. | |
| 7,666,598 B2 | 2/2010 | Piepenburg et al. | |
| 7,682,837 B2 | 3/2010 | Jain et al. | |
| 7,686,929 B2 | 3/2010 | Toumazou et al. | |
| 7,692,219 B1 | 4/2010 | Holm-Kennedy | |
| 7,695,907 B2 | 4/2010 | Miyahara et al. | |
| 7,763,427 B2 | 7/2010 | Piepenburg et al. | |
| 7,824,890 B2 | 11/2010 | Hoser et al. | |
| 7,835,871 B2 | 11/2010 | Kain et al. | |
| 7,875,440 B2 | 1/2011 | Williams et al. | |
| 7,888,013 B2 | 2/2011 | Miyahara et al. | |
| 7,932,034 B2 | 4/2011 | Esfandyarpour et al. | |

(Continued)

FOREIGN PATENT DOCUMENTS

CN        1337580 A      2/2002
CN        101120098 A    2/2008

(Continued)

OTHER PUBLICATIONS

Co-pending U.S. Appl. No. 16/033,437, filed Jul. 21, 2018.
Co-pending U.S. Appl. No. 16/105,480, filed Aug. 20, 2018.
Co-pending U.S. Appl. No. 16/115,344, filed Aug. 28, 2018.
Co-pending U.S. Appl. No. 16/137,408, filed Sep. 20, 2018.
U.S. Appl. No. 16/007,969 Notice of Allowance dated Nov. 26, 2018.

(Continued)

*Primary Examiner* — Narayan K Bhat
(74) *Attorney, Agent, or Firm* — Wilson Sonsini Goodrich & Rosati

(57) ABSTRACT

Provided herein are systems and methods for processing and analyzing nucleic acids and other biomolecules. Methods may include processing nucleic acid molecules in an emulsion of droplets. Methods of analyzing nucleic acid molecules may include coupling nucleic acids to a bead or other support. Methods may include analysis of nucleic acid molecules using a redox mediator. In some cases, analysis of the nucleic acid molecule includes determining a nucleotide sequence of the nucleic acid molecule.

10 Claims, 34 Drawing Sheets

(56) References Cited

U.S. PATENT DOCUMENTS

| | | |
|---|---|---|
| 7,948,015 B2 | 5/2011 | Rothberg et al. |
| 8,023,113 B2 | 9/2011 | El Gamal et al. |
| 8,030,000 B2 | 10/2011 | Piepenburg et al. |
| 8,039,817 B2 | 10/2011 | Feng et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,154,093 B2 | 4/2012 | Bradley et al. |
| 8,173,080 B2 | 5/2012 | Lebl et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,274,040 B2 | 9/2012 | Zhong et al. |
| 8,301,394 B2 | 10/2012 | Chen et al. |
| 8,315,817 B2 | 11/2012 | Kain et al. |
| 8,392,126 B2 | 3/2013 | Mann |
| 8,426,134 B2 | 4/2013 | Piepenburg et al. |
| 8,460,875 B2 | 6/2013 | Armes et al. |
| 8,486,625 B2 | 7/2013 | Gunderson et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,649,011 B2 | 2/2014 | Mccaffrey et al. |
| 8,673,560 B2 | 3/2014 | Leamon et al. |
| 8,778,848 B2 | 7/2014 | Lin et al. |
| 8,778,849 B2 | 7/2014 | Bowen et al. |
| 8,865,077 B2 | 10/2014 | Chiou et al. |
| 8,865,078 B2 | 10/2014 | Chiou et al. |
| 8,914,241 B2 | 12/2014 | Kain et al. |
| 8,969,002 B2 | 3/2015 | Esfandyarpour et al. |
| 9,045,796 B2 | 6/2015 | Gunderson et al. |
| 9,063,117 B2 | 6/2015 | Gourley |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,188,594 B2 | 11/2015 | Fahmy et al. |
| 9,274,077 B2 | 3/2016 | Esfandyarpour et al. |
| 9,399,217 B2 | 7/2016 | Oldham et al. |
| 9,434,983 B2 | 9/2016 | Esfandyarpour |
| 9,533,305 B2 | 1/2017 | Esfandyarpour et al. |
| 9,689,835 B2 | 6/2017 | Liu et al. |
| 9,809,852 B2 | 11/2017 | Esfandyarpour et al. |
| 9,822,401 B2 | 11/2017 | Oberstrass et al. |
| 9,926,596 B2 | 3/2018 | Esfandyarpour et al. |
| 9,945,807 B2 | 4/2018 | Baghbani-Parizi et al. |
| 9,990,381 B2 | 6/2018 | Eltoukhy et al. |
| 10,059,982 B2 | 8/2018 | Esfandyarpour et al. |
| 10,093,975 B2 | 10/2018 | Esfandyarpour et al. |
| 10,100,356 B2 | 10/2018 | Esfandyarpour et al. |
| 10,125,393 B2 | 11/2018 | Esfandyarpour et al. |
| 10,260,095 B2 | 4/2019 | Esfandyarpour et al. |
| 10,266,892 B2 | 4/2019 | Esfandyarpour et al. |
| 10,472,674 B2 | 11/2019 | Esfandyarpour et al. |
| 10,494,672 B2 | 12/2019 | Esfandyarpour et al. |
| 2002/0132245 A1 | 9/2002 | Boles et al. |
| 2002/0148739 A2 | 10/2002 | Liamos et al. |
| 2003/0078314 A1 | 4/2003 | Johnson et al. |
| 2003/0209432 A1 | 11/2003 | Choong et al. |
| 2004/0014201 A1 | 1/2004 | Kim et al. |
| 2004/0023253 A1 | 2/2004 | Kunwar et al. |
| 2004/0033492 A1 | 2/2004 | Chen |
| 2004/0136866 A1 | 7/2004 | Pontis et al. |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2005/0084980 A1 | 4/2005 | Koo et al. |
| 2005/0098434 A1 | 5/2005 | Gundel et al. |
| 2005/0123937 A1 | 6/2005 | Thorp et al. |
| 2005/0129526 A1 | 6/2005 | Dukhin et al. |
| 2005/0200648 A1 | 9/2005 | Doak et al. |
| 2005/0218464 A1 | 10/2005 | Holm-Kennedy |
| 2006/0008824 A1 | 1/2006 | Ronaghi et al. |
| 2006/0105373 A1 | 5/2006 | Pourmand et al. |
| 2006/0147955 A1 | 7/2006 | Allawi et al. |
| 2006/0170931 A1 | 8/2006 | Guo et al. |
| 2006/0199193 A1 | 9/2006 | Koo et al. |
| 2006/0222569 A1 | 10/2006 | Barten et al. |
| 2007/0132043 A1 | 6/2007 | Bradley et al. |
| 2007/0184463 A1 | 8/2007 | Molho et al. |
| 2007/0275375 A1 | 11/2007 | Van Eijk et al. |
| 2008/0009420 A1 | 1/2008 | Schroth et al. |
| 2008/0032294 A1 | 2/2008 | Kawarada et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0187915 A1 | 8/2008 | Polonsky et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1 | 12/2008 | Haga et al. |
| 2009/0000957 A1 | 1/2009 | Dubin et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 | 7/2009 | Su et al. |
| 2009/0170724 A1 | 7/2009 | Balasubramanian et al. |
| 2009/0181385 A1 | 7/2009 | Mckernan et al. |
| 2009/0191594 A1 | 7/2009 | Ohashi |
| 2010/0000881 A1 | 1/2010 | Franzen et al. |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0105035 A1 | 4/2010 | Hashsham et al. |
| 2010/0112588 A1 | 5/2010 | Farinas et al. |
| 2010/0137143 A1 | 6/2010 | Rothberg et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander Horn et al. |
| 2011/0008775 A1 | 1/2011 | Gao et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |
| 2011/0195253 A1 | 8/2011 | Hinz et al. |
| 2011/0195459 A1 | 8/2011 | Hinz et al. |
| 2011/0201057 A1 | 8/2011 | Carr et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |

(56) References Cited

U.S. PATENT DOCUMENTS

| | | |
|---|---|---|
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0014837 A1 | 1/2012 | Fehr et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0052489 A1 | 3/2012 | Gordon et al. |
| 2012/0055811 A1 | 3/2012 | Rothberg et al. |
| 2012/0055813 A1 | 3/2012 | Rothberg et al. |
| 2012/0061239 A1 | 3/2012 | Elibol et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0247977 A1 | 10/2012 | Rothberg et al. |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour |
| 2012/0322054 A1 | 12/2012 | Rothberg et al. |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0109577 A1 | 5/2013 | Korlach et al. |
| 2013/0183211 A1 | 7/2013 | Senftleber |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0034497 A1 | 2/2014 | Davis et al. |
| 2014/0099674 A1 | 4/2014 | Piepenburg et al. |
| 2014/0106338 A1 | 4/2014 | Fischer et al. |
| 2014/0235457 A1 | 8/2014 | Esfandyarpour et al. |
| 2014/0272952 A1 | 9/2014 | May et al. |
| 2014/0329699 A1 | 11/2014 | Esfandyarpour |
| 2015/0316502 A1 | 11/2015 | Mohanty et al. |
| 2015/0344943 A1 | 12/2015 | Oberstrass |
| 2015/0368707 A1 | 12/2015 | Esfandyarpour et al. |
| 2015/0376681 A1 | 12/2015 | Gupta et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2016/0340721 A1 | 11/2016 | Esfandyarpour |
| 2017/0065977 A1 | 3/2017 | Esfandyarpour et al. |
| 2017/0073750 A1 | 3/2017 | Esfandyarpour et al. |
| 2017/0088575 A1 | 3/2017 | Ju et al. |
| 2017/0211141 A1 | 7/2017 | Gordon et al. |
| 2019/0177790 A1 | 6/2019 | Esfandyarpour et al. |
| 2019/0177791 A1 | 6/2019 | Esfandyarpour et al. |

FOREIGN PATENT DOCUMENTS

| | | |
|---|---|---|
| CN | 101405083 A | 4/2009 |
| CN | 101848757 A | 9/2010 |
| CN | 101918590 A | 12/2010 |
| CN | 102980922 A | 3/2013 |
| EP | 0676623 A2 | 10/1995 |
| EP | 1333089 A1 | 8/2003 |
| EP | 1499738 B1 | 7/2008 |
| EP | 1992706 A2 | 11/2008 |
| EP | 2290096 A2 | 3/2011 |
| EP | 2336361 A2 | 6/2011 |
| EP | 2428588 A2 | 3/2012 |
| EP | 2287341 B1 | 2/2013 |
| EP | 1759012 B1 | 5/2013 |
| EP | 2660336 A1 | 11/2013 |
| JP | 2006512583 A | 4/2006 |
| JP | 2008525822 A | 7/2008 |
| JP | 2010513869 A | 4/2010 |
| JP | 2010517040 A | 5/2010 |
| JP | 2010517041 A | 5/2010 |
| JP | 2010518401 A | 5/2010 |
| WO | WO-0118246 A1 | 3/2001 |
| WO | WO-0137958 A2 | 5/2001 |
| WO | WO-0142508 A2 | 6/2001 |
| WO | WO-0227909 A2 | 4/2002 |
| WO | WO-02061146 A1 | 8/2002 |
| WO | WO-2004027024 A2 | 4/2004 |
| WO | WO-2004076683 A2 | 9/2004 |
| WO | WO-2005008450 A2 | 1/2005 |
| WO | WO-2005108612 A2 | 11/2005 |
| WO | WO-2005121363 A2 | 12/2005 |
| WO | WO-2006050346 A2 | 5/2006 |
| WO | WO-2007030505 A1 | 3/2007 |
| WO | WO-2007041619 A2 | 4/2007 |
| WO | WO-2007098049 A2 | 8/2007 |
| WO | WO-2008076406 A2 | 6/2008 |
| WO | WO-2008132643 A1 | 11/2008 |
| WO | WO-2009012112 A1 | 1/2009 |
| WO | WO-2009052348 A2 | 4/2009 |
| WO | WO-2009074926 A1 | 6/2009 |
| WO | WO-2009122159 A2 | 10/2009 |
| WO | WO-2009150467 A1 | 12/2009 |
| WO | WO-2010008480 A2 | 1/2010 |
| WO | WO-2010026488 A2 | 3/2010 |
| WO | WO-2010037085 A1 | 4/2010 |
| WO | WO-2010041231 A2 | 4/2010 |
| WO | WO-2010047804 A1 | 4/2010 |
| WO | WO-2010075188 A2 | 7/2010 |
| WO | WO-2010138187 A1 | 12/2010 |
| WO | WO-2010141940 A1 | 12/2010 |
| WO | WO-2011106556 A2 | 9/2011 |
| WO | WO-2012047889 A2 | 4/2012 |
| WO | WO-2012166742 A2 | 12/2012 |
| WO | WO-2013082619 A1 | 6/2013 |
| WO | WO-2013119765 A1 | 8/2013 |
| WO | WO-2013188582 A1 | 12/2013 |
| WO | WO-2014012107 A2 | 1/2014 |
| WO | WO-2014043143 A1 | 3/2014 |
| WO | WO-2014152625 A1 | 9/2014 |
| WO | WO-2015089238 A1 | 6/2015 |
| WO | WO-2015138696 A1 | 9/2015 |
| WO | WO-2015161054 A2 | 10/2015 |
| WO | WO-2018017884 | 1/2018 |
| WO | WO-2019060628 A1 | 3/2019 |

OTHER PUBLICATIONS

U.S. Appl. No. 14/361,902 Office Action dated Oct. 7, 2016.
U.S. Appl. No. 14/859,725 Notice of Allowance dated Sep. 11, 2018.
U.S. Appl. No. 15/360,369 Office Action dated Nov. 29, 2018.
U.S. Appl. No. 16/007,829 Office Action dated Sep. 17, 2018.
U.S. Appl. No. 14/859,725 Notice of Allowance dated Jun. 19, 2018.

(56) References Cited

OTHER PUBLICATIONS

Andreotti, et al. Immunoassay of infectious agents. Biotechniques. Oct. 2003;35(4):850-9.
Bell, et al. Detection of Bacillus anthracis DNA by LightCycler PCR. J Clin Microbiol. Aug. 2002;40(8):2897-902.
Boo, et al. Electrochemical nanoneedle biosensor based on multiwall carbon nanotube. Anal Chem. Jan. 15, 2006;78(2):617-20.
Brouns, et al. Small CRISPR RNAs guide antiviral defense in prokaryotes. Science. Aug. 15, 2008;321(5891):960-4.
Cagnin, et al. Overview of electrochemical DNA biosensors: new approaches to detect the expression of life. Sensors (Basel). 2009;9(4):3122-48. doi: 10.3390/s90403122. Epub Apr. 24, 2009.
Carte, et al., Cas6 is an endoribonuclease that generates guide RNAs for invader defense in prokaryotes. Genes Dev. Dec. 15, 2008;22(24):3489-96.
Cho, et al. Bis-aptazyme sensors for hepatitis C virus replicase and helicase without blank signal. Nucleic Acids Res. Nov. 27, 2005;33(20):e177.
Co-pending U.S. Appl. No. 15/726,193, filed Oct. 5, 2017.
Co-pending U.S. Appl. No. 15/726,217, filed Oct. 5, 2017.
Daniels, et al. Label-Free Impedance Biosensors: Opportunities and Challenges. Electroanalysis. Jun. 2007;19(12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Didion, et al., Invaders: Recognition of Double-Stranded DNA by Using Duplexes Modified with Interstrand Zippers of 2'-O-(Pyren-1-yl)methyl-ribonucleotides. Chembiochem. Sep. 2, 2013;14(13):1534-1538. doi: 10.1002/cbic.201300414. Epub 2013 Aug. 23, 2013.
Dimov, et al. Stand-alone self-powered integrated microfluidic blood analysis system (SIMBAS). Lab Chip. Mar. 7, 2011;11(5):845-50.
Edman, et al. Electric field directed nucleic acid hybridization on microchips. Nucleic Acids Res. Dec. 15, 1997; 25(24): 4907-14.
Ellington, et al. In vitro selection of RNA molecules that bind specific ligands. Nature. Aug. 30, 1990;346(6287):818-22.
Esfandyarpour, et al. 3D modeling of impedance spectroscopy for protein detection in nanoneedle biosensors. Proceedings of the COMSOL Conference 2007, Boston.
Esfandyarpour, et al. 3D Modeling of Impedance Spectroscopy for Protein Detection in Nanoneedle Biosensors. Proceedings of the International COMSOL Conference 2007, Boston, MA, USA, pp. 169-173 (Oct. 4-6, 2007).
Esfandyarpour, et al. A Novel Nanoneedle Biosensor for DNA Sequencing (abstract). Dec. 31, 2008. Available at http://www.nsti.org/Nanotech2008/showabstract.html?absno=1522.
Esfandyarpour, et al. Geometrical Optimization of Pyrophosphate Concentration in Thermosequencing Platform for DNA Sequencing. Proceedings of the COMSOL Conf. 2007, Boston.
European search report and search opinion dated Jan. 5, 2015 for EP Application No. 12792216.9.
European search report and search opinion dated Mar. 12, 2014 for EP Application No. 11831452.5.
European search report and search opinion dated Jul. 13, 2015 for EP Application No. 12852490.7.
European Search Report dated Oct. 11, 2017 for European Patent Application No. EP14869402.9.
Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Gao, et al. Silicon nanowire arrays for label-free detection of DNA. Anal Chem. May 1, 2007;79(9):3291-7. Epub Apr. 4, 2007.
Gardeniers, et al. Silicon micromachined hollow microneedles for transdermal liquid transport. Journal of Microelectromechanical Systems. 2003;12(6):855-862.
Guiducci, et al. A Biosensor for Direct Detection of DNA Sequences Based on Capacitance Measurements. ESSDERC 2002, pp. 479-482.
Haurwitz, et al. Sequence- and structure-specific RNA processing by a CRISPR endonuclease. Science. Sep. 10, 2010;329(5997):1355-8.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
International search report and written opinion dated Aug. 21, 2014 for PCT Application No. PCT/US2014/027544.
International search report and written opinion dated Oct. 26, 2015 for PCT/US2015/026135.
Javanmard, et al. A microfluidic platform for electrical detection of DNA hybridization. Sens Actuators B Chem. May 20, 2011;154(1):22-27. Epub Mar. 30, 2010.
Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Nov. 2009;27(6):3099-3103.
Kaushik, et al. Lack of pain associated with microfabricated microneedles. Anesth Analg. Feb. 2001;92(2):502-4.
Kim, et al. Replication of DNA microarrays prepared by in situ oligonucleotide polymerization and mechanical transfer. Anal Chem. Oct. 1, 2007;79(19):7267-74.
Kitano, et al. Molecular structure of RNA polymerase and its complex with DNA. J Biochem. Jan. 1969;65(1):1-16.
Kunin, et al. Evolutionary conservation of sequence and secondary structures in CRISPR repeats. Genome Biol. 2007;8(4):R61.
Kurosaki, et al. Rapid and simple detection of Ebola virus by reverse transcription-loop-mediated isothermal amplification. J Virol Methods. Apr. 2007;141(1):78-83.
Lee, et al. Ion-sensitive field-effect transistor for biological sensing. Sensors (Basel). 2009;9(9):7111-31. doi: 10.3390/s90907111. Epub Sep. 7, 2009.
Lin, et al. Replication of DNA microarrays from zip code masters. J Am Chem Soc. Mar. 15, 2006;128(10):3268-72.
Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.
Makarova, et al. A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.
Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.
Margulies, et al. Genome sequencing in microfabricated high-density picolitre reactors. Nature. Sep. 15, 2005;437(7057):376-80. Epub Jul. 31, 2005.
Notice of allowance dated Mar. 28, 2016 for U.S. Appl. No. 13/481,858.
Notice of Allowance dated May 12, 2017 for U.S. Appl. No. 14/653,230.
Notice of allowance dated May 19, 2016 for U.S. Appl. No. 13/481,858.
Notice of allowance dated Jun. 3, 2015 for U.S. Appl. No. 14/596,111.
Notice of allowance dated Jul. 1, 2015 for U.S. Appl. No. 13/824,129.
Notice of Allowance dated Jul. 6, 2017 for U.S. Appl. No. 14/653,230.
Notice of Allowance dated Jul. 10, 2017 for U.S. Appl. No. 14/688,764.
Notice of allowance dated Jul. 13, 2015 for U.S. Appl. No. 14/596,111.
Notice of Allowance dated Jul. 20, 2017 for U.S. Appl. No. 14/688,764.
Notice of Allowance dated Jul. 31, 2017 for U.S. Appl. No. 14/119,859.

(56) References Cited

OTHER PUBLICATIONS

Notice of allowance dated Aug. 25, 2015 for U.S. Appl. No. 14/596,111.
Notice of allowance dated Sep. 1, 2015 for U.S. Appl. No. 14/596,111.
Notice of Allowance dated Sep. 8, 2017 for U.S. Appl. No. 14/653,230.
Notice of allowance dated Nov. 21, 2014 for U.S. Appl. No. 13/632,513.
Notice of allowance dated Dec. 3, 2015 for U.S. Appl. No. 13/838,816.
Notice of allowance dated Dec. 15, 2015 for U.S. Appl. No. 13/838,816.
Notomi, et al. Loop-mediated isothermal amplification of DNA. Nucl Acids Res. Jun. 15, 2000; 28(12):E63.
Office action dated Jan. 28, 2014 for U.S. Appl. No. 13/838,816.
Office action dated Jan. 29, 2014 for U.S. Appl. No. 13/481,858.
Office action dated Jan. 30, 2015 for U.S. Appl. No. 13/481,858.
Office Action dated Feb. 14, 2017 for U.S. Appl. No. 14/653,230.
Office Action dated Mar. 4, 2016 for U.S. Appl. No. 14/081,358.
Office Action dated Apr. 5, 2017 for U.S. Appl. No. 14/859,725.
Office action dated Apr. 6, 2016 for U.S. Appl. No. 14/835,070.
Office action dated Apr. 9, 2015 for U.S. Appl. No. 14/596,111.
Office Action dated Apr. 24, 2017 for U.S. Appl. No. 14/119,859.
Office action dated May 1, 2015 for U.S. Appl. No. 13/824,129.
Office action dated Jul. 18, 2013 for U.S. Appl. No. 13/481,858.
Office action dated Jul. 23, 2014 for U.S. Appl. No. 13/824,129.
Office action dated Jul. 25, 2014 for U.S. Appl. No. 13/481,858.
Office Action dated Sep. 1, 2017 for U.S. Appl. No. 14/361,902.
Office action dated Sep. 2, 2014 for U.S. Appl. No. 13/632,513.
Office Action dated Oct. 5, 2015 for U.S. Appl. No. 14/081,358.
Office action dated Oct. 7, 2015 for U.S. Appl. No. 13/838,816.
Office Action dated Oct. 23, 2017 for U.S. Appl. No. 14/859,725.
Office action dated Nov. 5, 2013 for U.S. Appl. No. 13/632,513.
Office action dated Dec. 17, 2015 for U.S. Appl. No. 13/481,858.
Office action dated Dec. 17, 2015 for U.S. Appl. No. 14/835,070.
Office action dated Dec. 19, 2014 for U.S. Appl. No. 13/838,816.
Patolsky, et al. Electrical detection of single viruses. Proc Natl Acad Sci U S A. Sep. 28, 2004;101(39):14017-22. Epub Sep. 13, 2004.
Patolsky, et al. Fabrication of silicon nanowire devices for ultrasensitive, label-free, real-time detection of biological and chemical species. Nat Protoc. 2006;1(4):1711-24.
Peng et al. Interdigitated Array Electrodes with Magnetic Function as a Particle-Based Biosensor. Sensors, 2007 IEEE. pp. 1097-1100.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158(1-2):24-29.
Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.
Rothberg, et al. An integrated semiconductor device enabling non-optical genome sequencing. Nature. Jul. 20, 2011; 475(7356); pp. 348-352. With Supplementary Information, 25 pages.
Sabounchi, et al. Sample concentration and impedance detection on a microfluidic polymer chip. Biomed Microdevices. Oct. 2008;10(5):661-70. doi: 10.1007/s10544-008-9177-4.
Safir, et al. Fabrication of an insulated probe on a self-assembled metallic nanowire for electrochemical probing in cells. IEEE 2006, pp. 898-900.
Saias et al. Design, modeling and characterization of microfluidic architectures for high flow rate, small footprint microfluidic systems. Lab Chip. Mar. 7, 2011;11(5):822-32.
Senapati, et al. A nonamembrane-based nucleic acid sensing platform for portable diagnostics. Topics in Current Chemistry. Apr. 27, 2011; 304:153-169.
Sivamani, et al. Microneedles and transdermal applications. Expert Opin Drug Deliv. Jan. 2007;4(1):19-25.
Sosnowski, et al. Rapid determination of single base mismatch mutations in DNA hybrids by direct electric field control. Proc Natl Acad Sci U S A. Feb. 18, 1997; 94(4): 1119-1123.
Tamayol et al. Laminar Flow in Microchannels With Noncircular Cross Section. J. Fluids Eng 132(11), Dec. 1, 2011 (Nov. 3, 2010) (9 pages).
Terns, et al. CRISPR-based adaptive immune systems. Curr Opin Microbiol. Jun. 2011;14(3):321-7.
Van Der Oost, et al. CRISPR-based adaptive and heritable immunity in prokaryotes. Trends Biochem Sci. Aug. 2009;34(8):401-7.
Voelkerding, et al. Next generation sequencing: from basic research to diagnostics. Clin. Chem. 2009; 55(4):641-658.
Wang, et al. Interaction of the Cas6 riboendonuclease with CRISPR RNAs: recognition and cleavage. Structure. Feb. 9, 2011;19(2):257-64.
Yazdanpanah, et al. Selective self-assembly at room temperature of individual freestanding Ag2Ga alloy nanoneedles. J. Appl. Phys. 98, pp. 073510-7 (2005).
Zhang, et al. Dielectrophoresis for manipulation of micro/nano particles in microfluidic systems. Anal Bioanal Chem. Jan. 2010;396(1): 401-20.
Zheng, et al. Multiplexed electrical detection of cancer markers with nanowire sensor arrays. Nat Biotechnol. Oct. 2005;23(10):1294-301. Epub Sep. 18, 2005.
European Search Report dated Nov. 14, 2017 for European Patent Application No. EP15779780.4.
International Search Report and Written Opinion dated Nov. 16, 2017 for International PCT Patent Application No. PCT/US2017/43159.
Notice of Allowance dated Dec. 8, 2017 for U.S. Appl. No. 14/119,859.
Office Action dated Dec. 18, 2017 for U.S. Appl. No. 15/028,899.
Smolina et al. End invasion of peptide nucleic acids (PNAs) with mixed-base composition into linear DNA duplexes. Nucleic Acids Research. vol. 33. No. 11. pp. e146-e146. Sep. 25, 2005.
Zanoli et al. Isothermal Amplification Methods for the Detection of Nucleic Acids in Microfluidic Devices. Biosensors. vol. 3. No. 1. pp. 18-43. Dec. 27, 2012.
Bobrow et al. Fundamentals of Electrical Engineering, 1995, Holt, Rinehart and Winston, Inc.
Brown et al. AC electroosmotic flow in a DNA concentrator. Microfluid Nanofluid 2:513-523 (2006).
Cheng et al. Single-stranded DNA concentration by electrokinetic forces. J. Micro/Nanolith. MEMS MOEMS 8(2):021107 (Jun. 9, 2009). Abstract only.
Co-pending U.S. Appl. No. 15/950,005, filed Apr. 10, 2018.
Co-pending U.S. Appl. No. 13/397581, filed Feb. 15, 2012.
Co-pending U.S. Appl. No. 15/896,572, filed Feb. 14, 2018.
Co-pending U.S. Appl. No. 16/007,829, filed Jun. 13, 2018.
Co-pending U.S. Appl. No. 16/007,969, filed Jun. 13, 2018.
Co-pending U.S. Appl. No. 16/039,016, filed Jul. 18, 2018.
Cui et al., "Nanowire Nanosensors for Highly Sensitive and Selective Detection of Biological and Chemical Species", Science, vol. 293, pp. 1289-1292 (2001).
EP14767683.7 Extended European Search Report dated Oct. 25, 2016.
Esfandyarpour. Nano-Biotechnology toward Diagnostic Industry: Obstacles and Opportunities. NSTI-Nanotech, vol. 4, p. 421 (2007). Abstract Only.
Examination Report dated Jun. 7, 2016 for Singapore Patent Application No. SG11201402760V.
Fritz et al. Electronic detection of DNA by its intrinsic molecular charge. PNAS 99(22):14142-14146 (2002).
Hsu et al. Wafer-scale silicon nanopillars and nanocones by Langmuir-Blodgett assembly and etching. Applied Physic Lett. 93:133109-1-133109-3 (2008).
Kuhr. Capillary Electrophoresis. Anal. Chem. 62:403R-414R (1990).
Lei et al. Electrokinetic DNA concentration in Microsystems. Sensors and Actuators. A 156(2) (2009). Abstract only.
Moser et al. Biosensor arrays for simultaneous measurement of glucose, lactate, glutamate, and glutamine. Biosens. & Bioelect. 17:297-302 (2002).

(56) References Cited

OTHER PUBLICATIONS

Parizi et al. A Semiconductor Nanobridge Biosensor for Electrical Detection of DNA Hybridization. IEEE Int'l SOI Conference, 2 pgs. (Oct. 6-9, 2008).
Parizi et al. An Internally Amplified Signal SOI Nano-bridge Biosensors for Electrical Detection of DNA Hybridization. IEEE Int'l SOI Conference, 2 pgs. (Oct. 5-8, 2009).
Parizi et al. BioFET for Detection of Biological Species. Stanford University, CIS (Computer-Information-System) Catalog, 1 sheet (2008).
Parizi et al. BioFET Sensor. CIS 2007—Stanford University, 33 pgs. (2007).
Parizi et al. Poster—An Internally Amplified Signal SOI Nanobridge Biosensor for Electrical Detection of DNA Hybridization or Sequence. Poster—1 sheet (Summer 2009).
Parizi et al. Poster BioFET Sensor. CIS 2007—Stanford University, 18 pgs. (2007).
Parizi et al. BioFET Sensor. CIS ADCOM Fall 2009 Stanford University, 28 pgs (Nov. 2009).
Pascault. A Finite Element Study of the DNA Hybridization Kinetics on the Surface of Microfluidic Devices. Thesis, M.S. Chem. Engineer., Worcester Polytechnic Institute, p. 1-148 (Apr. 2007).
PCT/US2014/069624 International Search Report dated May 22, 2015.
Poghossian et al. Possibilities and limitations of label-free detection of DNA hybridization with field-effect-based devices. Sensors and Actuators B 111-112:470-480 (2005).
Ramos et al. AC electric-field-induced fluid flow in microelectrodes. J Colloid Interface Sci 217:420-422 (1999).
U.S. Appl. No. 14/859,725 Notice of Allowance dated Jul. 27, 2018.
U.S. Appl. No. 15/028,899 Notice of Allowance dated Jul. 25, 2018.
U.S. Appl. No. 16/007,969 Office Action dated Aug. 15, 2018.
U.S. Appl. No. 14/081,358 Notice of Allowance dated May 16, 2016.
U.S. Appl. No. 14/936,245 Notice of Allowance dated Sep. 22, 2017.
U.S. Appl. No. 14/936,245 Notice of Allowance dated Dec. 6, 2017.
Stein, D.; Deurvorst, Z.; van der Heyden, F. H. J.; Koopmans, W. J. A.; Gabel, A.; Dekker, C. Electrokinetic Concentration of DNA Polymers in Nanofluidic Channels. Nano Lett. 2010, 10, 765-772.
U.S. Appl. No. 15/028,899 Notice of Allowance dated Jun. 27, 2018.
U.S. Appl. No. 14/361,902 Notice of Allowance dated May 21, 2018.
U.S. Appl. No. 14/859,725 Notice of Allowance dated May 30, 2018.
U.S. Appl. No. 15/183,406 Office Action dated Jun. 21, 2018.
U.S. Appl. No. 15/230,048 Notice of Allowance dated Apr. 5, 2018.
Wilke et al. A micromachined capillary electrophoresis chip with fully integrated electrodes for separation and electochemical detection. Biosens. and Bioelect. 19:149-153 (2003).
Williams, et al. Etch rates for micromachining processing. Journal of Microelectromechanical Systems 5(4):761-778 (1996).
Betz et al. KlenTaq polymerase replicates unnatural base pairs by inducing a Watson-Crick geometry. Nat Chem Biol 8:612-614 (2012).
Co-pending U.S. Appl. No. 16/141,215, filed Sep. 25, 2018.
Park et al. Control of channel doping concentration for enhancing the sensitivity of "top-down" fabricated Si nanochannel FET biosensors. Nanotechnology 20(47):475501 (Oct. 26, 2009).
PCT/US2018/052072 International Search Report and Written Opinion dated Jan. 18, 2019.
U.S. Appl. No. 15/183,406 Office Action dated Mar. 8, 2019.
U.S. Appl. No. 15/655,616 Office Action dated Feb. 26, 2019.
U.S. Appl. No. 15/726,193 Office Action dated Apr. 16, 2019.
U.S. Appl. No. 15/726,217 Office Action dated Mar. 19, 2019.
U.S. Appl. No. 16/007,829 Notice of Allowance dated Nov. 26, 2018.
U.S. Appl. No. 16/283,531 Office Action dated Jul. 18, 2019.
U.S. Appl. No. 16/283,544 Notice of Allowance dated Jul. 11, 2019.
U.S. Appl. No. 15/360,369 Notice of Allowance dated Jul. 5, 2019.
U.S. Appl. No. 15/950,005 Office Action dated Jan. 28, 2019.
Sakata et al. DNA Sequencing Based on Intrinsic Molecular Charges. Angew Chem Int Ed 45:2225-2228 (2006).
U.S. Appl. No. 15/360,369 Notice of Allowance dated Sep. 4, 2019.
U.S. Appl. No. 15/726,193 Notice of Allowance dated Aug. 29, 2019.
U.S. Appl. No. 16/137,408 Office Action dated Aug. 9, 2019.
U.S. Appl. No. 15/726,217 Notice of Allowance dated Dec. 4, 2019.
U.S. Appl. No. 16/137,408 Office Action dated Nov. 19, 2019.
U.S. Appl. No. 16/283,531 Notice of Allowance dated Nov. 22, 2019.
Co-pending U.S. Appl. No. 16/592,545, filed Oct. 3, 2019.
Co-pending U.S. Appl. No. 16/598,591, filed Oct. 10, 2019.
Co-pending U.S. Appl. No. 16/694,367, filed Nov. 25, 2019.
EP19162225.7 Extended European Search Report dated Sep. 18, 2019.
U.S. Appl. No. 15/360,369 Notice of Allowance dated Oct. 10, 2019.
U.S. Appl. No. 15/726,217 Notice of Allowance dated Oct. 8, 2019.
U.S. Appl. No. 15/950,005 Notice of Allowance dated Sep. 13, 2019.

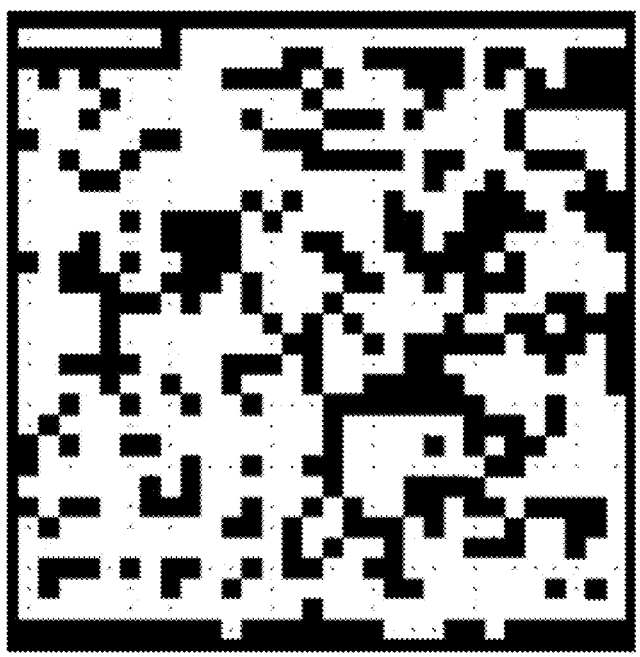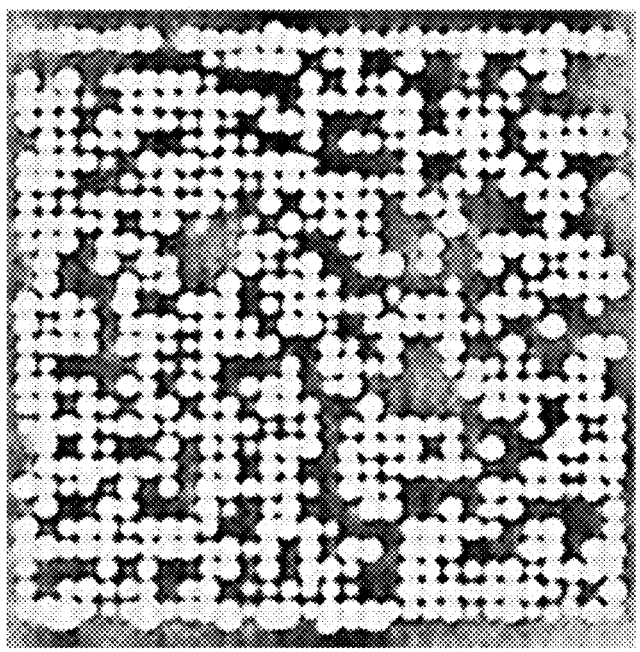
FIG. 8

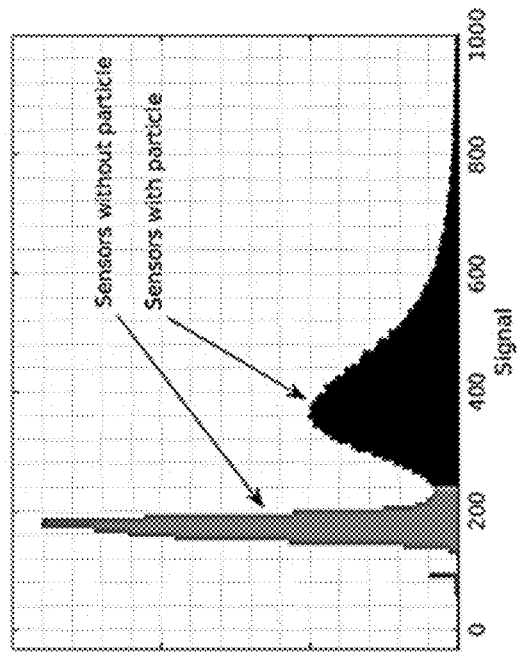
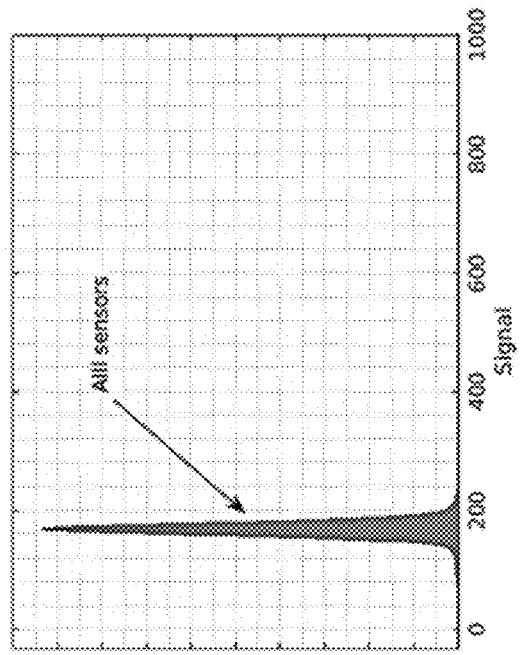
FIG. 9

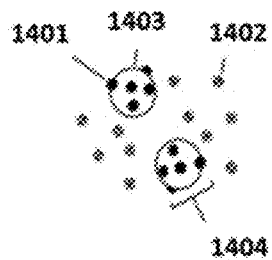
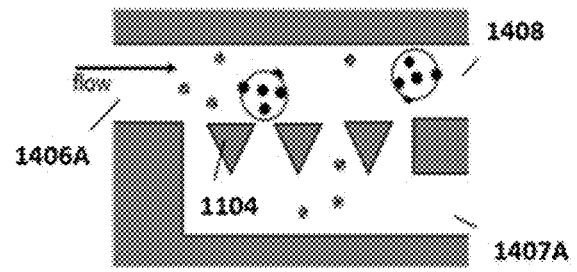
FIG. 14A
FIG. 14B
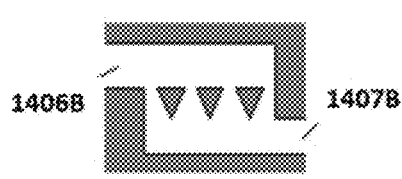
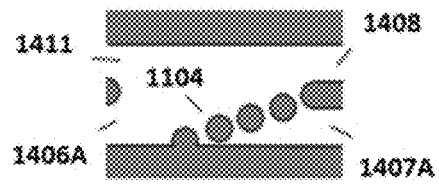
FIG. 14C
FIG. 14D

THE BEAD APPROACH
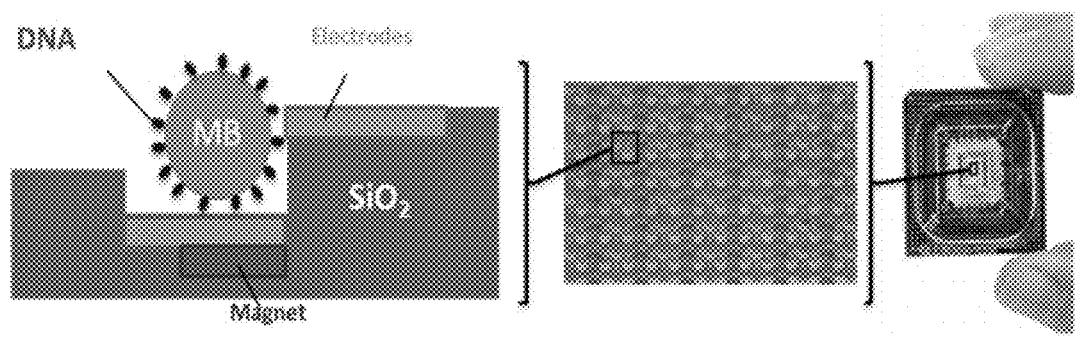
THE ON-CHIP APPROACH
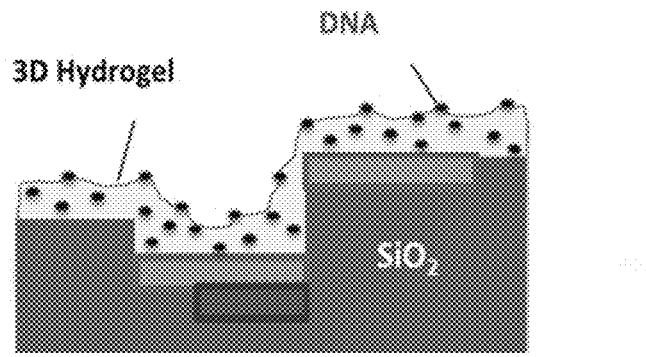
*FIG. 17*

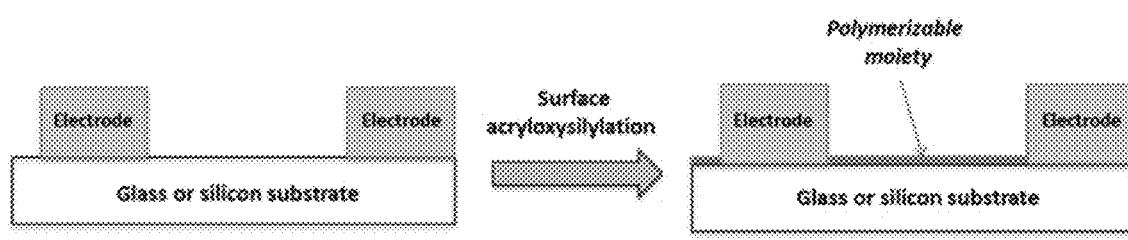
*FIG. 21A*    *FIG. 21B*
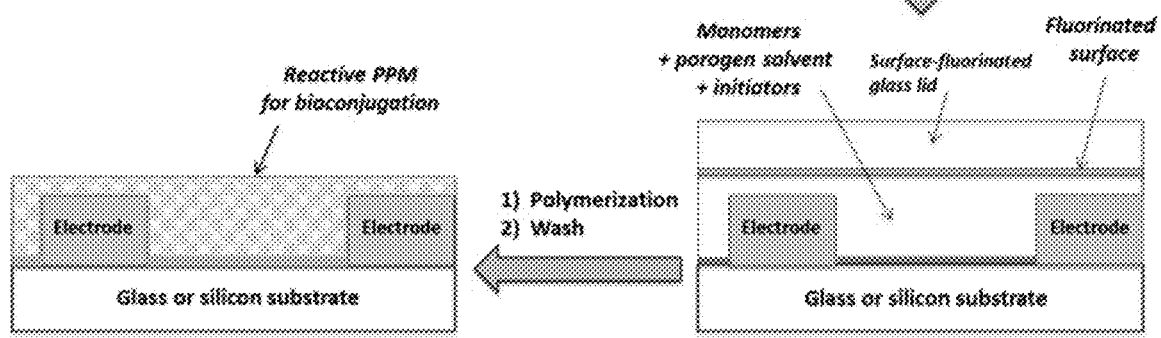
*FIG. 21D*    *FIG. 21C*

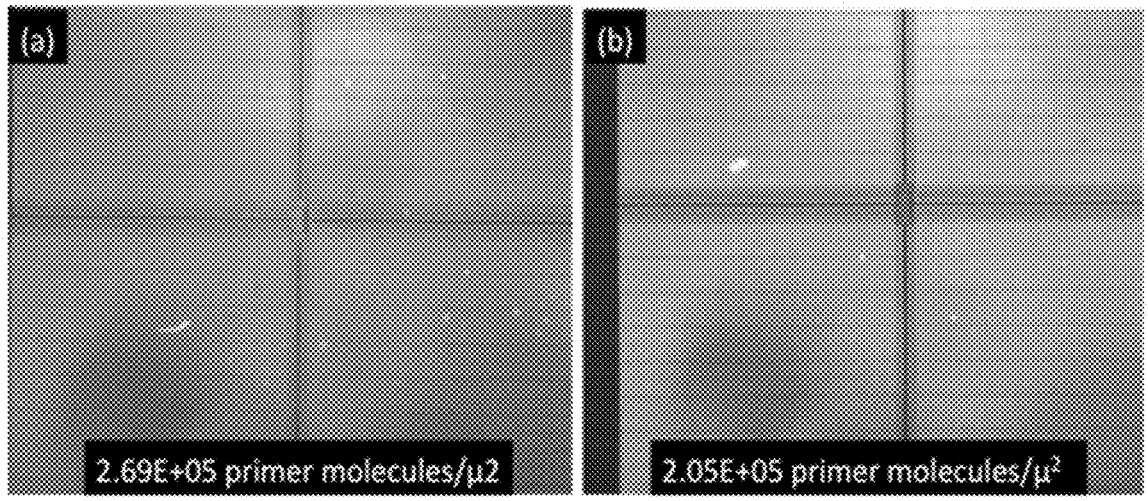
*FIG. 31A*  *FIG. 31B*
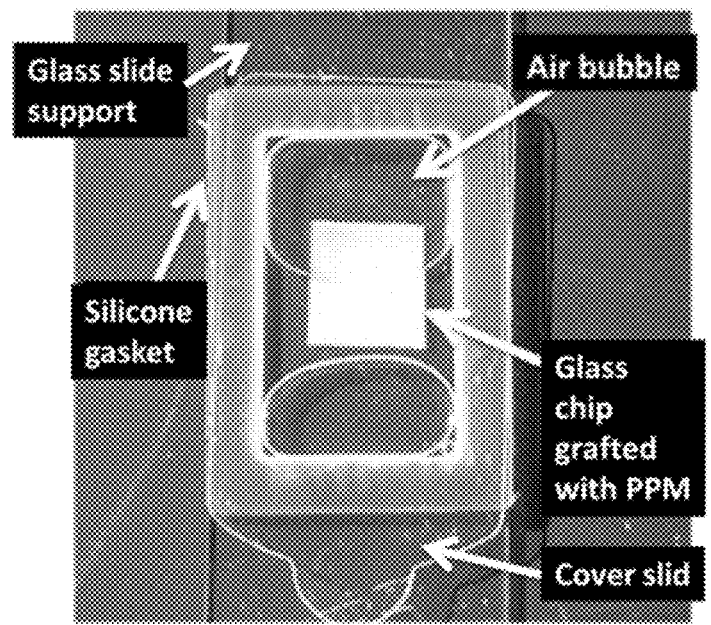
*FIG. 32*

SYSTEMS AND METHODS FOR NUCLEIC ACID SEQUENCING

CROSS-REFERENCE

This application claims the benefit of U.S. Provisional Patent Application No. 62/364,489, filed Jul. 20, 2016, U.S. Provisional Patent Application No. 62/375,197, filed Aug. 15, 2016, U.S. Provisional Patent Application No. 62/418,101, filed Nov. 4, 2016, and U.S. Provisional Patent Application No. 62/444,700, filed Jan. 10, 2017, each of which is entirely incorporated herein by reference.

BACKGROUND

The human genome has created interest in technologies for rapid nucleic acid analysis, including nucleic acid sequencing, both for small and large-scale applications. Presently available nucleic acid sequencing technologies include detection of fluorescent nucleotides; detection of proton byproducts of polymerase activity; and (iii) detection of currents through nanopores. In the context of sequencing, important considerations include accuracy, speed, read length, cost, instrument size and complexity, and the amount of nucleic acid template required to generate sequencing information. Unfortunately, large-scale genome projects often remain too costly and/or infeasible, due to shortcomings in available sequencing technologies. Available sequencing technologies, such as those mentioned above, often have sample preparation, accuracy and/or scalability issues that present significant challenges their mainstream implementation.

SUMMARY

Recognized herein is the need for improved systems and methods for sensing biological reactions, including nucleic acid sequencing reactions. Systems and methods provided herein may have utility in sequencing nucleic acids associated with beads or nucleic acids associated with polymer films. In some cases, signals derived from the sequencing reaction are detected at a buffer composition and concentration that reduces the sensitivity of the system to movements of a bead relative to one or more sensors that detect such signals.

The present disclosure provides methods and systems for sample analysis or identification, such as nucleic acid sequencing. The present disclosure provides methods and systems that may enable sample preparation and identification (e.g., sequencing) without the use of particles, such as beads. This may enable a sample to be prepared and identified at substantially reduced cost and complexity as compared to other systems and methods.

The disclosure also provides systems and methods for improved nucleic acid analysis that overcome status-quo deficiencies and permit low-cost, scalable nucleic acid sequencing technologies. As knowledge of the genetic basis for human diseases increases, there will be an ever-increasing need for accurate nucleic acid analysis tools that are accurate, affordable and scalable for clinical applications. The present disclosure provides systems and methods that make use of redox mediator moieties that are detectable using electronic sensors to perform nucleic acid sequencing.

In an aspect, the present disclosure provides methods for sequencing a nucleic acid template comprising: (a) contacting a nucleic acid template with a sensing fluid containing a population of nucleotides, wherein the nucleic acid template is hybridized to a primer that is coupled to a bead, which bead is positioned proximate to a sensor in a sensor array, wherein the sensor comprises at least two electrodes, and wherein the sensing fluid has a bulk conductivity and a surface of the bead has a surface conductivity to provide a Dukhin number that is less than about 1; (b) using the sensor to detect a change in conductivity within a Debye layer of the bead upon incorporation of at least one nucleotide of the population of nucleotides into a growing nucleic acid strand, which growing nucleic acid strand is derived from the primer and is complementary to the nucleic acid template; (c) washing the sensor array to remove unincorporated nucleotides of the population of nucleotides from the sensor array; and (d) repeating (a)-(c) to obtain sequence information for the nucleic acid template.

In some embodiments, a given electrode of the at least two electrodes is exposed to the sensing fluid. In some embodiments, (b) further comprises detecting a change in impedance within the Debye layer of the bead upon incorporation of the at least one nucleotide. In some embodiments, the change in impedance within the Debye layer is detected at steady state. In some embodiments, the at least two electrodes are positioned within the Debye layer of the bead. In some embodiments, the sensing fluid has a solute concentration between about 0.15 millimolar and about 6 millimolar.

In some embodiments, the method further comprises, prior to (b): (i) contacting the sensor array with a probe fluid, wherein the probe fluid has a bulk conductivity that is at least about 50 times greater than or 50 times less than the conductivity associated with the surface of the bead; and (ii) using the sensor to detect signals that are indicative of a presence of the bead in proximity to the sensor. In some embodiments, a Dukhin number determined from the bulk conductivity of the probe fluid and the conductivity of the surface of the bead is substantially less than 1. In some embodiments, a Dukhin number determined from the bulk conductivity of the probe fluid and the conductivity of the surface of the bead is substantially greater than 1. In some embodiments, (b), (c), and (d) are performed only at sensors of the sensor array at which signals indicative of bead occupancy are observed.

In an aspect, the present disclosure provides methods for determining bead occupancy at sites of a sensor array, comprising: (a) contacting a sensor array with a plurality of beads, wherein the sensor array comprises a plurality of sensors each having at least two electrodes, to provide a given bead of the plurality of beads at a given position in proximity to an individual sensor of the plurality of sensors; (b) contacting the sensor array with a probe fluid that has a bulk conductivity that is at least about 50 times greater than or 50 times less than a conductivity associated with a surface of the given bead; (c) using the individual sensor to detect signals that are indicative of a presence of the given bead in proximity to the sensor; and (d) identifying the given position of the sensor array as occupied by the given bead.

In some embodiments, the probe fluid has a concentration of solutes between about 0.01 millimolar and about 1 molar. In some embodiments, a Dukhin number determined from the bulk conductivity of the probe fluid and the conductivity of the surface of the bead is substantially less than 1. In some embodiments, a Dukhin number determined from the bulk conductivity of the probe fluid and the conductivity of the surface of the bead is substantially greater than 1. In some embodiments, the method further comprises a nucleic acid coupled to the given bead. In some embodiments, the signals comprise electrical current. In some embodiments, a given electrode of the individual sensor is positioned within a Debye layer of the given bead.

In an aspect, the present disclosure provides methods for processing a nucleic acid sample, comprising: (a) providing a mixture comprising a first set of droplets and a second set of droplets, wherein a first droplet of the first set of droplets comprises (i) a bead, (ii) a recombinase, (iii) a polymerizing enzyme, and (iv) a nucleic acid molecule from the nucleic acid sample, and wherein a second droplet of the second set of droplets comprises an activating agent that increases a rate at which the recombinase processes the nucleic acid molecule to permit the primer to hybridize to the nucleic acid molecule to conduct a primer extension reaction in presence of the polymerizing enzyme, to generate an amplification product(s) from the nucleic acid molecule; (b) merging the first droplet with the second droplet in the mixture to generate a third droplet as part of a third set of droplets, wherein the third droplet comprises the bead having coupled thereto the nucleic acid molecule, recombinase, primer and polymerizing enzyme; and (c) conducting the primer extension reaction to generate the amplification product(s) from the nucleic acid molecule in the third droplet.

In some embodiments, the first droplet further comprises buffer, salts, crowding agents, dNTPs, primers, or any combination thereof. In some embodiments, the second droplet further comprises primers, dNTPs, ATP, recombinase loading enzyme, single-stranded DNA-binding protein, an ATP-regenerating unit, buffer, salt, and crowding agents. In some embodiments, the activating agent is a magnesium salt. In some embodiments, formation of the third droplet comprises subjecting the mixture to low speed stirring or shaking. In some embodiments, the primer extension reaction occurs under isothermal conditions.

In some embodiments, the method further comprises directing the third set of droplets through a set of obstacles to control a shape or a size of each droplet of the third set of droplets. In some embodiments, the set of obstacles have a comb-like structure. In some embodiments, the shape or the size of each droplet of the third set of droplets is controlled by flowrate, pressure, obstacle shape, and obstacle size.

In some embodiments, the method further comprises disrupting the third set of droplets with a disrupting mixture comprising an emulsion disruptor and a deactivating agent, wherein disrupting the third set of droplets forms a homogenous solution. In some embodiments, the method further comprises capturing multiple of the bead coupled to amplification product(s) with a capture bead to form a multi-bead complex. In some embodiments, the capture bead exclusively binds to the bead coupled to amplification product(s). In some embodiments, the multi-bead complex is appreciably larger than a non-complexed bead. In some embodiments, the method further comprises directing the beads through a set of obstacles to separate the multi-bead complex from the non-complexed bead via size selection.

In an aspect, the present disclosure provides methods for sequencing a nucleic acid molecule, comprising: (a) activating a sensor comprising a support comprising at least two electrodes and a polymeric material adjacent to the support, wherein the at least two electrodes are exposed to a solution comprising the polymeric material, wherein the polymeric material retains the nucleic acid molecule during a sequencing reaction; (b) subjecting the nucleic acid molecule to the sequencing reaction to yield signals indicative of individual bases of the nucleic acid molecule; (c) during the sequencing reaction, using the at least two electrodes of the sensor to detect the signals; and (d) using the signals detected in (c) to generate a sequence of the nucleic acid molecule.

In some embodiments, the at least two electrodes comprise a chemically inert conducting material. In some embodiments, the support comprises a surface modified silicon oxide or a metal oxide. In some embodiments, the polymeric material is coupled to the surface modified silicon oxide or metal oxide. In some embodiments, the polymeric material bridges or covers the at least two electrodes.

In some embodiments, the polymeric material is a hydrogel. In some embodiments, the hydrogel comprises reactive and non-reactive co-monomers. In some embodiments, the polymeric material is a porous polymer monolith. In some embodiments, the porous polymer monolith is a homopolymer, copolymer, or terepolymer comprising reactive functional groups.

In some embodiments, the polymeric material is seeded with primers and wherein the primers are reactively coupled to the polymeric material. In some embodiments, the primers participate in an amplification reaction to form clonal colonies. In some embodiments, the primers are seeded at a concentration ranging from 1 picomolar to 4000 picomolar. In some embodiments, the amplification reaction is invader amplification, bridge amplification, wildfire amplification, recombinase polymerase amplification, or polymerase chain reaction with a confinement approach.

In some embodiments, during the sequencing reaction, the at least two electrodes are coupled to a Debye layer having of the nucleic acid molecule. In some embodiments, the incorporation of nucleotides into the nucleic acid molecule is performed within the Debye layer. In some embodiments, the signals indicative of the individual bases are electrochemical signals. In some embodiments, the signals indicative of the individual bases are impedance signals. In some embodiments, the signals indicative of the individual bases are detected during steady state conditions.

In an aspect, the present disclosure provides a system for sequencing a nucleic acid molecule, comprising: a sensor comprising a support comprising at least two electrodes and a polymeric material adjacent to the support, wherein during use the at least two electrodes are exposed to a solution comprising the polymeric material, wherein the polymeric material retains the nucleic acid molecule during a sequencing reaction, which sequencing reaction yields signals indicative of individual bases of the nucleic acid molecule; and one or more computer processors operatively coupled to the sensor, wherein the one or more computer processors are programmed to (i) subject the nucleic acid molecule to the sequencing reaction to yield the signals indicative of the individual bases of the nucleic acid molecule; (ii) during the sequencing reaction, use the at least two electrodes of the sensor to detect the signals; and (iii) use the signals detected in (ii) to generate a sequence of the nucleic acid molecule.

In some embodiments, the at least two electrodes comprise a chemically inert conducting material. In some embodiments, the support comprises a surface modified silicon oxide or a metal oxide. In some embodiments, the polymeric material is coupled to the surface modified silicon oxide or metal oxide. In some embodiments, the polymeric material bridges or covers the at least two electrodes.

In some embodiments, the polymeric material is a hydrogel. In some embodiments, the hydrogel comprises reactive and non-reactive co-monomers. In some embodiments, the polymeric material is a porous polymer monolith. In some embodiments, the porous polymer monolith is a homopolymer, copolymer, or terepolymer comprising reactive functional groups.

In some embodiments, the polymeric material is seeded with primers and the primers are reactively coupled to the polymeric material. In some embodiments, the primers participate in an amplification reaction to form clonal colonies. In some embodiments, the primers are seeded at a concentration ranging from about 1 picomolar to about 4000 picomolar. In some embodiments, the amplification reaction is invader amplification, bridge amplification, wildfire amplification, recombinase polymerase amplification, or polymerase chain reaction with a confinement approach.

In some embodiments, during the sequencing reaction, the at least two electrodes are coupled to a Debye layer of the nucleic acid molecule. In some embodiments, the incorporation of nucleotides into the nucleic acid molecule is performed within the Debye layer. In some embodiments, the signals indicative of the individual bases are electrochemical signals. In some embodiments, the signals indicative of the individual bases are impedance signals. In some embodiments, the signals indicative of the individual bases are detected during steady state conditions.

In an aspect, the present disclosure provides methods for sequencing a nucleic acid molecule, the method comprising: (a) tethering a template nucleic acid molecule to a sensor or a surface in proximity to the sensor; (b) creating an elongation complex tethered to the sensor or the surface in proximity to the sensor, wherein the elongation complex comprises (i) a nucleic acid polymerase associated with the template nucleic acid molecule and (ii) an oligonucleotide hybridized to the template nucleic acid molecule; (c) contacting the elongation complex with a solution comprising nucleotides under conditions sufficient to associate a nucleotide complimentary to the template nucleic acid molecule with the elongation complex, wherein a given nucleotide of the nucleotides is coupled to a redox mediator moiety; (d) using the sensor to detect a signal indicative of the redox mediator moiety when the nucleotide is associated with the elongation complex; (e) incorporating the nucleotide into the oligonucleotide to subject the redox mediator moiety to release from the nucleotide; and (f) repeating (c)-(e), thereby sequencing the template nucleic acid molecule.

In some embodiments, a plurality of clonal template nucleic acid molecules is tethered to the sensor or the surface in proximity to the sensor. In some embodiments, the plurality of clonal template nucleic acid molecules is generated with the aid of polymerase walking. In some embodiments, the elongation complex is tethered to the sensor or the surface in proximity to the sensor via the polymerase. In some embodiments, in each iteration of (c), the solution comprises only one of the nucleotides adenine (A), cytosine (C), guanine (G), uracil (U) or thymine (T), or a variant thereof, and each iteration of (c) contacts the elongation complex with a different nucleotide.

In some embodiments, the redox mediator moiety comprises an organic compound, an organometallic compound, a nanoparticle, or a metal. In some embodiments, a plurality of redox mediator moieties are bound to the nucleotide. In some embodiments, the elongation complex is tethered to the sensor or the surface in proximity to the sensor via a binding pair. In some embodiments, the binding pair is a biotin-streptavidin binding pair. In some embodiments, the redox mediator moiety is attached to a phosphate of the nucleotide. In some embodiments, the nucleotide is associated with the elongation complex for a time period between about 10 and about 500 milliseconds (ms). In some embodiments, the sensor is among a plurality of sensors and wherein a given one of the plurality of sensors is individually addressable.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 2A shows a schematic of an example sensor array; FIG. 2B shows a schematic of an example sensor array with beads carrying nucleic acids, which beads are immobilized to the sensor array; FIG. 2C shows a schematic of an example sensor array with beads carrying nucleic acids and immobilized to the sensor array in contact with reagents suitable for nucleic acid amplification; FIG. 2D shows a schematic of an example sensor array where nucleic acid amplification occurs on beads positioned at various sensors of the sensor array; FIG. 2E shows a schematic example of removing reagents from an example sensor array; FIG. 2F shows a schematic of an example sensor array where nucleic acids are sequenced at various positions of the sensor array;

FIG. 8 graphically depicts an example of bead occupancy on an example sensor array;

FIG. 9 graphically depicts example data relating to bead occupancy on example sensor arrays;

FIG. 11A shows droplets flowing towards an obstacle; FIG. 11B shows droplet distorting around the object due to shear forces; FIG. 11C shows a droplet splitting around the obstacle; FIG. 11D shows obstacles may have an arbitrary shape; FIG. 11E shows obstacles may be confined in a flow cell; and FIG. 11F shows and array of obstacles;

FIG. 12A shows an obstacle array within a microfluidic channel; FIG. 12B shows a multiplexing of arrays; FIG. 12C shows an example of an on-chip amplification; FIG. 12D shows using membrane valves and pumps to move liquid; FIG. 12E shows a closed version of a membrane pump;

FIGS. 14A-14D schematically illustrate obstacle based bead sorting; FIG. 14A shows unamplified beads appearing amplified; FIG. 14B shows separation of amplified beads from unamplified beads by use of obstacles; FIG. 14C shows a different implementation of the separation approach; FIG. 14D shows a further implementation of the separation approach;

FIG. 16A shows an obstacle array; FIG. 16B shows another obstacle array; FIG. 16C shows a crude emulsion prior to the fluid being directed through an obstacle array; FIG. 16D shows an emulsion after the fluid is directed through an array;

FIG. 17 schematically illustrates systems for bead and bead free nucleic acid sequencing;

FIGS. 21A-21D schematically illustrate preparation of a porous polymer monolith (PPM) thin film; FIG. 21A shows a support surface to be modified; FIG. 21B shows the surface modification with a polymerizable silane group; FIG. 21C shows the system before polymerization; FIG. 21D shows the system after polymerization;

FIG. 26A schematically illustrates immobilization of primers to the polymer coated support; FIG. 26B schematically illustrates a surface confined amplification method; FIG. 26C shows template density after amplification as a function of starting template concentration;

FIG. 30A shows visualization of primer density before and after a amplification reaction; FIG. 30B shows visualization of accumulated nucleic acid incorporation and electronic detection of nucleic acid incorporation;

FIGS. 31A and 31B show the density of primers conjugated to polymer coated supports before and after rinsing with an alkaline solution; FIG. 31A shows primer density before rinsing with an alkaline solution; FIG. 31B shows primer density after rinsing with an alkaline solution;

FIG. 32 shows a thin-layer cell used for conjugation of primers to a PPM thin film;

FIG. 34A schematically depicts an example method for producing clonal colonies of nucleic acid molecules; FIG. 34B schematically depicts an example surface on which colonies of nucleic acids are present.

DETAILED DESCRIPTION

Figure 1:
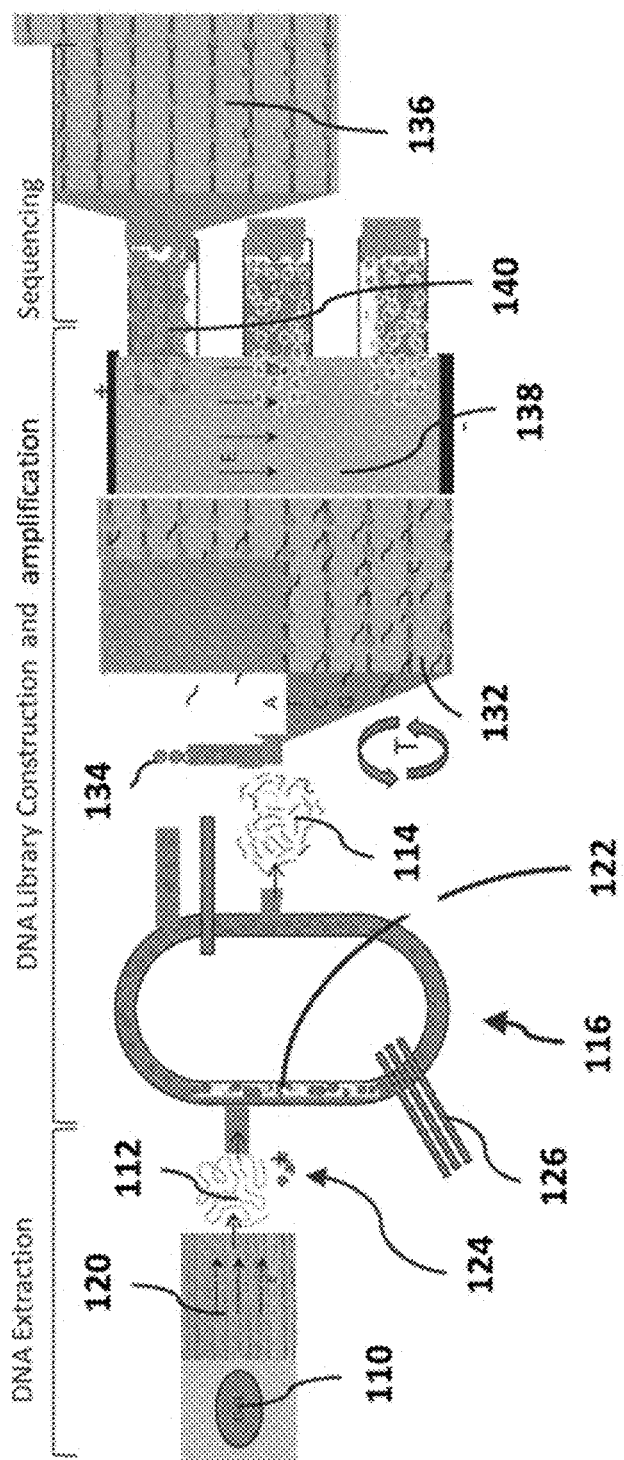
FIG. 1 schematically depicts an example integrated sequencing platform.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "adjacent to," as used herein, generally refers to next to, in proximity to, or in sensing or electronic vicinity (or proximity) of. For example, a first object adjacent to a second object can be in contact with the second object, or may not be in contact with the second object but may be in proximity to the second object. An object adjacent to another object may have one or more intervening objects (e.g., layers). In some examples, a first object adjacent to a second object is within about 0 micrometers (μm), 0.001 μm, 0.01 μm, 0.1 μm, 0.2 μm, 0.3 μm, 0.4 μm, 0.5 μm, 1 μm, 2 μm, 3 μm, 4 μm, 5 μm, 10 μm, or 100 μm of the second object.

As used herein, the terms "amplifying", "amplification" and "nucleic acid amplification" are used interchangeably and generally refer to generating one or more copies or "amplified product" or "amplicons" of a nucleic acid. Amplification of a nucleic acid may be linear, exponential, or a combination thereof. Non-limiting examples of nucleic acid amplification methods include reverse transcription, primer extension, polymerase chain reaction, ligase chain reaction, helicase-dependent amplification, asymmetric amplification, rolling circle amplification, recombinase polymerase amplification (RPA), and multiple displacement amplification (MDA). In some embodiments, the amplified product may be DNA. In cases where a target RNA is amplified, DNA can be obtained by reverse transcription of the RNA and subsequent amplification of the DNA can be used to generate an amplified DNA product. In cases where DNA is amplified, DNA amplification may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, nucleic acid amplification is dependent upon thermal cycling conditions. In other cases, nucleic acid amplification is isothermal.

The term "bead," as used herein, generally refers to any type of particle suitable for association with a nucleic acid or other biological molecule. A bead may have a regular shape, including spherical and non-spherical shapes and 1:1 aspect ratio and non 1:1 aspect ratios. In some cases, a bead has a regular shape (e.g., a spherical bead) or may have an irregular shape (e.g., a globular-bead comprising multiple domains of magnetic material). A bead may comprise any type of suitable material(s) with non-limiting examples that include metals, ceramics, magnetic materials, a polymer(s) and combinations thereof. In some cases, a bead is magnetic and, with a magnetic force applied to the bead, can be manipulated/immobilized. Non-limiting examples of beads include nanobeads (e.g., nanorods, nanospheres, nanoshells, nanotubes, nucleic acid nanoballs, etc.), microbeads (e.g., microspheres, microbeads, etc.), quantum dots, cells, polymeric scaffolds and combinations thereof.

The terms "nucleic acid," "nucleic acid molecule," "nucleic acid fragment," "oligonucleotide" or "polynucleotide," are used herein interchangeably, and generally refer to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some cases, a nucleic acid molecule is circular. Moreover, a nucleic acid can have any suitable length, such as a length of at least about 100 bases, 200 bases, 300 bases, 400 bases, 500 bases, 1 kilobase (kb), 2 kb, 3, kb, 4 kb, 5 kb, 10 kb, or 50 kb.

Nucleic acids may include one or more non-standard nucleotide(s), nucleotide analog(s) and/or modified nucleotides. Examples of such nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, aminoallyl-dUTP (aa-dUTP) and aminohexylacrylamide-dCTP (aha-dCTP). Nucleic acids may also be modified at a base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "nucleic acid sequencing" and "sequencing" are used interchangeably and generally refer to the determination of a nucleotide sequence of a nucleic acid. In some cases, the entire nucleotide sequence of a nucleic acid is determined. In other cases, only a portion of the nucleotide sequence of a nucleic acid is determined. Nucleic acid sequencing can be conducted in any suitable fashion, including via sequencing-by-synthesis. In sequencing-by-synthesis, nucleotides are sequentially incorporated into a primer hybridized to a template nucleic acid to-be-sequenced (e.g., a growing nucleic acid strand), often via the action of an enzyme such as a polymerase. During and/or after the incorporation of each nucleotide, signals indicative of incorporation can be detected. When such signals are associated with a particular type of nucleotide (e.g., a nucleotide having an A, T, C, G or U base), the signals can be used to determine the particular nucleotide incorporated and, thus, via basepairing rules, the complementary nucleotide of the template nucleic acid to-be-sequenced. The process of nucleotide incorporation and detection repeats until a sequence of the nucleic acid is determined.

The term "polymerase," as used herein, generally refers to any enzyme capable of catalyzing a polymerization reaction. A polymerase can be naturally occurring or can be synthetic. In some cases, a polymerase is a nucleic acid polymerase that is capable of facilitating the sequential incorporation of nucleotides to a primer hybridized (e.g., a growing nucleic acid strand) to a template nucleic acid. Examples of nucleic acid polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, a polymerase is a single subunit polymerase. Moreover, a polymerase can have relatively high processivity, namely the capability of the polymerase to consecutively incorporate nucleotides to a primer without releasing the nucleic acid template to which the primer is hybridized.

The term "nucleotide," as used herein, generally refers to an organic molecule that serves as the monomer, or subunit, of a nucleic acid molecule, such as a deoxyribonucleic (DNA) molecule or ribonucleic acid (RNA) molecule. In some embodiments, a nucleotide may also be a peptide nucleic acid (PNA) nucleotide or a locked nucleic acid (LNA) nucleotide.

The term "primer," as used herein, generally refers to a strand of nucleic acid that serves as a starting point for nucleic acid synthesis, such as polymerase chain reaction (PCR). In an example, during replication of a DNA sample, an enzyme that catalyzes replication starts replication at the 3'-end of a primer attached to the DNA sample and copies the opposite strand.

The term "clonal," as used herein, generally refers to at least some, substantially all, or all, of the populations of a sensor area being of the same nucleic acid sequence. There may be two population associated with a single sample nucleic acid fragment, as may be used for "mate pairs," "paired ends", or other similar methodologies; the populations may be present in roughly similar numbers in the sensor area, and may be randomly distributed over the sensor area.

The term "confinement," as used herein, generally refers to a species, moiety, or molecule generated (such as DNA) in one sensor area staying associated with the same or substantially the same sensor area so as to maintain or substantially maintain the clonal nature of the sensor area.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules.

The term "reagent," as used herein, generally refers to one or more substances that can be employed for use sample preparation or analysis. Sample preparation can include sample processing. An example of sample preparation is a nucleic acid amplification reaction, such as polymerase chain reaction (PCR). Examples of reagents for use with nucleic acid amplification reactions include one or more primers and a polymerase, as well as cofactors (e.g., magnesium or manganese). In some cases, nucleic acid amplification is not a PCR reaction.

The terms "surface modified" or "surface modification," as used herein, generally refers to a surface in which the chemical or physical (e.g., electronic) characteristic(s) has been changed or altered. A chemical surface modification may include treating the surface with an acid, base, or ozone. The chemically modified surface may be coupled with a reactive linker. The reactive linker may include, but is not limited to, silane coupling agents, homobifunctional crosslinkers, heterobifunctional crosslinkers, trifunctional crosslinkers, bifunctional chelating agents, biotinylation reagents, or any other reactive functional group. Physical surface modifications may include, but are not limited to, wet etching and dry etching.

Systems for Detecting a Biomolecule

The present disclosure provides an integrated sequencing platform that may include various components. The integrated sequencing platform may be used in various applications, such as sequencing a nucleic acid sample from a living subject.

In the context of nucleic acid sequencing, beads comprising clonal populations of nucleic acid can be provided (e.g., via fluid flow, perhaps through one or more fluid channels (e.g., microfluidic channels) associated with the sensor array) to the sensor array, and the beads immobilized to sensor sites. After bead immobilization, reagents suitable for nucleic acid sequencing can be serially contacted with the sensor array to sequence nucleic acids on a bead associated with a given sensor site. For example, in a first round, a sensor array may be contacted with a fluid comprising a primer that can hybridize with nucleic acids and be extended in template-directed fashion via the action of a polymerase. The array can then be washed to remove any non-hybridized primers. In a second round, the sensor array may be contacted with a fluid comprising reagents suitable for primer extension (e.g., polymerase, co-factors, suitable buffer) and a particular known nucleotide (e.g., A, T, C, G or U). Incorporation occurs and, at array sites where incorporation occurs, sensors at those sites can detect signals indicative of incorporation via any suitable modality, including one or more of those described elsewhere herein. Where signal is detected, the signal can be interpreted as incorporation of the particular known nucleotide into the template. In some cases, the signal magnitude/intensity can be used to determine how many of the particular known nucleotides are incorporated into nucleic acids at a given site, such as in the case where the known nucleotide is incorporated more than once (e.g., in the case of a repeat template complement). The sensor array can then be washed and the cycle repeated for each remaining known nucleotide used for sequencing and the entire set of cycles then repeated for each nucleic acid sample nucleotide, until sample nucleic acids bound to beads are sequenced.

For example, a sensor array with sites occupied by beads comprising clonal populations of nucleic acids can be contacted with a fluid comprising a primer(s) that hybridize to clonal nucleic acids. The sensor array can then be washed and then contacted with a fluid comprising an adenine-containing nucleotide, a polymerase and any necessary co-factors in a suitable buffer. Adenine-containing nucleotide can incorporate to hybridized primers, where the next template site on clonal nucleic acids is a thymine-containing nucleotide. The array can then be washed and the incorporate-and-wash cycle repeated for each of guanine-containing nucleotides, thymine-containing nucleotides and cytosine-containing nucleotides. Once the four types of nucleotides have been contacted with the sensor array, that cycle can also repeat for another set of contacting with each of the four types of nucleotides, until sample nucleic acids bound to beads are sequenced.

In some cases, nucleic acid (e.g., deoxyribonucleic acid (DNA)) amplification and sequencing may be performed sequentially, or even simultaneously, on the same array. In such cases, the array may comprise components useful for one or both of amplification and sensing at a given array location. In addition to having a feature that can immobilize a bead, a given array site can include one or more electrodes. The one or more electrodes may comprise one or more separate electrodes that can provide an electric field that generates a virtual well to confine reagents to an array site and one or more separate electrodes that function as sensors. In some cases, the one or more electrodes may comprise one or more electrodes that can both provide an electric field and also function as a sensor.

The sensor array may be incorporated into an integrated sequencing platform. An integrated sequencing platform may include one or more of a nucleic acid (e.g., DNA)

extraction module, a library construction module, an amplification module, an extraction module, and a sequencing module. In some embodiments the systems may be separate and/or in modular format. In some embodiments, the integrated sequencing platform can include one, two, three, four, or all five of these systems. In some cases, the modules can be integrated within a single unit (e.g., a microfluidic device), a single array (e.g., a sensor array that may be re-usable) or even a single device. Examples of integrated sequencing platforms can be found in PCT Patent Application No. PCT/US2011/054769, PCT Patent Application No. PCT/US2012/039880, PCT Patent Application No. PCT/US2012/067645, PCT Patent Application No. PCT/US2014/027544, PCT Patent Application No. PCT/US2014/069624 and PCT Patent Application No. PCT/US2015/020130, each of which is entirely incorporated herein by reference.

An example of an integrated sequencing platform is schematically depicted in FIG. 1. The integrated sequencing platform includes a library construction module (e.g., nucleic acid library construction system), which may include one or both of a nucleic acid fragmentation element and a size selection element. As shown in the example of FIG. 1, the library construction system includes nucleic acid (e.g., DNA) fragmentation and size selection elements in a single unit 116. Nucleic acid 112 provided to the fragmentation and size selection unit 116 can be extracted from a biological sample (e.g., a cell 110) and separated 120 from other materials in the biological sample prior to fragmentation. The fragmentation and size selection unit 116 can be configured to produce nucleic acid fragments, such as double-stranded nucleic acid fragments, which may or may not have blunted ends, via the elements and methods described below. The fragmentation and size selection unit 116 can include one or more microfluidic channels 122 within which nucleic acid may be disposed along with a set of fragmentation beads 124. Nucleic acid 112 collected in a nucleic acid (e.g., DNA) extraction system (shown for example in FIG. 1) can be conveyed or "injected" into the nucleic acid (e.g., DNA) fragmentation and size selection unit 116 by any suitable method (e.g., pressurized injection, electrophoretic movement, gravity feed, heat-induced movement, ultrasonic movement and/or the like). Similarly, fragmentation beads 124 can be conveyed into the nucleic acid (e.g., DNA) fragmentation element and size selection unit 116 by any suitable method.

The fragmentation element and/or size selection unit 116 can include a pump 126 to produce movement of a fluid (e.g., a fluid comprising nucleic acid (e.g., DNA) and fragmentation beads 124) within a microfluidic channel 122. The pump 126 can be, for example, a peristaltic pump, rotary pump, or reciprocating pump. In some embodiments, the pump 126 can include one or more microfluidic elements in fluid communication with the microfluidic channel 122, and may have a flexible side-wall that, when deformed, produces a flow within the microfluidic channel 122. In other embodiments, however, another suitable strategy can be used as an alternative or in addition to produce movement fluid within the microfluidic channel 122, with non-limiting examples, that include selective heating and cooling of the fluid, pneumatic pressurization of the microfluidic channel, electrophoretic motion, or the like.

As shown in FIG. 1, The fragments 114 that are generated by the by the size selection unit 116 can be transferred to an amplification unit 132 along with beads 134 that are capable of binding the fragments 114. The amplification unit 132 can include an array of features that are each capable of retaining a bead. Beads may be bound to the array via magnetic (e.g., via a magnetic feature), electrostatic (e.g., via one or more electrodes), or via a member of a binding pair (e.g., via hybridization of nucleic acid with nucleic acid coupled to the array). In some cases, fragments may be provided to an amplification unit at dilute concentrations in order to obtain a desired ratio of molecules of sample nucleic acid to beads. The flow rates of beads 134 and fragments 114 supplied to the amplification unit 132 can be carefully controlled such that, on average, less than one fragment is associated with a given bead. Such a ratio can help to ensure the clonal nature of amplicon populations generated in the amplification unit 132. Binding of the fragments 114 to beads can be achieved via any suitable route, including hybridization with an oligonucleotide coupled to the beads, covalent linkages, an associated binding ligand pair, or any other binding technique. The binding may be a non-reversible covalent binding, a reversible covalent binding, or a reversible non-covalent binding.

Reagents for amplification of bound fragments are provided to the array and amplification of the fragments can then proceed in any suitable fashion, including via a polymerase chain reaction (PCR), strand-displacement amplification, isothermal amplification or any other suitable amplification method, to generate a population of beads, each bead comprising a clonal population of nucleic acids. Nucleic acid amplification may be performed in multiple cycles. Once a first round of amplification is completed after contacting the array with a first set of nucleic acid fragments, the array may be washed in order to remove any unbound amplicons and other reagents in solution. Following washing, a second round of amplification may be completed, by contacting the array with additional nucleic acid fragments and then exposure of those fragments to reagents suitable for nucleic acid amplification. Where clonal amplification is complete (e.g., no binding sites remain on some beads) the second fragments may bind only to beads not already comprising amplicons, as sites with amplicons from first round of amplification may be fully loaded with amplicons. The process may be repeated for any number of amplification cycles until capture sites are exhausted. Utilizing multiple rounds of amplification may help eliminate double Poisson distribution problems and help ensure that each sensor site is associated with only one nucleic acid sequence, yet the occupancy of array sites is maximized.

In some cases, a virtual well (e.g., generated via an electric and/or magnetic field) produced by one or more electrodes at a given array site can be implemented to confine amplification reagents to the given array site. Virtual wells can permit amplification of nucleic acids at a sensor position without cross-contamination of reactants with those of other sensors of the array. Amplification within a virtual well can aid in generating clonal populations of amplicons.

Once amplification is complete, but prior to sequencing, clonal beads generated from amplification can be transported to an enrichment unit 138 that separates beads having amplicons from those without nucleic acid. The enrichment module may include any method of sorting beads comprising amplicons from those not comprising amplicons. Sorting methods may include size selection, electrophoretic sorting, or sorting by bead capture. Sorting bead capture may include associating beads comprising amplicons with capture moiety through hybridization, ligand pair binding, or any other reversible binding technique. In some cases, separation methods may make use of electrophoretic methods, implemented in an electrophoretic sorter. In an electrophoretic sorter, null beads (e.g., beads without nucleic acids), as well as beads subject to incomplete amplification or those comprising overly short nucleic acids, can be sorted from beads comprising desired amplicons via an electrophoretic force (e.g., via an applied electric field) generated by components of the sorter onto beads.

An electrophoretic sorter may comprise one or more channels capable of accepting sorted beads. Beads with desired amplified product may have sufficient charge to be directed to an outlet channel via their interaction with an electric field. The sorted beads can be collected from the outlet channel and provided back to the amplification system for amplification. Moreover, beads without appropriate amounts of amplified product and/or without amplicons of adequate length may flow through the electrophoretic sorter and, instead, be directed into a waste channel. The beads may be collected from the waste channel and may be reused for another cycle of amplification or other purpose upon appropriate cleaning to remove any undesirable species. For example, beads may be washed with a bleaching agent, such as hydrogen peroxide, to help ensure that no contaminants remain on the beads so that they may be reused.

Additional examples of enrichment systems and electrophoretic sorters are described in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is entirely incorporated herein by reference.

Once separation is complete, beads 140 that have amplicons can be provided to a sequencing unit (e.g., a sequencing unit comprising a sensor array 136) and sequenced. Enrichment of clonal beads may be completed prior to sequencing. In some cases, enrichment of clonal beads is not completed prior to sequencing. In such cases, the amplified material generated during amplification is provided directed to a sequencing unit and the nucleic acids bound to the clonal beads are sequenced.

A sequencing unit may comprise one or more sensor arrays, each array comprising a plurality of sites. A given site of the array can include a sensor and, in some cases, a force mechanism for immobilizing a bead at the given site and adjacent to its sensor. In some cases, the force mechanism may be a magnet, such as, for example, a permanent magnet or an electromagnet. A magnetic force applied by the magnet can immobilize beads (e.g., beads comprising a magnetic material) that are responsive to a magnetic force. In some cases, the force mechanism comprises one or more elements (e.g., one or more electrodes) that generate an electrostatic force. An electrostatic force applied by the one or more elements can immobilize beads (e.g., beads comprising a charged species, such as nucleic acids) that are responsive to an electrostatic force. In some cases, a given site of a sensor array comprises a physical trench or well that can immobilize a bead. In some cases, a given site of a sensor array comprises one or more molecules of one member of a binding pair that can bind a bead comprising the other member of the binding pair. Such members include an oligonucleotide that can hybridize with another oligonucleotide coupled to a bead, streptavidin or biotin that can bind with the other of streptavidin and biotin coupled to a bead. Moreover, in some cases, a sensing array may be free of wells and may be substantially planar.

A sensor at a given position of a sensor array may be any suitable sensor. In some cases, a sensor is an electronic sensor. An electronic sensor can include one or more electrodes (in some cases, at least two electrodes) that are capable of measuring signals indicative of one or more of a change of impedance, a change in charge, a change in ion concentration, and/or a change in conductivity associated with a bead and/or a species coupled to a bead. In some cases, a sensor may comprise NanoNeedle and/or NanoBridge sensor and/or an optical sensor. A NanoBridge and/or NanoNeedle sensors may be capable of detecting one or more of a change in pH, a change in charge, a change in conductivity and a change in impedance. NanoBridge and NanoNeedle sensors are described in more detail in U.S. Patent Publication No. US 2012/0138460, PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624 and PCT Patent Application No. PCT/US2015/020130, each of which is entirely incorporated herein by reference.

Moreover, one or more sensors of a sensor array may be independently addressable. An independently addressable sensor is an individual sensor in an array whose response can be independently detected from the responses of other sensors in the array. An independently addressable sensor can also refer to an individual sensor in an array that can be controlled independently from other sensors in the array.

Sensing of a sensor may be based on one or more of local pH change, local impedance change, local heat detection, local capacitance change, local charge concentration (or change thereof), and local conductivity change associated with a bead immobilized in proximity to a sensor and/or species (e.g., nucleic acid) associated with the bead. Changes in one or more of these measures can be effected by a reaction (e.g., a nucleic acid sequencing reaction) involving a species coupled to the bead and/or a binding event (e.g., nucleic acid hybridization) involving a species coupled to the bead. Such measurements can be made by directly detecting or detecting signals that are indicative of a local pH change, local impedance change, local heat detection, local capacitance change, local charge concentration (or change thereof), and local conductivity change of a bead or species (e.g., nucleic acid) coupled to a bead immobilized in proximity to a sensor.

In some cases, one or more of these changes may be a change within the Debye layer (or Debye length) of a bead or a species (e.g., nucleic acid) coupled to the bead or a sensor. The Debye layer may have a characteristic thickness or length referred to as the Debye length. Moreover, in some cases, sensing occurs within the Debye layer (or Debye length) of (i) a bead (ii) a species associated nucleic acid associated with the bead, or (iii) a sensor. A Debye layer may be an electric (or electrical) double layer that is a charge or conductivity boundary layer having a thickness around a bead, species coupled the bead or a sensor, and/or the sensor. In some cases, sensing occurs within the Debye layer spanning a sensor and a bead. Furthermore, where a sensor comprises one or more electrodes (e.g., at least two electrodes), the one or more electrodes may be electrically coupled to the Debye layer of a bead or a species coupled to a bead (e.g., a nucleic acid). In some cases, the one or more electrodes may be within the Debye layer of a bead or a species coupled to a bead (e.g., a nucleic acid). Such sensor configurations are described, for example, in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is entirely incorporated herein by reference.

Signals from the sensor may be detected transiently or during steady state conditions. In a transient signal detection modality, the detection occurs during or closely after a biological event, such as nucleotide incorporation. In steady state detection, reading of the sensor may occur after the "completion" of the biological event or incorporation event. A steady state change in signal may remain until a change is introduced to the environment around the sensor. Steady state measurements may provide several advantages over of the transient detection modality. The sensor may be utilized in a manner whereby less data is requires as the sensor may no longer be required to be read at a high data rate.

Figure 2A:
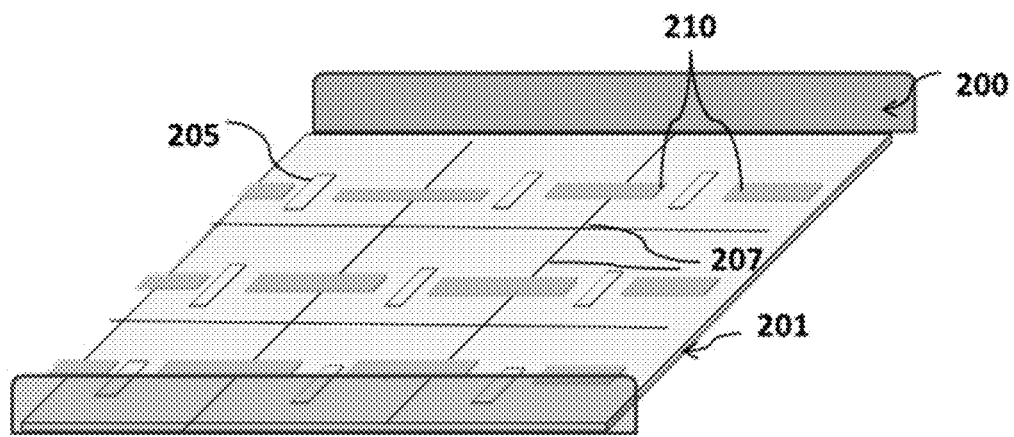
FIGS. 2A-2F show example sensor arrays and sensor use.

An example of a combined amplification and sequencing array and use of the example array is depicted in FIGS. 2A-2F. As shown in FIG. 2A, the array 200 is configured on a substrate 201 (e.g., a substantially planar substrate) that can comprise sensors (e.g., nanosensors) sometimes in communication with microfluidic channels defined within the platform. Sensors may be associated with substrate 201 and substrate 201 may also be associated with magnetic 210 and electrode 205 and 207 elements. Magnetic beads may be positioned over the sensors by the magnetic 210 or electrode 205 and 207 elements. The magnetic elements may form localized magnetic fields and the electrode elements may form localized electric fields in order to position a bead at various sensors of the array 200. Moreover, the magnetic and/or electric fields may create an area of confinement for beads at occupied positions of the array 200.

Figure 2B:
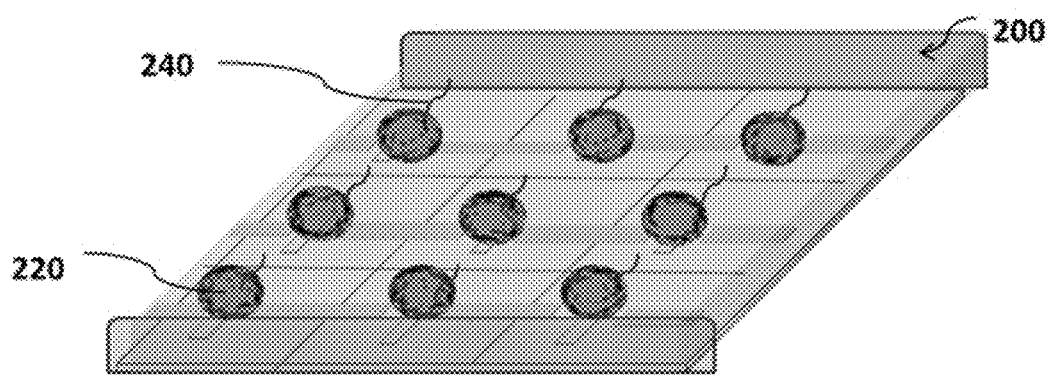

As shown in FIG. 2B, a sample comprising nucleic acid 240 (e.g., nucleic acid fragments) may be conveyed to the array 200. Nucleic acid 240 may be any suitable type of nucleic acid, including types of nucleic acids described elsewhere herein. In some cases, introduction of the nucleic acid 240 to the array 200 may be via microfluidic channels associated with the array 200. As shown, the array 200 may be configured with pre-localized magnetic beads 220 and the magnetic beads may be associated with primers capable of hybridizing with nucleic acid 240, such that nucleic acid 240 is captured by and becomes associated with the beads 220. The magnetic beads 220 may be positioned on the array 200 via the magnetic elements 210 and/or electrode 205 and 207 elements. Alternatively or in addition, primers may be attached, bound, or associated with a sensor at a position of the array 200 and used to trap nucleic acid 240 at the sensor.

Figure 2C:
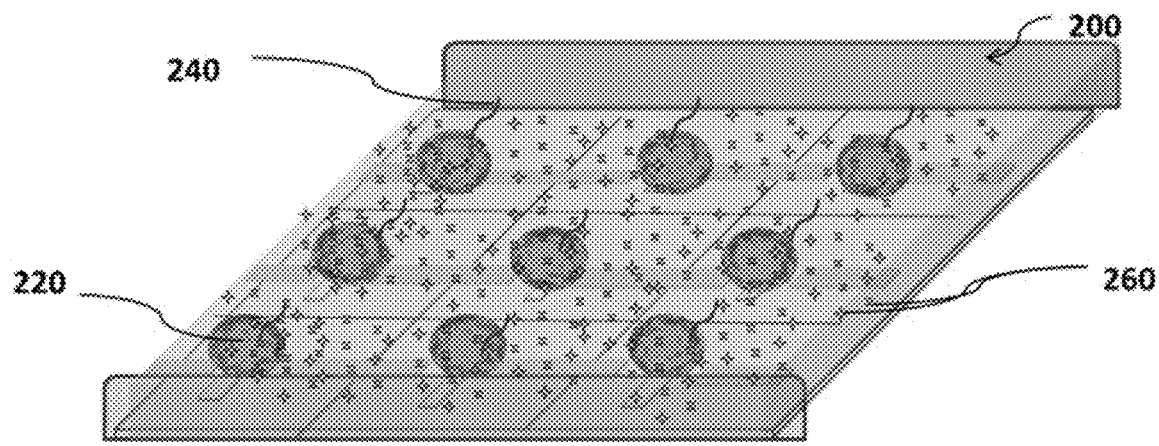

As shown in FIG. 2C, reagents 260 (e.g., polymerase, deoxyribonucleotides (dNTPs), and additional primers) may be simultaneously, previously, or subsequently introduced to the array 200. In some cases, introduction of the reagents 260 may be via flow through microfluidic channels associated with the array 200, such that the reagents 260 are contacted with the magnetic beads 220 via flow. Via magnetic and/or electrostatic forces from the appropriate array elements, the magnetic beads 220 can be maintained in the desired position as reagents 260 make contact with the magnetic beads 220 via flow and/or during subsequent amplification.

Figure 2D:
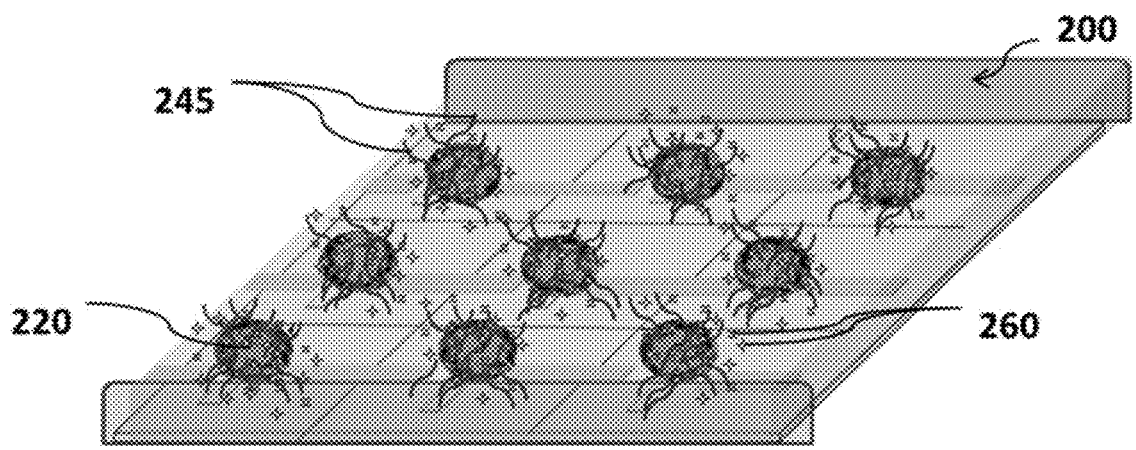

As shown in FIG. 2D, the nucleic acid 240 associated with magnetic beads 220 can be clonally amplified to produce amplified nucleic acid 245 on the surface of the magnetic beads 220. Clonal amplification may be completed using any suitable method including a method described herein such as, PCR, a primer extension reaction, isothermal amplification, or other techniques.

Figure 2E:
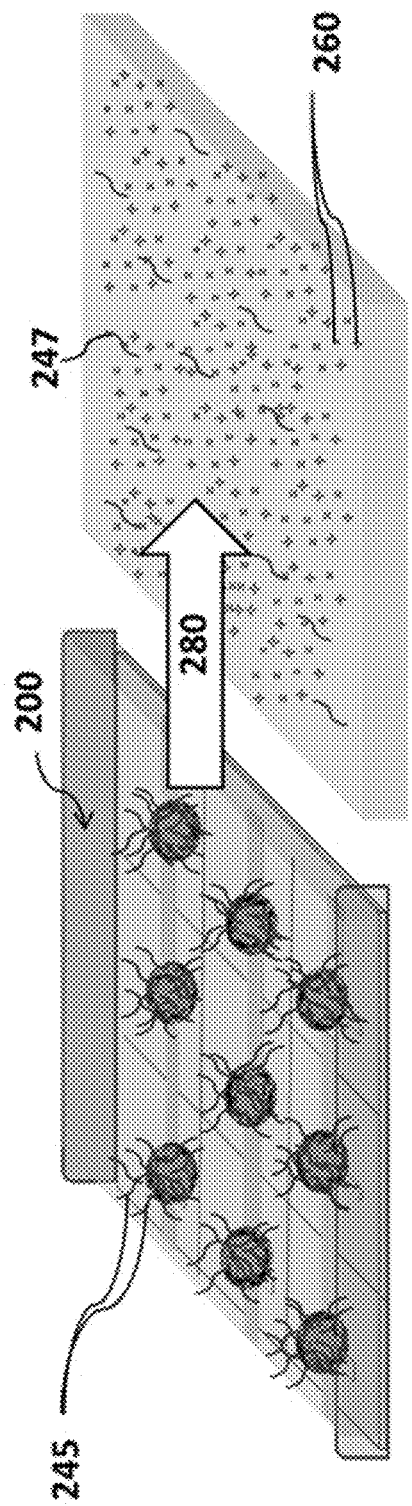

As shown in FIG. 2E, the magnetic beads 220 on the array 200 may be washed 280, removing unbound amplicons 247 and reagents 260 in solution following amplification of nucleic acid 240. The result can be magnetic beads 220 comprising clonal sets of amplified nucleic acid 245 associated with array positions. Washing 280 may be completed by any suitable method, such as, for example, washing with a buffer solution at a flow rate sufficient to remove the unbound amplicons 247 and reagents 260 in solution, but insufficient to detach the magnetic beads 220 from their respective positions on the array.

Figure 2F:
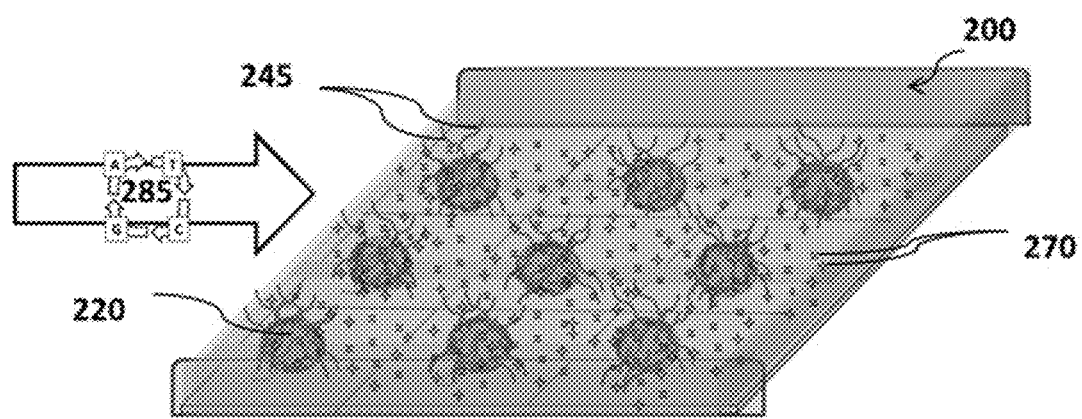

As shown in FIG. 2F, another aliquot of reagents 270 (e.g., polymerase, primers, etc.) and sequential cycles of individual nucleotides 285 may then be contacted (e.g., via flow) with the sensor array, permitting incorporation of the nucleotides into the amplified nucleic acid 245 of magnetic beads 220. Nucleotides may be introduced in individual cycles (e.g., cycle 1=A, cycle 2=T, etc). There may be a wash step with buffer in between each cycle to help reduce the chance of contamination from unincorporated nucleotides. Polymerase used for the sequencing reaction, may be the same type of polymerase that is used for the amplification reaction, or may be a different type of polymerase, and can be introduced prior to or with introduction of the nucleotides. Detection of the incorporated nucleotides during each cycle can be used to sequence the amplified nucleic acid 245, and, thus, the original sample nucleic acid 240. Detection may occur, for example, via one or both of electrodes 205 and 207. In some cases, electrodes 205 and 207 can detect nucleotide incorporation events by measuring local impedance changes of the magnetic beads 220 and/or the amplified nucleic acid (or other nucleic acid) 245 associated with the magnetic beads 220. Such measurement can be made, for example, by directly measuring local impedance change or measuring a signal that is indicative of local impedance change. In some cases, detection of impedance occurs within the Debye length (e.g., Debye layer) of the magnetic beads 220 and/or the amplified nucleic acid 245 associated with the magnetic beads 220. Nucleotide incorporation events may also be measured by directly measuring a local charge change or local conductivity change or a signal that is indicative of one or more of these as described elsewhere herein. Detection of charge change or conductivity change can occur within the Debye length (e.g., Debye layer) of the magnetic beads 220 and/or amplified nucleic acid 245 associated with the magnetic beads 220.

Additional examples of combined amplification and sequencing systems, for example, may be found in PCT Patent Application No. PCT/US2011/054769, PCT Patent Application No. PCT/US2012/039880, PCT Patent Application No. PCT/US2012/067645, PCT Patent Application No. PCT/US2014/027544, and PCT Patent Application No. PCT/US2014/069624, each of which is entirely incorporated herein by reference.

Following the completion of sequencing, beads can be dissociated from the array, the beads can be separated from bound species and either or both of the beads and the array washed. Following washing, the beads and array can be subsequently re-used for another round of amplification and/or sequencing. Dissociation of a bead from the array may be completed, for example, by removal/reversal of a magnetic and/or electric field used to hold the bead in place. In addition or as an alternative, fluid flow and/or other type of field (e.g., external magnetic field, external electric field) capable of exerting forces sufficient for overcoming magnetic and/or electrostatic forces used to hold a bead in place may also be used to dissociate the bead from an array.

While described herein with respect to nucleic acids and nucleic acid sequencing reactions and nucleic acid hybridization, the systems, devices, and methods described herein can be used for a variety of other applications and detection of different biological or biochemical moieties and reactions. Non-limiting examples of such applications include antibody-antigen detection, protein or peptide detection, protein or peptide binding/interaction reactions, cell analysis, drug-discovery or screening, ligand binding detection, pathogen detection, forensic analyses, small molecule detection and reaction detection or other types of analysis. Protein detection may be performed by direct measurement of the reaction, by measurement of a sandwich assay, or by measurement utilizing an aptamer. Sensing in the context of these applications can be performed by coupling species or species that participate in a to-be-monitored reaction to a bead and using sensing methods described herein. In some cases, amplification and/or sensing platforms can be useful in medical applications, including point-of-care diagnostics.

The amplification and/or sensing platforms described herein can be packaged into one or more devices. The device(s) can perform any one or more of the operations of a method, including but not limited to nucleic acid extraction, fragmentation, library preparation, immobilization (e.g., on a bead), amplification, confinement, bead enrichment, sequencing, or data analysis and communication. In some cases, the device(s) are part of a detection system. The system can include a single device of multiple devices. Moreover, such a system can include a single module or may include a plurality of modules. Each device can be for the same biological detection or different biological detection. The devices can be in communication with each other through any suitable type of connectivity, including, for example, wireless connectivity.

Figure 3:
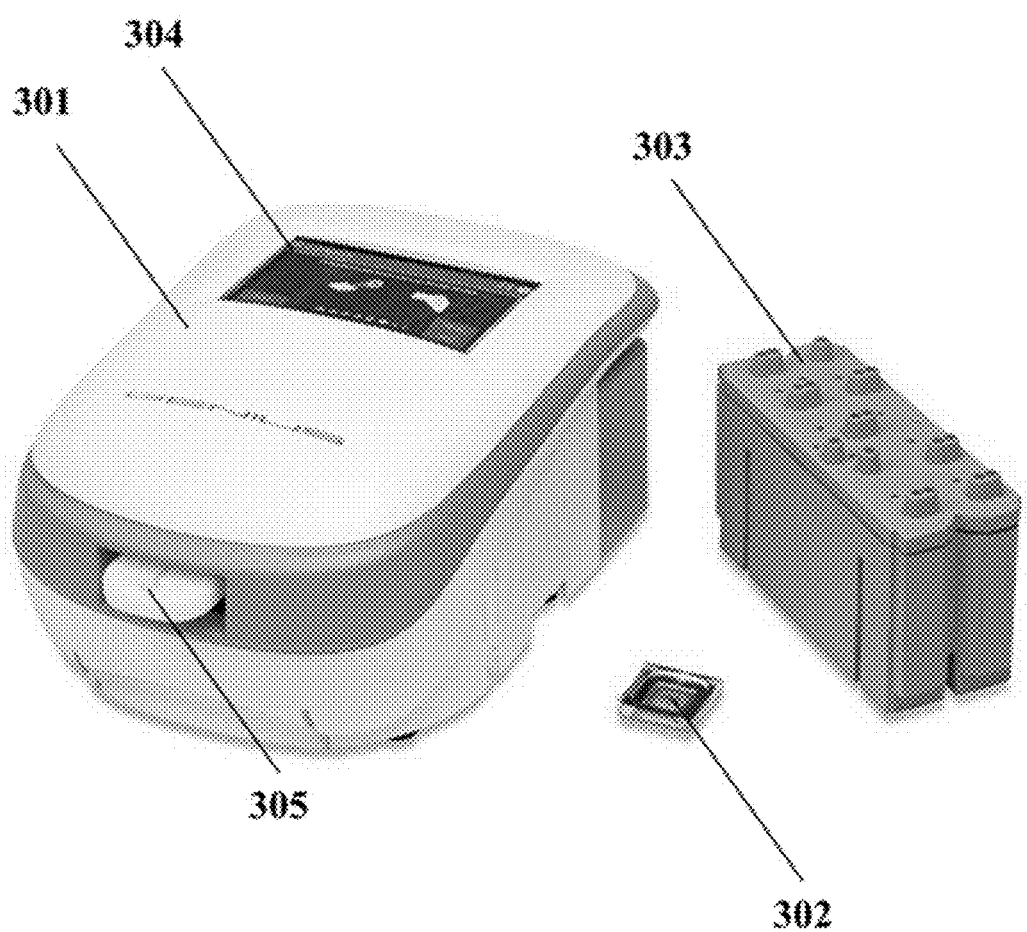
FIG. 3 shows a an example detection device.

An example device is shown in FIG. 3. FIG. 3 shows a detection device 301, a removable chip 302 with a sensing array, and a reagent reservoir 303 that can be inserted into and removed from the biological detection device 301. The chip 302 can be a single-use chip or multi-use chip. The chip can be disposable (e.g., formed of an environmentally friendly material) and/or can be reusable. Moreover, the sensing array can be configured as a sensing array described herein and operated using a sensing method described herein. In some cases, the sensing array also includes electrodes for producing electric fields at sensor array positions. In such cases, nucleic acid amplification and sensing can be performed at a given location of the sensing array.

In some examples, the reagent reservoir 303 includes primers, nucleotides and polymerase enzymes for nucleic acid sequencing. The biological detection device 301 can include a screen 304 that can include a user interface, such as a graphical user interface. The screen 304 can enable a user to operate the device 301, such as for nucleic acid sequencing. The biological detection device 301 can include a port 305 that is configured to accept the removable chip 302. In some examples, upon insertion of the removable chip 302 into the device 301, nucleic acid sequencing can be performed using the sensing array of the chip 302 and the reagents in the reagent reservoir 303. In some cases, the device further comprises one or more fluid flow paths in fluid communication with the sensing array. The fluid flow path can also be in communication with one or more reservoirs comprising one or more reagents for a biological reaction (e.g., nucleic acid sequencing). In some cases, the fluid flow path can provide beads to the sensing array in an emulsion or, alternatively, without an emulsion.

In some situations, the device further comprises a computer processor (or other electronic logic) coupled to the sensing array. The computer processor can be programmed to receive signals from the sensing array that are indicative of a direct electrical signature of the species or reaction associated with the species.

The device can be portable such that it can be readily transported by a user or a machine. For example, the machine may be transportable on a vehicle. In some examples, the vehicle is an automobile, motorcycle, scooter, helicopter, airplane, truck, military vehicle, spacecraft, or robot. In some cases, the sensing device can be provided on a vehicle. The vehicle can be an automobile, motorcycle, scooter, helicopter, airplane, truck, military vehicle, spacecraft, or robot. The weight and footprint of the device can be enclosed in a controlled to aid in rendering the device portable. In some cases, the device may comprise a housing, with a relatively small footprint, in which device components are situated. Moreover, the device may be constructed of materials that result in a relatively low weight of the device. In some examples, the housing has a footprint that is less than or equal to about 250,000 (square millimeters) $mm^2$, 200,000 $mm^2$, 150,000 $mm^2$, 100,000 $mm^2$, 50,000 $mm^2$, 10,000 $mm^2$, 5,000 $mm^2$, or 1,000 $mm^2$ and the device has a weight that is less than or equal to about 200 pounds, 175 pounds, 150 pounds, 125 pounds, 100 pounds, 75 pounds, 50 pounds, 25 pounds or 10 pounds.

Figure 4:
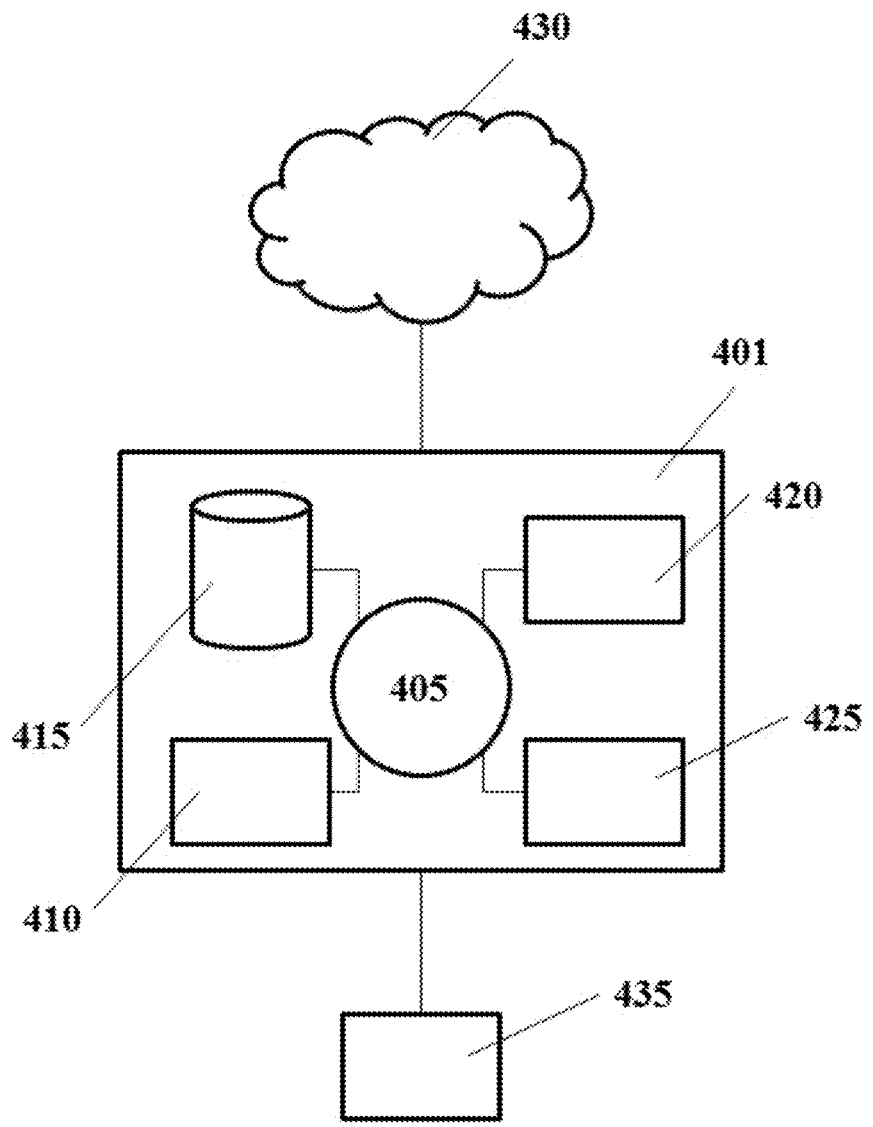
FIG. 4 shows an example computer system that is programmed or otherwise configured to control, regulate or implement devices, systems and methods described herein.

The present disclosure provides computer control systems that are programmed to implement methods of the disclosure. FIG. 4 shows a computer system 401 that is programmed or otherwise configured to operate device components, initiate and execute operation protocols and/or process and analyze data obtained from sensing. The computer system 401 can regulate various aspects of sensing devices, systems and methods of the present disclosure, such as, for example, methods for biological detection. In some embodiments, the computer system 401 can receive signals from a sensor and determine a change in local impedance, local charge and/or local conductivity as described elsewhere herein.

The computer system 401 can be part of or separate from a device or system for biological detection. In some examples, the system 401 is integrated with a device or system for biological detection, such as a nucleic acid sequencing device. For example, the system 401 can be included in a housing that also contains a sensing array, which can be provided via a removable chip.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. Examples of operations performed by the CPU 405 can include fetch, decode, execute, and writeback.

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) for providing, for example, an output or readout of device operation and/or the signals obtained during and/or from sensing. Such readout can include a nucleic acid sequencing readout, such as a sequence of nucleic acid bases that comprise a given nucleic acid sample. Examples of UI's include, without limitation, a graphical user interface (GUI) and web-based user interface. The electronic display 435 can be a computer monitor, or a capacitive or resistive touchscreen.

Methods for Detecting Sensor Occupancy and Mitigating Motion Artifacts

While immobilization of a bead associates the bead with a given position of a sensor array, the bead can still move relative to the electrodes, complicating the collection and analysis of a signal sensed by a sensor. The present disclosure provides sensing methods that can reduce, minimize and/or eliminate sensing complications associated with bead movement at a sensor site. In general, such methods utilize fluid conditions that can reduce, minimize and/or eliminate the deleterious effects and inefficiencies of unoccupied sensor sites, background noise, signal artifacts, and other signal issues associated with bead movement.

The bulk flow of ions is relatively unaffected by the presence of the bead at large distances away from the bead and is proportional to the conductivity of the bulk fluid ($\sigma_b$) in which sensing takes place. However, at short distances, the electric double layer (e.g., within the Debye length) has a surface current that is proportional to the conductivity at the bead surface ($\sigma_s$). The relationship between these conductivities can be represented by the Dukhin number (Du). The Dukhin number is a dimensionless quantity defined as a ratio of the surface conductivity ($\sigma_s$) to the fluid bulk electrical conductivity ($\sigma_b$) multiplied by size of the bead (D): $Du=\sigma_s/(\sigma_b D)$. In the context of sensing, the Dukhin number numerically represents the contribution of the surface conductivity of the bead in overall current measured by the sensor. Signal acquisition may be less sensitive to movements of the bead when the conductivity of the bulk fluid is substantially equal to the conductivity at the bead surface ($\sigma_s \approx (\sigma_b D)$, $Du \approx 1$). Alternatively, or in addition to, signal acquisition may be less sensitive to movement of the bead when the conductivity of the bulk fluid is slightly greater than the conductivity at the surface of the bead ($\sigma_s < (\sigma_b D)$, $Du < 1$).

An aspect of the disclosure provides a method for sequencing a nucleic acid template. The method comprises: (a) contacting a nucleic acid template with a sensing fluid containing a population of nucleotides, where the nucleic acid template is hybridized to a primer and coupled to a bead, which bead is positioned proximate to a sensor in a sensor array, where the sensor comprises a at least two electrodes, and where the sensing fluid has a bulk conductivity and a surface of the bead has a surface conductivity to provide a Dukhin number that is less than about 1; (b) using the sensor to detect a change in conductivity within a Debye layer of the bead upon incorporation of at least one nucleotide of the population of nucleotides into a growing nucleic acid strand, which growing nucleic acid strand is derived from the primer and is complementary to the nucleic acid template; (c) washing the sensor array to remove unincorporated nucleotides of the population of nucleotides from the sensor array; and (d) repeating (a)-(c) to obtain sequence information for the nucleic acid template.

In some embodiments, the bulk conductivity is within about +/−500%, within about +/−300%, within about +/−100%, within about +/−50% or within about +/−10% of the conductivity of the surface of the bead. In some embodiments, the Dukhin number determinable from the conductivities of the sensing fluid and surface of the bead is less than or equal to about 1, less than or equal to about 0.95, less than or equal to about 0.9. less than or equal to about 0.8, less than or equal to about 0.7, less than or equal to about 0.6, less than or equal to about 0.5, less than or equal to about 0.4, less than or equal to about 0.3, less than or equal to about 0.2, less than or equal to about 0.1, or less. In some embodiments, the Dukhin number determinable from the conductivities of the sensing fluid and surface of the bead is greater than or equal to about 0.1, greater than or equal to about 0.2, greater than or equal to about 0.3, greater than or equal to about 0.4, greater than or about equal to 0.5, greater than or equal to about 0.6, greater than or equal to about 0.7, greater than or equal to about 0.8, greater than or about equal to about 0.9, greater than or about equal to about 1, or greater. In some embodiments, the Dukhin number determinable from the conductivities of the sensing fluid and surface of the bead is between about 0.08 and 1, between about 0.1 and 1, between about 0.2 and 1, between about 0.3 and 1, between about 0.4 and 1, between about 0.5 and 1, between about 0.6 and 1, between about 0.7 and 1, between about 0.8 and 1, or between about 0.9 and 1. The sensing fluid may contain reaction components necessary to sequence a nucleic acid template. The reaction components may include one or more of polymerases or polymerizing enzymes, buffers, salts, co-factors, adenosine triphosphate, and crowding agents. The nucleotide may be incorporated with the aid of the polymerase or polymerizing enzyme. A given electrode of a sensor may be exposed to the sensing fluid. The electrodes may be within a Debye layer of the bead or within a Debye layer of the nucleic acid molecule to be sequenced. The sensor may further detect changes in impedance within the Debye layer of the bead upon incorporation of a nucleotide. The change in conductivity and the change in impedance may be detected transiently or during steady state conditions.

The sensing fluid may include one or more of magnesium chloride ($MgCl_2$) magnesium sulfate ($MgSO_4$), sodium chloride (NaCl), and potassium chloride (KCl), or any other buffer comprising the desired conductivity. The sensing fluid may have a solute concentration less than about 100 millimolar (mM), less than about 50 mM, less than about 25 mM, less than about 15 mM, less than about 10 mM, less than about 8 mM, less than about 6 mM, less than about 4 mM, less than about 2 mM, less than about 1 mM, less than about 0.8 mM, less than about 0.6 mM, less than about 0.4 mM, less than about 0.2 mM, less than about 0.1 mM, or less. The sensing fluid may have a solute concentration between about 0.1 mM and 8 mM, between about 0.15 mM and 6 mM, between about 0.2 mM and 4 mM, between about 0.5 mM and 2 mM.

In another aspect, the disclosure provides a method for determining bead occupancy at sites of a sensor array. The method comprises: (a) contacting a sensor array with a plurality of beads, where the sensor array comprises a plurality of sensors each having a at least two electrodes, to provide a given bead of the plurality of beads at a given position in proximity to an individual sensor of the plurality of sensors; (b) contacting the sensor array with a probe fluid that has a bulk conductivity that is at least about 50 times greater than or 50 times less than a conductivity associated with a surface of the given bead; (c) using the individual sensor to detect signals that are indicative of a presence of the given bead in proximity to the sensor; and (d) identifying the given position of the sensor array as occupied by the given bead.

The sensor array may be used to detect the presence of a bead within sensing proximity of an individual sensor. Detecting a bead within proximity of a sensor may include contacting the sensing array with a probe fluid. The probe fluid may have a bulk conductivity that is at least about 50 times greater than or 50 times less than the conductivity associated with the surface of the bead. The sensor may be used to detect signals that are indicative of a presence of the bead in proximity to the sensor. In some embodiments, the conductivity associated with the probe fluid is at least about 100 times greater, at least about 500 times greater, at least about 1000 times greater, at least about 5000 times greater, or more than the conductivity associated with the surface of the bead. In some embodiments, the conductivity associated with the probe fluid is at least about 100 times less, at least about 500 times less, at least about 1000 times less, at least about 5000 times less, or less than the conductivity associated with the surface of the bead.

The probe fluid may have a bulk conductivity that is at least about 50 times great than or 50 times less than the conductivity of a Debye layer of the given bead. The conductivity associated with the probe fluid may be at least about 100 times greater, at least about 500 times greater, at least about 1000 times greater, at least about 5000 times greater, or more than the conductivity of a Debye layer of the given bead. The conductivity associated with the probe fluid may be at least about 100 times less, at least about 500 times less, at least about 1000 times less, at least about 5000 times less, or less than the conductivity of a Debye layer of the given bead.

The probe fluid can be any suitable buffer that has a conductivity that is different or substantially different from the conductivity at the bead surface, with non-limiting examples that include magnesium chloride ($MgCl_2$), magnesium sulfate ($MgSO_4$), sodium chloride (NaCl), potassium chloride (KCl) buffer, or any other buffer. Moreover, the probe fluid can have any suitable concentration of solutes, such that the conductivity of the fluid is different or substantially different from the conductivity at the bead surface. For example, the concentration of solutes in the fluid may be from about 0.01 mM (millimolar) to about 1 molar (M), 0.01 mM to about 500 mM, 0.01 mM to about 50 mM, 0.01 mM to about 25 mM, 0.01 mM to about 10 mM, 0.1 mM to about 10 mM, 0.1 mM to about 8 mM, 0.1 mM to about 6 mM, 0.1 to about 4 mM, 0.1 to about 2 mM or 0.1 to about 1 mM.

The Dukhin number may be determinable from the conductivity of the probe fluid and the conductivity of the surface of the bead and may be less than 1, greater than 1, substantially less than 1, or substantially greater than 1. The bulk conductivity may be within about +/−500% of a conductivity of the Debye layer. Contacting the sensor array with a probe fluid may permit measurement of the presence or absence of a bead in proximity to a sensor location. The bead may be coupled to a nucleic acid molecule. Detecting the presence of a bead in proximity to a sensor may be performed prior to or during detection of the incorporation of nucleotides. Sensors without a bead within sensing proximity may be excluded from sensing and may not be used to detect a sequence of a nucleic acid molecule. Alternatively, or in addition to, sensors with a bead within sensing proximity may be used to detect a sequence of a nucleic acid molecule. The signals to detect the presence of a bead within sensing proximity to a sensor may comprise an electrical current. The signals that comprise an electrical current may include conductivity or impedance signals.

Figure 5:
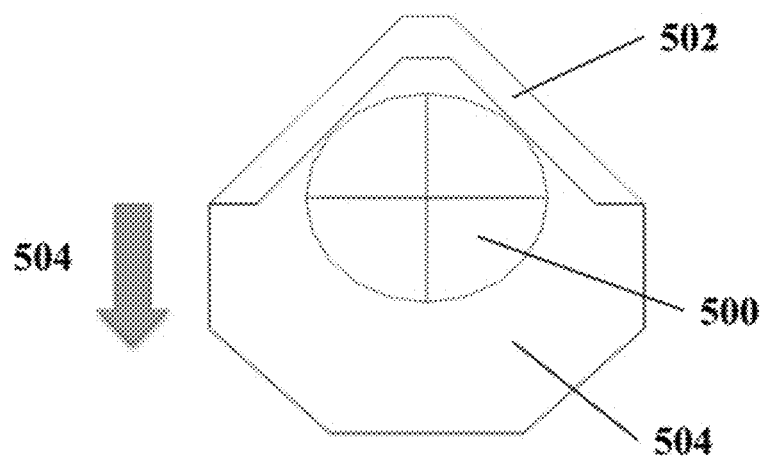
FIG. 5 schematically depicts an example bead-sensor structural configuration.

An example sensor and bead configuration is schematically depicted in FIG. 5. With reference to FIG. 5, a bead 500 is located in proximity to a first electrode 502 and a second electrode 504. The bead 500 can move (in any direction) by a distance 504. Movement can be due to various factors, including, for example, Brownian motion, fluid flow, diffusion of vibration of the device, or a combination thereof. In some cases, the bead 500 is continually moving during detection of signal, complicating signal acquisition and analysis with higher background noise and lower signal to noise ratio.

Figure 6:
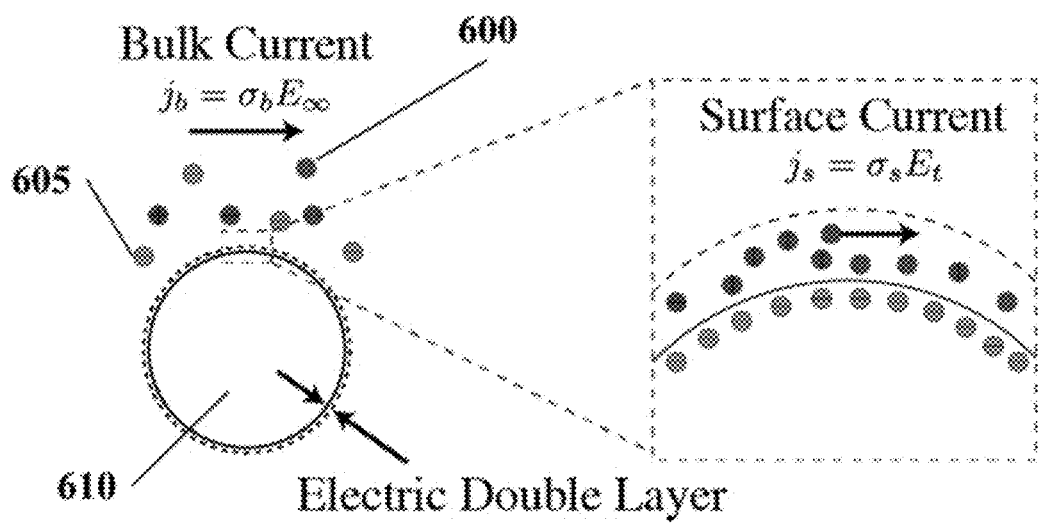
FIG. 6 schematically depicts an example of conductivity at a bead surface and in a bulk fluid adjacent to the bead surface.

The composition and concentration of species in a fluid (e.g., buffer) in which sensing takes place can affect the prominence of sensing issues associated with bead movement. An example of the charge environment in proximity is schematically depicted in FIG. 6. With reference to FIG. 6, a buffer comprising positive ions 600 and negative ions 605 can flow and/or conduct current in proximity to a bead 610. Signal acquisition can be less sensitive to movements of the bead when the conductivity of the bulk fluid is substantially equal or equal to the conductivity at the bead surface ($\sigma_s=$ or $\approx (\sigma_b D)$, Du= or $\approx 1$). For example, the conductivity of the fluid in which sensing takes places may be within about plus or minus (+/−) 500%, within about +/−450%, within about +/−400%, within about +/−350%, within about +/−300%, within about +/−250%, within about +/−200%, within about +/−150%, within about +/−100%, within about +/−50%, within about +/−40%, within about +/−30%, within about +/−20%, within about +/−10%, within about +/−5%, or within about +/−1%, of the conductivity at the bead surface. In some examples, the conductivity of the bead at its surface is within about +/−300%, within about +/−250%, within about +/−200%, within about +/−150%, within about +/−125%, within about +/−100%, within about +/−95%, within about +/−90%, within about +/−85%, within about +/−80%, within about +/−75%, within about +/−70%, within about +/−65%, within about +/−60%, within about +/−55%, within about +/−50%, within about +/−45%, within about +/−40%, within about +/−35%, within about +/−30%, or within about +/−25% of the conductivity of the fluid.

The fluid in which sensing occurs can be any suitable buffer that has a conductivity that is substantially equal to or equal to the conductivity at the bead surface, with non-limiting examples that include magnesium chloride ($MgCl_2$), magnesium sulfate ($MgSO_4$), sodium chloride (NaCl) and potassium chloride (KCl) buffer. Moreover, the fluid in which sensing occurs can have any suitable concentration of solutes, such that the conductivity of the fluid is equal to or substantially equal to the conductivity at the bead surface. For example, the concentration of solutes in the fluid may be from about 0.01 mM (millimolar) to about 1 molar (M), 01 mM to about 500 mM, 0.01 mM to about 50 mM, 0.01 mM to about 25 mM, 0.01 mM to about 10 mM, 0.1 mM to about 10 mM, 0.1 mM to about 8 mM, 0.1 mM to about 6 mM, 0.1 to about 4 mM, 0.1 to about 2 mM or 0.1 to about 1 mM.

Figure 7:
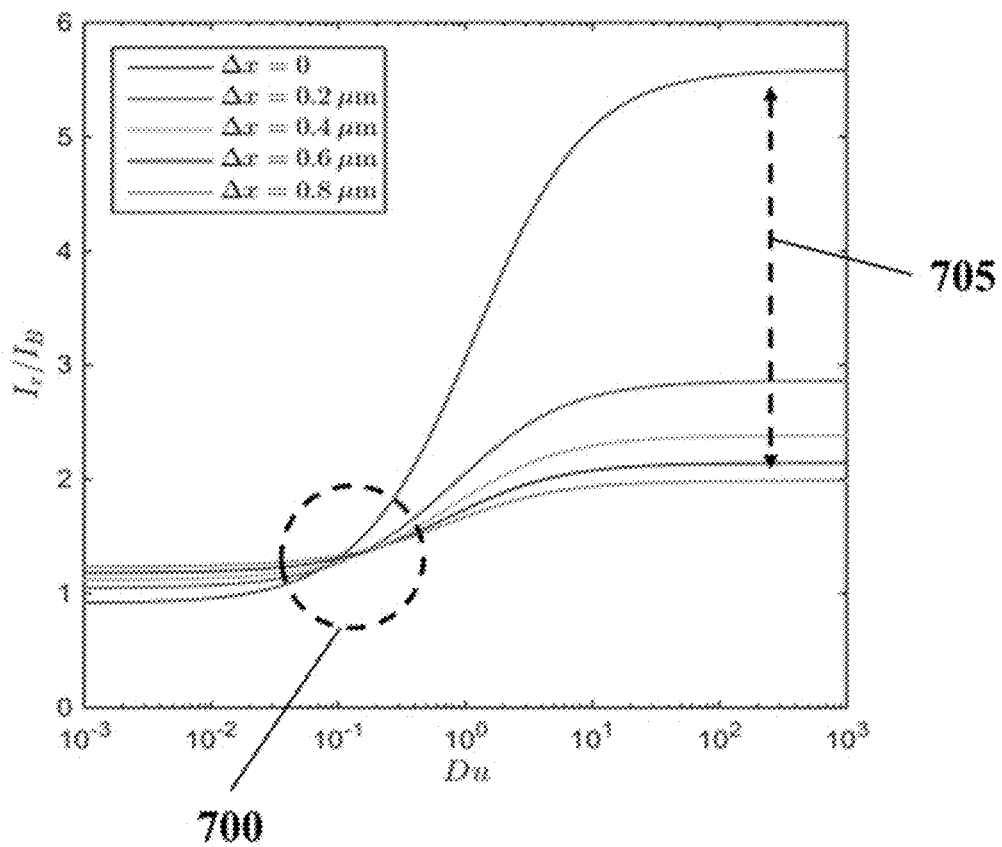
FIG. 7 graphically depicts an example of the effect of buffer concentration on the sensitivity of observed current to movement of a bead associated with a sensor.

Data obtained from example sensing experiments evaluating the effect of Du on observed signal with an electrode pair is graphically depicted in FIG. 7. With reference to FIG. 7, the vertical axis is dimensionless current ($I_r/I_b$) and the horizontal axis is a Du, with a relatively high concentration buffer represented to the left of the horizontal axis (e.g., toward $10^{-3}$) and a relatively low concentration buffer to the right (e.g., toward $10^3$) of the horizontal axis. Each line on the chart represents a different distance by which a bead has moved relative to the sensor (ax) and ranges from 0 to about 0.8 micrometers (μm). Note that in the region where the conductivities are between Du=0.1 and Du≈1 (i.e., approximately equal), sensing is least sensitive to bead movement (e.g., all values of Δx give approximately the same current signal). In other words, the sensor does not detect a significant change in current when the bead moves relative to the sensor electrodes. Conversely, also shown in FIG. 7, at high Du numbers, the signal change 705 is relatively large. Such difference in signal may be used to detect beads at sensor positions as described elsewhere herein.

Additionally, differences in bulk conductivity of a fluid in which sensing takes place and the conductivity of a surface of a bead can be exploited to identify sensor array sites that are occupied with a bead. Exposure of a sensor array to a probe fluid for which Du is > or >>1 or Du< or <<1 can result in relatively large signal changes that can be detected and interpreted to indicate the presence of a bead at a given sensor. Identification of sensors occupied with beads can reduce the amount of data collected, by excluding data acquisition from sensors that are not associated with a bead (and, thus, an analyte). Reduced data acquisition can improve the speed and decrease the complexity of data processing. Moreover, such differences can be used to determine if a bead has been lost or gained from a particular sensor location during or after sensing. Indeed, a sensor can be exposed to a fluid for which Du> or >>1 or Du< or <<1 at any point before or after sensing in order to determine the bead occupancy of sensor array sites. For sensing, the fluid can be replaced with one in which Du= or 1 or 0.1<Du≤1 in order to minimize signal acquisition issues as is described elsewhere herein.

Where a probe fluid is used to evaluated bead occupancy at various sites of a sensor array, the conductivity at a bead surface can be any conductivity sufficiently different (e.g., greater or less) from the conductivity of the probe fluid such that an observable signal change is generated at bead-occupied sensor sites. In some cases, the conductivity of probe fluid is at least about 10 times, at least about 50 times, at least about 100 times, at least about 500 times, at least about 1000 times, at least about 5000 times, at least about 10000 times, at least about 50000 times, or at least about 100000 time greater than the conductivity of the bead surface. In some instances, the conductivity of the probe fluid is at least about 10 times, at least about 50 times, at least about 100 times, at least about 500 times, at least about 1000 times, at least about 5000 times, at least about 10000 times, at least about 50000 times, or at least about 100000 time less than the conductivity of the bead surface.

Moreover, as stated previously, the Du determinable from the conductivities of the probe fluid and surface of the bead can be any suitable number, such that that Du is sufficiently greater or less than 1 such that a sufficient signal change can be observed. For example, the Du determinable from the conductivities of the probe fluid and surface of the bead may be at least about 0.0001, at least about 0.001, at least about 0.01, at least about 0.1, at least about 1, at least about 10, at least about 100, at least about 1000 or at least about 10000 or higher. In other examples, the Du determinable from the conductivities of the probe fluid a surface of the bead may be less than about 10000, less than about 1000, less than about 100, less than about 10, less than about 1, less than about 0.1, less than about 0.01, less than about 0.001 or less. In some examples, the Du determinable from the conductivities of the probe fluid and surface of the bead may be from about 0.001 to about 0.9, from about 0.01 to about 0.9, from about 1.1 to about 10000 from about 10 to about 10000, or from about 1.1 to about 1000, from about 10 to about 1000, or from about 100 to about 1000.

The probe fluid can be any suitable buffer that has a conductivity that is different or substantially different from the conductivity at the bead surface, with non-limiting examples that include magnesium chloride ($MgCl_2$), magnesium sulfate ($MgSO_4$), sodium chloride (NaCl) and potassium chloride (KCl) buffer. Moreover, the probe fluid can have any suitable concentration of solutes, such that the conductivity of the fluid is different or substantially different from the conductivity at the bead surface. For example, the concentration of solutes in the fluid may be from about 0.01 mM (millimolar) to about 1 molar (M), 0.01 mM to about 500 mM, 0.01 mM to about 50 mM, 0.01 mM to about 25 mM, 0.01 mM to about 10 mM, 0.1 mM to about 10 mM, 0.1 mM to about 8 mM, 0.1 mM to about 6 mM, 0.1 to about 4 mM, 0.1 to about 2 mM or 0.1 to about 1 mM.

Experimental data obtained from an example sensor occupancy experiment is shown in FIG. 8. FIG. 8 shows an image 800 of a 30×30 sensor array, with various sensor sites occupied with beads (white circles of 800). FIG. 8 also shows a signal output map 805 generated by exposing the sensor array to a probe fluid having sufficient conductivity difference from the conductivity at a bead surface bead such that a signal change (e.g., black areas of 805) is observed at occupied sites. Conversely, no signal change (e.g., white areas of 805) is observed in areas unoccupied by a bead. Correspondence between visually occupied and non-occupied sites in photograph 800 and sites indicated as occupied on output map 805 is good, validating the method.

In another example, the feasibility of discriminating bead-occupied sensors from unoccupied sensors in a probe fluid (e.g., Du> or >>1 or Du< or <<1) and sensing fluid (e.g., Du= or ≈1) were evaluated in an example experiment exposing a sensor array to each fluid. The results of the experiment are graphically depicted in FIG. 9. As shown in FIG. 9, the measured signal in the probe fluid distinguished occupied sites from those unoccupied, indicated by a separation of signal in plot 905 of FIG. 9. Conversely, measured signal in the sensing fluid was not able to distinguish occupied sensor sites from those unoccupied, indicated by a lack of signal separation in plot 900 of FIG. 9.

Methods for Processing Nucleic Acid Samples

In an aspect, the present disclosure provides a method for processing a nucleic acid sample. The method may comprise providing a mixture comprising a first set of droplets and a second set of droplets. The first droplet of the first set of droplets may comprise (i) a bead, (ii) a recombinase, (iii) a polymerizing enzyme, and (iv) a nucleic acid molecule from the nucleic acid sample. The second droplet of the second set of droplets may comprise an activating agent that increases a rate at which the recombinase processes the nucleic acid molecule to permit the primer to hybridize to the nucleic acid molecule to conduct a primer extension reaction in the presence of the polymerizing enzyme, to generate an amplification product(s) from the nucleic acid molecule.

The first droplet may be merged with the second droplet in the mixture to generate a third droplet as part of a third set of droplets. The third droplet may comprise the bead having coupled thereto the nucleic acid molecule, recombinase, primer and polymerizing enzyme.

The primer extension reaction may be conducted to generate the amplification product(s) from the nucleic acid molecule in the third droplet. For example, the primer extension reaction may include conducting isothermal recombinase polymerase amplification (RPA) or a polymerase extension reaction (PCR).

Figure 10:
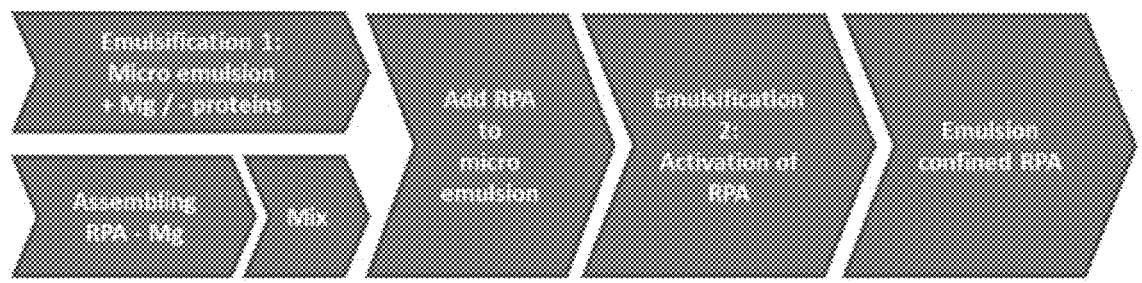
FIG. 10 schematically illustrates a method for processing a nucleic acid sample.

FIG. 10 schematically illustrates an example of a method for processing a nucleic acid sample. A mixture comprising a first set of droplets and a second set of droplets may be merged to form a third set of droplets. Formation of the third set of droplets may activate the primer extension reaction within the confinement of the third droplet.

The mixture comprising the first and second set of droplets may further comprise an oil phase, such as mineral oil, and an emulsifier, such as Tegosoft DEC or ABIL WE09.

The droplets may contain additional components. For example, the first set of droplets may contain buffer, salts, crowding agents, dNTPs, and primers. The second set of droplets, along with containing buffer, salts, crowding agents, dNTPs, and primers, may also contain ATP, recombinase loading enzyme, single-stranded DNA-binding protein, and an ATP-regenerating unit (e.g., ATP-regenerating compound).

In some embodiments, the activating agent contained within the second droplet may be a magnesium salt. Example magnesium salts include, but are not limited to, magnesium chloride and magnesium acetate.

Formation of the third droplet may be achieved quickly, on the order of at most about 10 minutes, at most about 5 minutes, at most about 1 minute, at most about 30 seconds, at most about 10 seconds, at most about 5 seconds, or less, through low speed agitation. This agitation may include stirring and/or shaking.

Figure 11A:
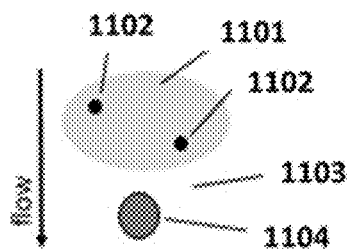
FIGS. 11A-11F schematically illustrate obstacle based emulsification and arrays thereof.
Figure 11B:
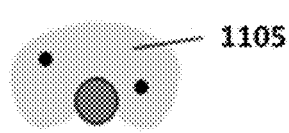
Figure 11C:
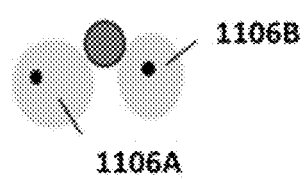
Figure 11D:
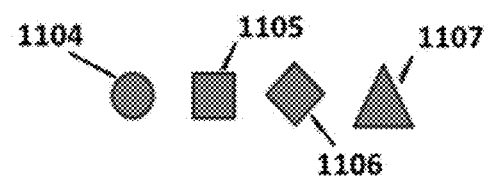
Figure 11E:
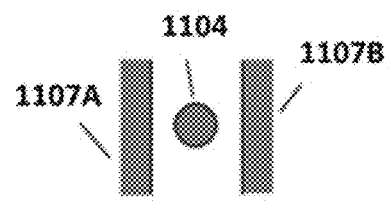
Figure 11F:
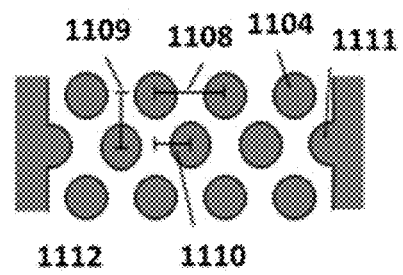

In some cases, the third set of droplets is directed through a set of obstacles to control the shape or size of each of the third set of droplets. The obstacles may be pillars, for example, and may be comprised of a variety of shapes and sizes arranged in a variety of structural patterns. The shape of the obstacles may include triangles, squares, diamonds, and/or circles. The structural patterns may include such arrangements as comb-like structures. The obstacles and structural pattern may be formed on an elastic or inelastic substrate. The obstacles and structural pattern may be formed by photolithography, stamping, etching, machining, molding, or any other fabrication approach. The size and shape of the third set of droplets may further be controlled by the flowrate and pressure used to direct the droplets through the set of obstacles. The flowrate and pressure may be controlled by a pressurizing reservoir or a membrane pump. Examples of obstacles and uses of such obstacles are schematically illustrated in FIGS. 11A-11F. FIG. 11A illustrates the aqueous phase 1101 in proximity to an obstacle 1104. The aqueous phase 1101 may contain primer bound beads 1102 and may be surrounded by a continuous oil phase 1103. Flow may transport the aqueous phase droplet towards the obstacle, which may cause the droplet to deform and elongate 1105 due to shear forces, as shown in FIG. 11B. FIG. 11C shows the droplet after it has passed an example obstacle and split into two daughter droplets 1106A and 1106B. The daughter droplets 1106A and 1106B may each contain a single primer bound bead 1102. The obstacles may have any arbitrary shape, as seen in FIG. 11D, such as round 1104, square 1105, diamond 1106, and triangle 1107. Furthermore, obstacles may be placed into a flow cell, see FIG. 11E. The flow cell may be formed by two sidewalls 1107A and 1107B and the obstacles may form a structural array 1112 pattern between the sidewalls 1107A and 1107B. The structural array, shown in FIG. 11F, may be defined by the spacing and number of obstacles in a row 1108. Additional rows may be defined by column offset 1109 and row offset 1110. The boundary of the array may also contain partial obstacles 1111.

Figure 12A:
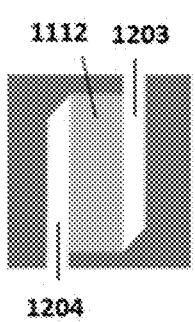
FIGS. 12A-12E schematically illustrate integration of an obstacle array into a microfluidic fluidic device for emulsion generation.
Figure 12C:
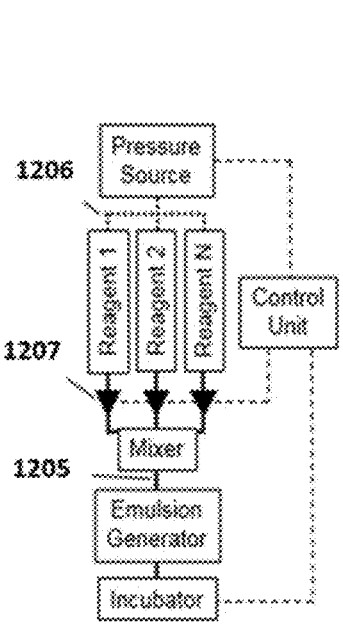
Figure 12D:
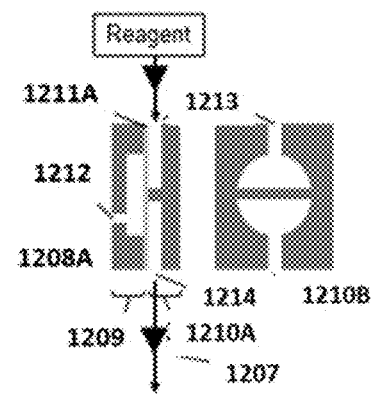
Figure 12B:
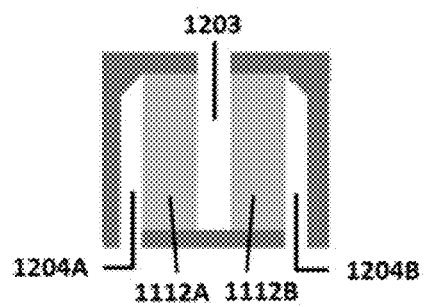
Figure 12E:
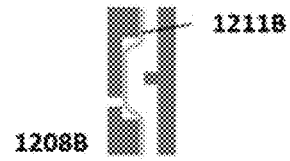

The flow cell containing the obstacle array may further be integrated into a microfluidic fluidic device for emulsion generation. Examples of the integration of an obstacle array into a microfluidic fluidic device for emulsion generation is schematically illustrated in FIGS. 12A-12E. FIG. 12A shows the obstacle array 1112 placed into the microfluidic emulsion generator device 1201 with an inlet channel 1203 and an outlet channel 1204. FIG. 12B shows two multiplexed arrays. Multiplexing of arrays may be implemented with, for example, a single inlet channel 1203, two arrays 1112A and 1112B, and outlet channels 1204A and 1204B. FIG. 12C shows an example device for on-chip amplification. An on-chip amplification reaction may be performed by connecting reagent chambers, mixer, emulsion generator, and incubator by channels carrying the fluids 1205. Transport of fluidics may be achieved by an external pressure source and pressure lines 1206 connected to reagent compartments as well as valves 1207. Valves and pressure may be controlled by a control unit. Alternatively to pressurizing reagent chambers, on-chip membrane valves and pumps, shown in FIGS. 12D and 12E, may be used to move liquid. The closed version of the membrane pump 1208A may consist of a pneumatic layer 1209 with a vacuum and/or pressure connector 1212, a membrane 1211A, and a hydraulic layer 1210A and 1210B. Fluid may enter the pump using an inlet 1213 and may exit the pump via an outlet 1214. The membrane pump 1208B may be opened by applying vacuum to the pneumatic layer to deform the membrane 1211B and liquid may enter the pump compartment. Applying pressure to the pneumatic layer may close the pump and liquid may flow out of the pump compartment. Surrounding valves 1207, which may be made out of a small version of the membrane pump, may direct the flow of liquid.

Figure 13:
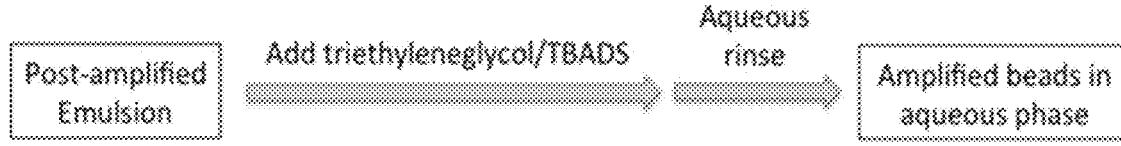
FIG. 13 schematically illustrates the breaking and deactivating of an emulsion in two steps.

The third set of droplets may be disrupted. The result of disrupting the third set of droplets may be the formation of a homogenous solution. Disruption may be performed through the addition of a disrupting mixture. As an alternative, this may be performed by agitating the emulsion. The third set of droplets may be disrupted after the primer extension reaction has been conducted. An example of the breaking of an emulsion is schematically illustrated in FIG. 13.

In some cases, the disrupting mixture may be comprised of a deactivating agent dissolved in an emulsion disruptor. A variety of emulsion disrupters may be used including polyethylene glycol like compounds, such as triethylene glycol. A variety of deactivating agents may also be used, such as tetraalkyl ammonium dodecylsulfate compounds. An example of an effective deactivating agent is tetrabutylammonium dodecylsulfate.

In some embodiments, beads coupled to amplification product(s) may be captured by a capture bead to form a multi-bead complex. The multi-bead complex may be appreciably larger than a non-complexed bead. The multi-bead complex may be about 2 time larger, about 4 times larger, about 6 times larger, about 8 times larger, about 10 times larger, about 15 times larger, about 25 times larger, about 50 times larger, about 100 times larger, or more than the non-complexed bead. The capture bead used may be chosen such that it exclusively binds to beads coupled to amplification product(s). The capture bead may include any moieties that reversibly bind to the beads, such as through association/disassociations interactions or hybridization events. Formation of a multi-bead complex may enable separation and enrichment of beads coupled to amplification product(s). Enrichment may be performed by size selection. Alternatively, magnetic capture beads may be used to enable enrichment to be performed using a magnet.

In some cases, size selection may be performed by directing beads through a set of obstacles, wherein the non-complexed beads can pass through the set of obstacles and the multi-bead complex cannot. The obstacles may be pillars, for example, and may be comprised of a variety of shapes and sizes arranged in a variety of structural patterns. The size selection cutoff may be controlled by obstacle shape, spacing, or structure. The shape of the obstacles may include triangles, squares, diamonds, and/or circles. The structural patterns may include such arrangements as comb-like structures. The size selection may further be controlled by the obstacle shape, the obstacle spacing, and/or the obstacle structure.

Obstacles may be used to sort beads. Examples of obstacle based bead sorting are schematically illustrated in FIGS. 14A-14D. Due to the Poisson distribution, a subset of beads may be coupled to amplification product(s) 1401 while a large portion of beads may not be coupled to amplification product(s) 1402. Amplified beads may be tagged exclusively and may be captured by larger capture beads 1403, forming multi-bead complexes 1404, as shown in FIG. 14A. Separation of the multi-bead complexes from the non-complexed beads may be achieved using a microfluidic enrichment module containing an obstacle array 1405. An example enrichment module is shown in FIG. 14B. A mixture a beads may enter the module through an inlet channel 1406A. The Obstacle array 1104 may create a filter-like structure, enabling the non-complexed beads to pass, while the large multi-bead complex may be rejected. The channel outlet 1408 may show an enrichment of multi-bead complexes and the channel outlet 1407A may exclusively contain non-complexed beads. The enriched portion may be recycled to inlet 1406A. Alternatively, a different implementation, shown in FIG. 14C, may be used that comprises a sole exit channel 1407B. In this implementation, the captured multi-bead complexes may remain in the obstacle entry channel 1406B and elusion may require reversal of the flow. A further implementation of this concept, shown in FIG. 14D, may contain a sheath flow 1411 to increase the effectiveness of the enrichment.

Figure 15:
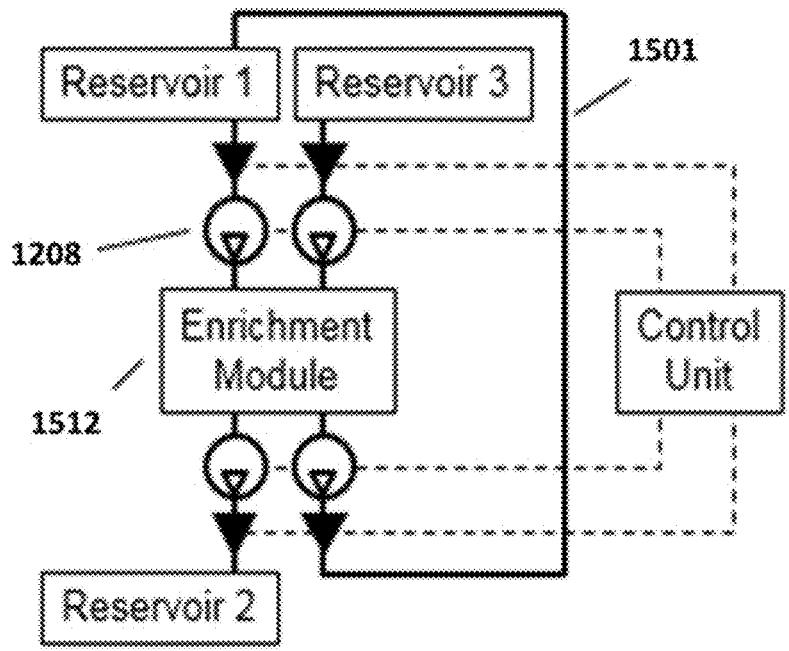
FIG. 15 schematically illustrates integration of an enrichment module into a microfluidic fluidic device.

An example of integration of the enrichment module 1512 integrated into a microfluidic device is schematically illustrated in FIG. 15. The sheath flow based enrichment module maybe connected to four membrane pumps 1208, which may in turn be connected to valves. Reservoir 1 may contain a bead mixture comprising multi-bead complexes and non-complexed beads. Reservoir 3 may contain a buffered aqueous solution. The membrane pumps may enable flow from reservoir 1 and 3 through the enrichment module. Reservoir 2 may collect the fraction of non-complexed beads after the bead mixture has passed through the enrichment module. The portion of the bead mixture containing the multi-bead complexes may be recycled to reservoir 1 via a connector channel 1501, enabling additional passes through the enrichment module. Additional passes through the enrichment module may increase the enrichment levels to achieve a sufficiently high ration of multi-bead complexes to non-complexed beads.

Figure 16A:
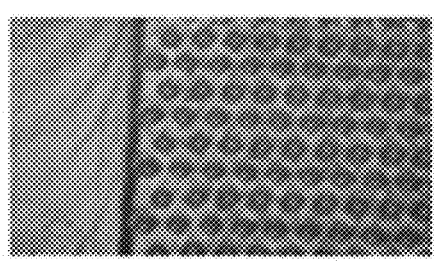
FIGS. 16A-16D schematically illustrate emulsification using obstacle arrays.
Figure 16C:
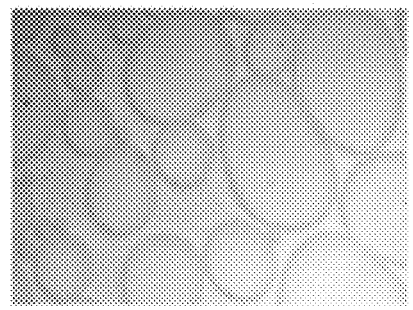
Figure 16B:
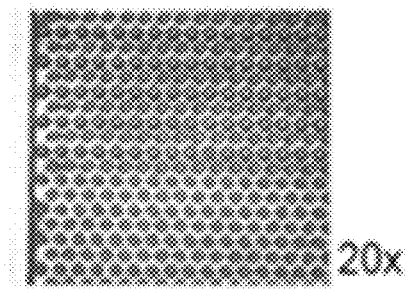
Figure 16D:
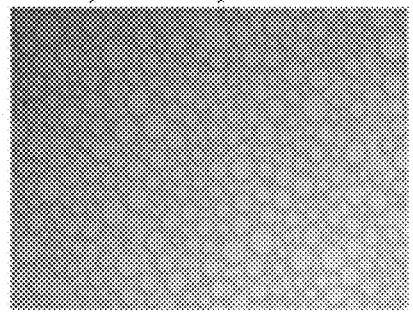

A crude emulsion that has been directed through an array of obstacles is shown in FIGS. 16A-16D. FIGS. 16A and 16B show example arrays of round obstacles arranged in a comb-like or hexagonally close packed arrangement. FIG. 16C shows a crude emulsion prior to being directed through an array of obstacles. The crude emulsion has droplet sizes that are large and non-uniform. The large droplets may be prone to interaction, recombining, and forming larger droplets. FIG. 16D shows an emulsion after being directed through an array of obstacles. The droplet size in after being directed through the array of obstacles are smaller and more uniform than the crude emulsion. The smaller, more uniform droplets may be more stable than the droplets of the crude emulsion.

Methods for Bead-Free Nucleic Acid Sequencing

The present disclosure provides methods and systems for bead-free nucleic acid sequencing. This may involve using nucleic acid amplification reaction, such as invader amplification, as described in, for example, U.S. Patent Publication No. 2015/0344943, each of which is entirely incorporated herein by reference.

In an aspect, the present disclosure provides a method for processing a nucleic acid sample. The method may comprise activating a sensor comprising a support that may comprise at least two electrodes and a polymeric material adjacent to the support. The electrodes may be exposed to a solution comprising the polymeric material. The polymeric material may retain the nucleic acid molecules during a sequencing reaction. The sequencing reaction may yield signals indicative of individual bases of the nucleic acid molecule. During the sequencing reaction, the electrodes of the sensor may be used to detect the signals indicative of individual bases of the nucleic acid molecule. Signals may be measured transiently or during steady state conditions.

The method may comprise performing a sequencing reaction which may yield signals indicative of impedance changes that may accompany the incorporation of nucleotides into the nucleic acid molecule. During the sequencing reaction, the electrodes of the sensor may be used to detect impedance signals indicative of nucleotide incorporation into the nucleic acid molecule.

In another aspect, the present disclosure provides a system for processing a nucleic acid sample. The system may comprise a support comprising at least two electrodes and a polymeric material adjacent to the support. The electrodes may be exposed to a solution comprising the polymeric material and the polymeric material may retain the nucleic acid molecule during a sequencing reaction. The sequencing reaction may yield signals indicative of individual bases of the nucleic acid molecule. The sensor may be coupled to one or more computer processors that may operate the sensor. The computer processors may be programmed to subject the nucleic acid molecule to the sequencing reaction and to use the electrodes of the sensor to detect signals indicative of individual bases of the nucleic acid molecule. The computer processor may also be programmed to use the detected signals to generate a sequence of the nucleic acid molecule. The system may be configured to measure transient signals, steady state signals, or both transient and steady state signals.

The system may comprise a sequencing reaction which may yield signals indicative of impedance changes accompanying incorporation of nucleotides into the nucleic acid molecule. The sensor may be coupled to one or more computer processors that operate the sensor and may be programmed to use the electrodes to detect signals indicative of impedance changes. The computer processor may also be programmed to use the impedance changes to generate a sequence of the nucleic acid molecule.

The sensor may be used to detect a variety of biological events. Biological events may include, but are not limited to, DNA sequencing, capture and detection of pathogens, protein and biomarker detection, and other molecular diagnostics.

FIG. 17 shows an example system for both a bead-based sequencing approach and a bead free sequencing approach. In this example, the conjugated biomolecules are nucleic acid molecules. In the bead approach, there are a limited amount of nucleic acid molecules at the contact point of the two electrodes, which can result in a non-optimal signal strength. Additionally, due to the polydispersity of the particle size, the magnetic bead in this illustration may slide laterally. Sliding laterally may result in the bead losing contact with the electrode, creating signal noise. Sliding laterally may also cause a no-close circuit which may cause a loss of signal. By controlling the molecular weight, a physically entangled polymeric material may bridge the two electrodes or cover the electrodes, maximizing the detection of biological events.

Figure 18:
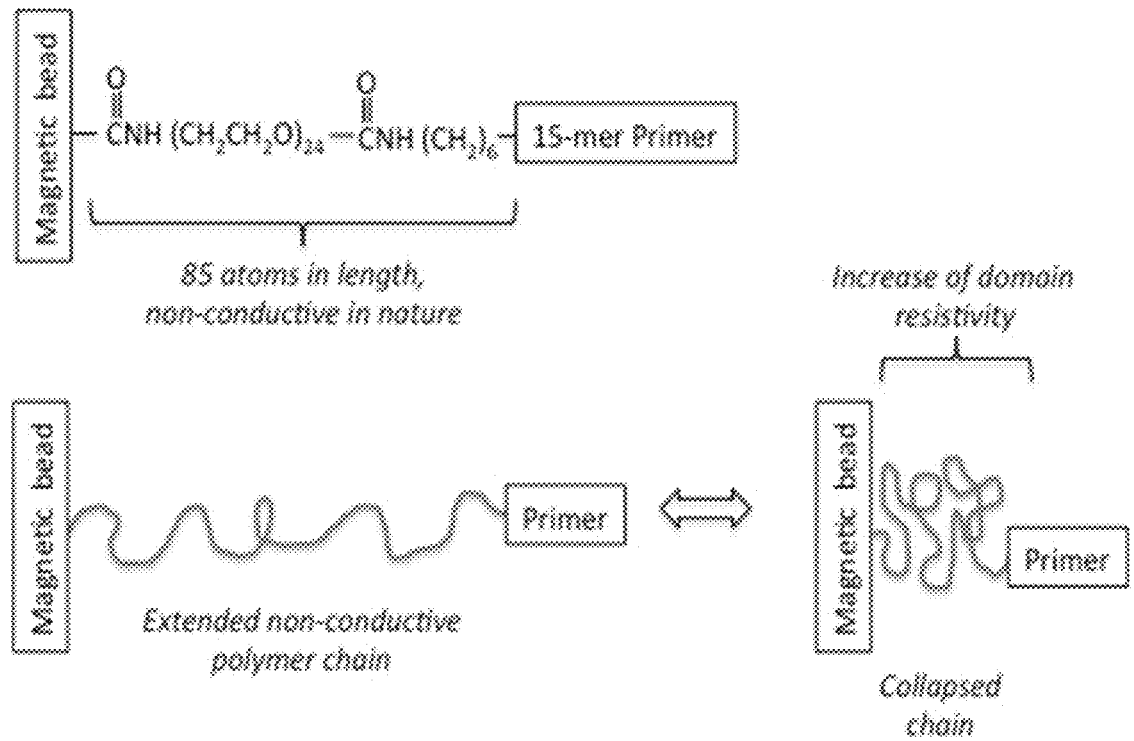
FIG. 18 schematically illustrates thermodynamic movement of linear polymer chains in solution.

An additional drawback to the bead-based approach may be the potential for thermodynamic movement of linear polymer chains in solution. FIG. 18 shows an example of a magnetic bead with a polymer linker attached to a fifteen base primer. The linker, comprising a poly(ethylene oxide) chain, is eighty-five atoms in length. If fully extended, the conductivity of the region in the vicinity of the bead can be similar to that of the conductivity of the bulk. However, when the 85-atom linker collapses, it may create a restively domain that may contribute to the background noise, alter the linearity, and affect other unknown signal parameters. A physically entangled polymeric material may mitigate such extending and collapsing phenomenon.

The electrode may be formed of a chemically inert conducting material, such as one or more metals (e.g., platinum, gold, or titanium). The electrode may be formed of a conductive metal oxide, for example, but not limited to, indium tin oxide (ITO). The support may comprise an oxide (e.g., a silicon oxide), such as silicon dioxide or a metal oxide. The support may be surface modified to enable the reactive coupling of polymeric materials to the surface of the support. Surface modification may include chemical modification by treatment with acids, bases, Ultraviolet-ozone treatement, or plasma treatment. Surface modification may allow for the reactive coupling of a linker molecule. Linker molecules may include crosslinkers or coupling agents. Non-limiting examples of crosslinkers include zero-length crosslinkers, homobifunctional crosslinkers, heterobifunctional crosslinkers, and trifunctional crosslinkers. Non-limiting examples of coupling agents include biotinylation reagents and silane coupling agents. For example, the surface may be modified with an amino-alkyl alkoxysilane. The amino-alkyl alkoxysilane may act as a coupling agent that couples the polymeric material to the support. The amino-alkyl alkoxysilane may contain one to three alkoxy groups that may react with hydroxyl groups on the surface of the substrate. The amino functional group of the amino-alkyl alkoxysilane may be replaced with other functional groups and/or may also contain a secondary reactive component (e.g., functional group) that may couple with the polymeric material. Example functional groups may include acrylamide, acrylate, thiol, maleimide, carboxylate, NHS ester, tetrafluorophenyl ester, pentafluorophenyl ester, epoxide, biotin, or streptavidin moieties. The polymeric material may bridge or cover the electrodes.

The polymeric material may be a gel, such as a hydrogel. The hydrogel may comprise non-reactive and reactive co-monomers. The hydrogel may contain one or more of acrylate, methacrylate, ethylene glycol, acrylamide, epoxide, vinyl alcohol, or (hydroxyethyl)methacrylate monomers. The hydrogel may comprise reactive copolymers, that may, for example, comprise a water-soluble non-reactive co-monomer, with non-limiting examples of such monomers including, 2-hydroxyethyla acrylate, vinylmethyl ether, acrylamide and N,N-dimethylacrylamide. In some cases, the hydrogel may also comprise reactive co-monomer that may or may not be water-soluble. The molar fraction of the reactive co-monomer may range, for example, from about 0.001 to 10, from about 0.01 to 10, from about 0.001 to 1, or from about 0.01 to 1. In some instances, a copolymer of poly(N,N-dimethylacrylamide-co-pentafluorophenylacrylate) may be used to form the hydrogel. In other instances, copolymers that contain bromoacetamidepentylacrylamide (BRAPA) may be used either alone or in conjunction with other polymers to form the hydrogel.

Figure 19:
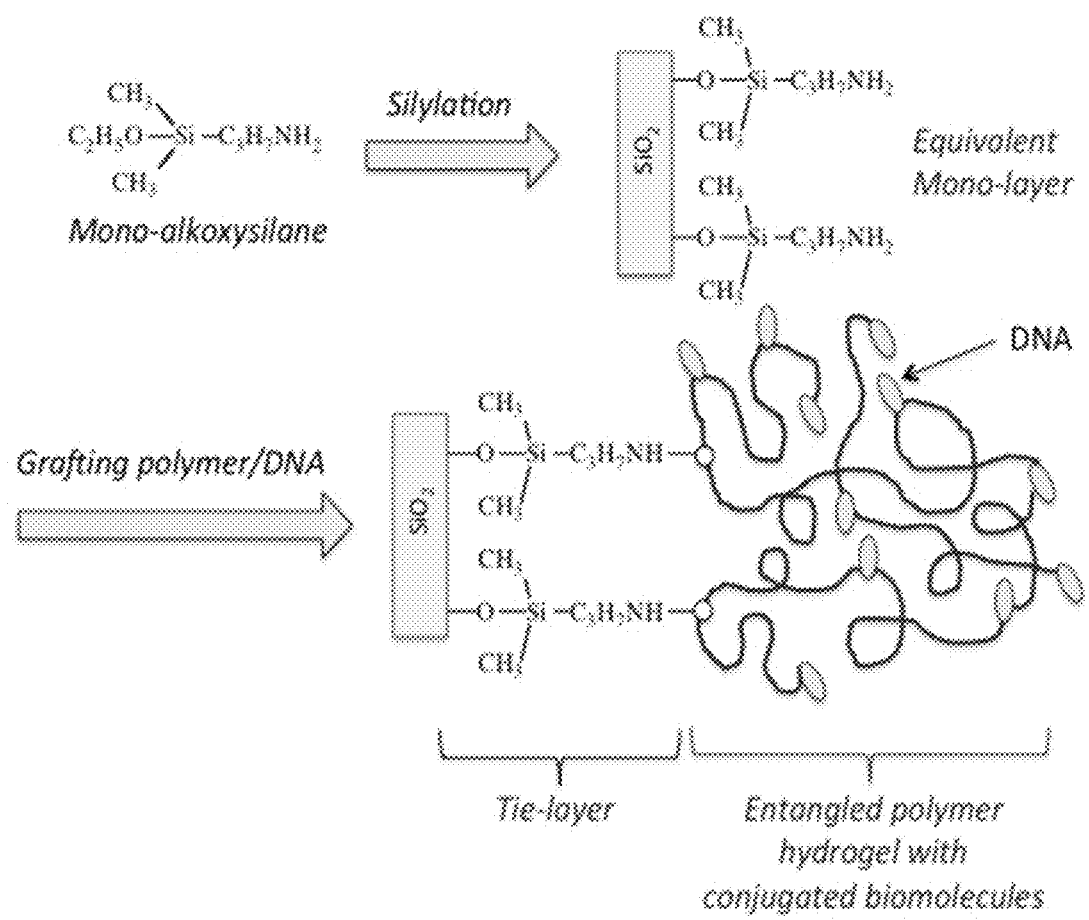
FIG. 19 schematically illustrates an entangled polymer network coupled to a solid support and primers.

An example of a hydrogel coupled to a silicon dioxide support is shown in FIG. 19. The hydrogel may provide for a physically entangled polymer network. The physical entanglement may restrict the thermodynamic extension and collapse to a certain degree. The presence of the charged nucleic acid molecules and their counter cations and other ions distributed throughout the hydrogel may prevent resistivity domains from forming. The use of hydrogels may improve the effective loading density of biomolecules and may be flexible enough to allow other molecules, such as enzymes, to penetrate to perform enzymatic reactions. In some examples, the surface density of a fifteen base primer may range from $2.0 \times 10^5$ to $1.2 \times 10^6$, which may be an order of magnitude higher than what may be observed with magnetic beads (see, e.g., FIG. 18).

The hydrogel may be seeded with primer oligos. The hydrogel may be seeded with between about 1 picomolar (pM) and 10,000 pM, between about 1 pM and about 8,000 pM, between about 1 pM and about 6,000 pM, between about 1 pM and 4,000 pM, between about 1 pM and 2,000 pM, between about 1 pM and 1,000 pM, between about 1 pM and 500 pM, or between about 1 pM and 250 pM primer oligos. In some embodiments, the hydrogel is seeded with greater than 1 pM, greater than 10 pM, greater than 50 pM, greater than 100 pM, greater than 500 pM, greater than 1,000 pM, greater than 2,000 pM, greater than 4,000 pM, greater than 6,000 pM, greater than 8,000 pM, greater than 10,000 pM, or more primer oligos. In some embodiments, the hydrogel is seeded with less than about 10,000 pM, less than about 8,000 pM, less than about 6,000 pM, less than about 4,000 pM, less than about 2,000 pM, less than about 1,000 pM, less than about 500 pM, less than about 100 pM, less than about 50 pM, less than about 10 pM, less than about 5 pM, less than about 1 pM, or fewer primer oligos. The primers may be reactive with the hydrogel. The primer may contain a reactive nucleophile. The reactive nucleophile may be a thiol. For example, a primer comprising a benzylthiol group may be an effective nucleophile.

Figure 20:
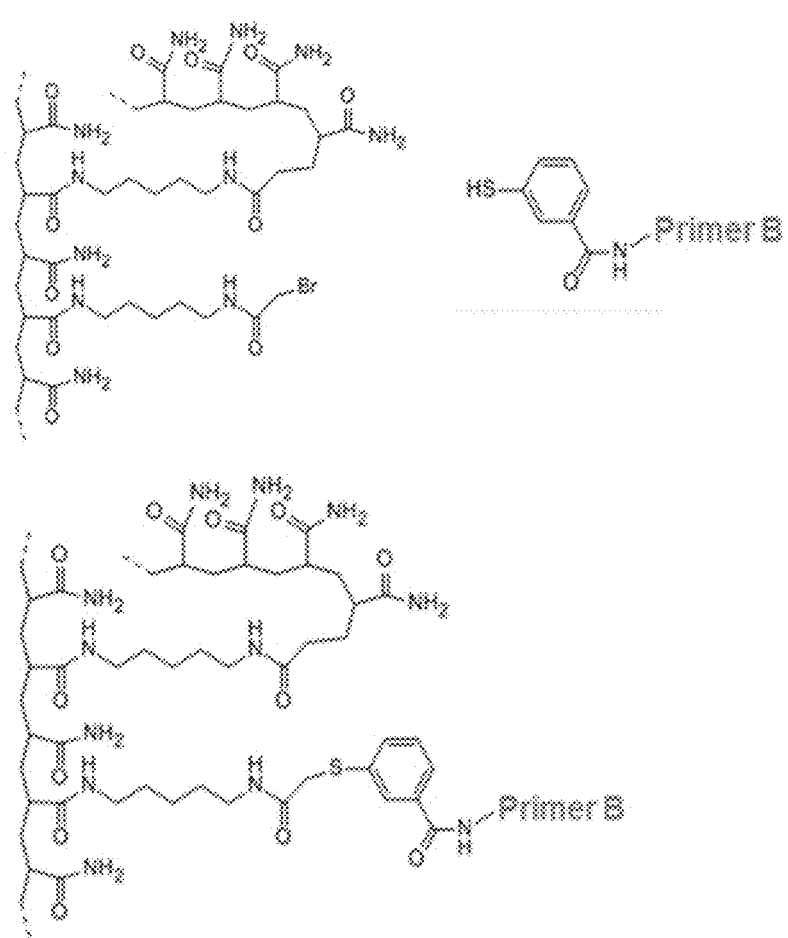
FIG. 20 schematically illustrates a reaction between a benzthiolated primer and Bromoacetamidepentylacrylamide (BRAPA)

FIG. 20 shows a structural drawing of a hydrogel comprised at least partially of BRAPA. The BRAPA may serve as a branching agent during atom-transfer radical-polymerization and as reactive group for biomolecule conjugation. The BRAPA may copolymerizes with acrylamide and other vinyl containing monomers to form a thin film hydrogel on the support surface. The residual bromoacetamide groups react with a variety of nucleophiles, including thiolated oligonucleotides. This reaction is exemplified by the benzthiolated Primer B conjugating with the bromoacetamide pendent group of the polymer chain.

The polymeric material may be a porous polymer monolith (PPM). The PPM may be a homopolymer, copolymer, or terepolymer that comprises reactive functional groups. The reactive functional groups may be reactive to a variety of chemical moieties including, but not limited to, primary amines, secondary amines, mercaptos, hydroxyl groups, thiol groups, and carboxylic acid groups. The reactive functional groups may be comprised of carboxylic acids, esters of N-hydroxysuccinimide, pendants of 4,4'-dimethylazlactone, or esters of tetrafluorophenol and pentafluorophenol.

The PPM may be polymerized using a variety of approaches, including chemical, thermal, or UV radiation approaches. FIGS. 21A-21D and FIG. 22 show the procedure for fabricating a support with a PPM thin film. FIG. 21A shows the substrate surface, previously cleaned by isopropanol rinsing and soaking in RCA solutions. FIG. 21B shows the substrate surface modified by (3-acryloxypropyl) trimethoxysilane, which may introduce polymerizable function groups to the surface. FIG. 21C shows a solution of reactive monomers, pentafluorophenyl acrylate or vinylazlactone for example, a multifunctional crosslinker, and initiators in a porogen solvent dispensed on the surface of the substrate in preparation for polymerization. Photoinitiators may be used for initiating the polymerization reaction. The photoinitiators may be biomolecular photoinitiators that may comprise benzophenone and α,α-dimethoxy-α-phenylacetophenone. This mixture of initiators may enable photopolymerization to proceed in open air. In some cases, a glass lid having a fluorinated surface as a release may be placed over the monomer mixture prior to polymerization. FIG. 21D shows the support with PPM thin film. After polymerization the lid is released and removed and the PPM film is rinsed with hexane and air dried to give a reactive thin film of PPM for bioconjugation.

Figure 22:
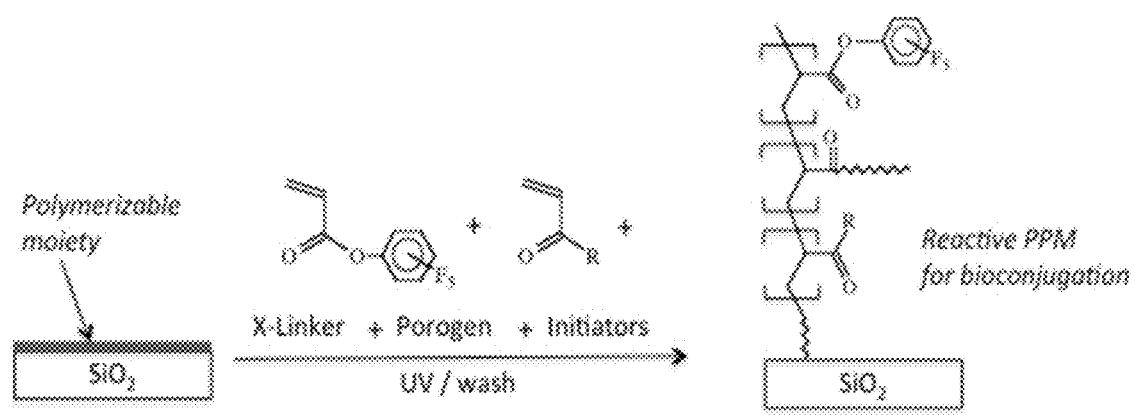
FIG. 22 schematically illustrates a polymerization chemistry for PPM thin film preparation.

An illustrative example for the preparation of PPM grafted onto the substrate surface is shown in FIG. 22. Briefly, a silicon dioxide substrate with a polymerizable surface moiety may be exposed to a crosslinker, porogen, and initiators and treated with UV exposure followed by washing to form a PPM film covalently attached to the substrate surface. The PPM film may then be reactive and used for bioconjugation.

The PPM may be seeded with primer oligos. The PPM may be seeded with between about 1 picomolar (pM) and 10,000 pM, between about 1 pM and about 8,000 pM, between about 1 pM and about 6,000 pM, between about 1 pM and 4,000 pM, between about 1 pM and 2,000 pM, between about 1 pM and 1,000 pM, between about 1 pM and 500 pM, or between about 1 pM and 250 pM primer oligos. In some embodiments, the PPM is seeded with greater than 1 pM, greater than 10 pM, greater than 50 pM, greater than 100 pM, greater than 500 pM, greater than 1,000 pM, greater than 2,000 pM, greater than 4,000 pM, greater than 6,000 pM, greater than 8,000 pM, greater than 10,000 pM, or more primer oligos. In some embodiments, the PPM is seeded with less than about 10,000 pM, less than about 8,000 pM, less than about 6,000 pM, less than about 4,000 pM, less than about 2,000 pM, less than about 1,000 pM, less than about 500 pM, less than about 100 pM, less than about 50 pM, less than about 10 pM, less than about 5 pM, less than about 1 pM, or fewer primer oligos. The primers may contain a variety of reactive groups that are reactive with the PPM. Example reactive groups include primary and secondary amines, mercaptos, hydroxyl groups, thiol groups, and carboxylic acids.

Figure 23:
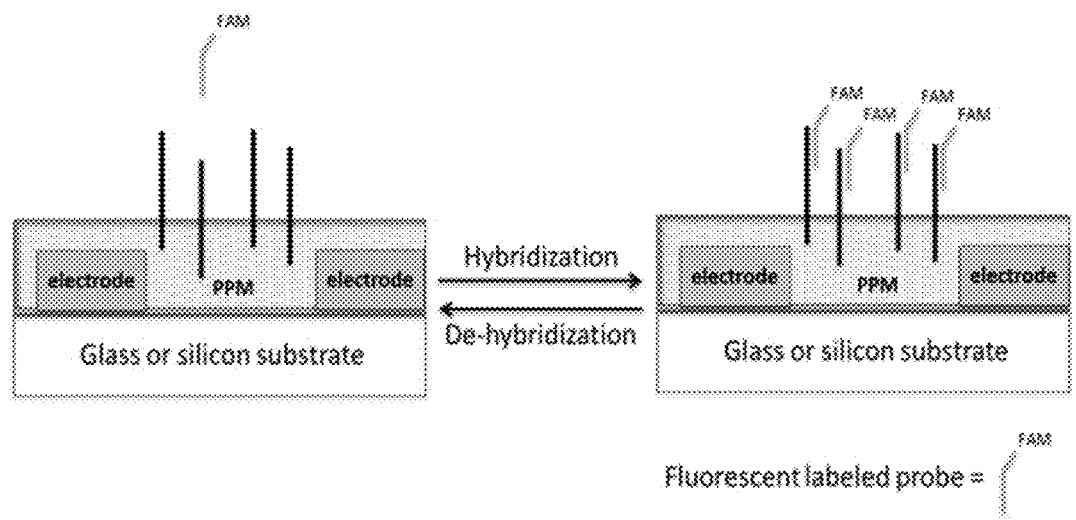
FIG. 23 schematically illustrates a hybridization-dehybridization (Hyb-DeHyb) assay performed with a primer conjugated to the PPM thin film.
Figure 24:
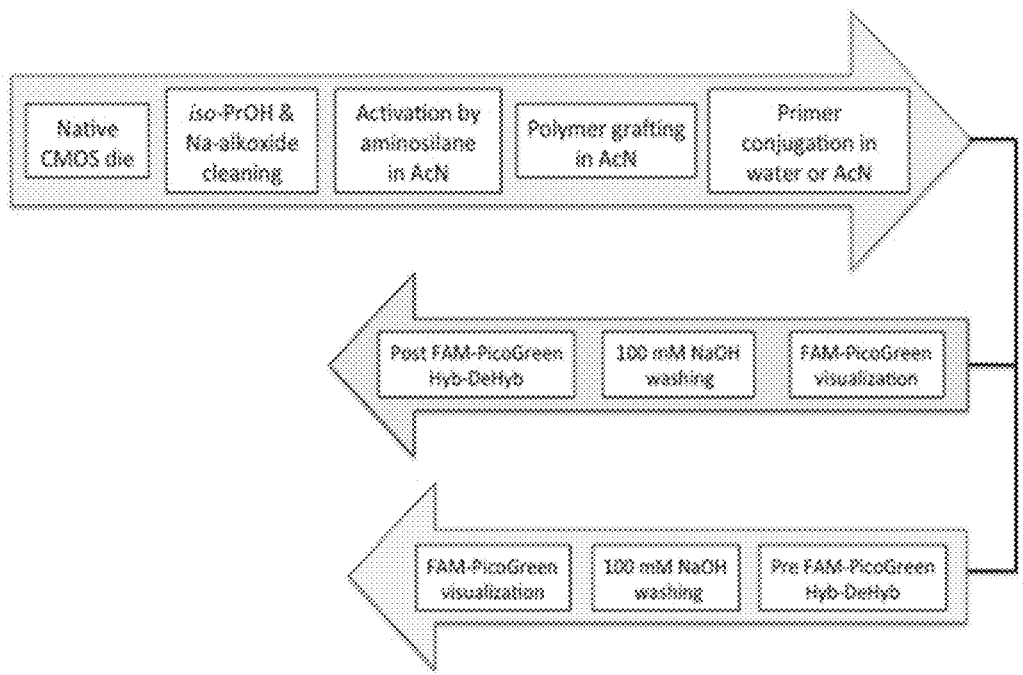
FIG. 24 schematically illustrates procedure for preparing primer conjugated polymer coated supports and visualization of primer density.

Primer density may be determined by a hybridization-dehybridization (Hyb-DeHyb) assay and PicoGreen visualization. FIG. 23 shows a schematic of the Hyb-DeHyb assay performed with a surface conjugated primer and a FAM-labeled oligo that is complementary to the primer. FIG. 24 illustrates the process flow for preparing a primer conjugated support and the techniques for determining primer conjugation.

Figure 25:
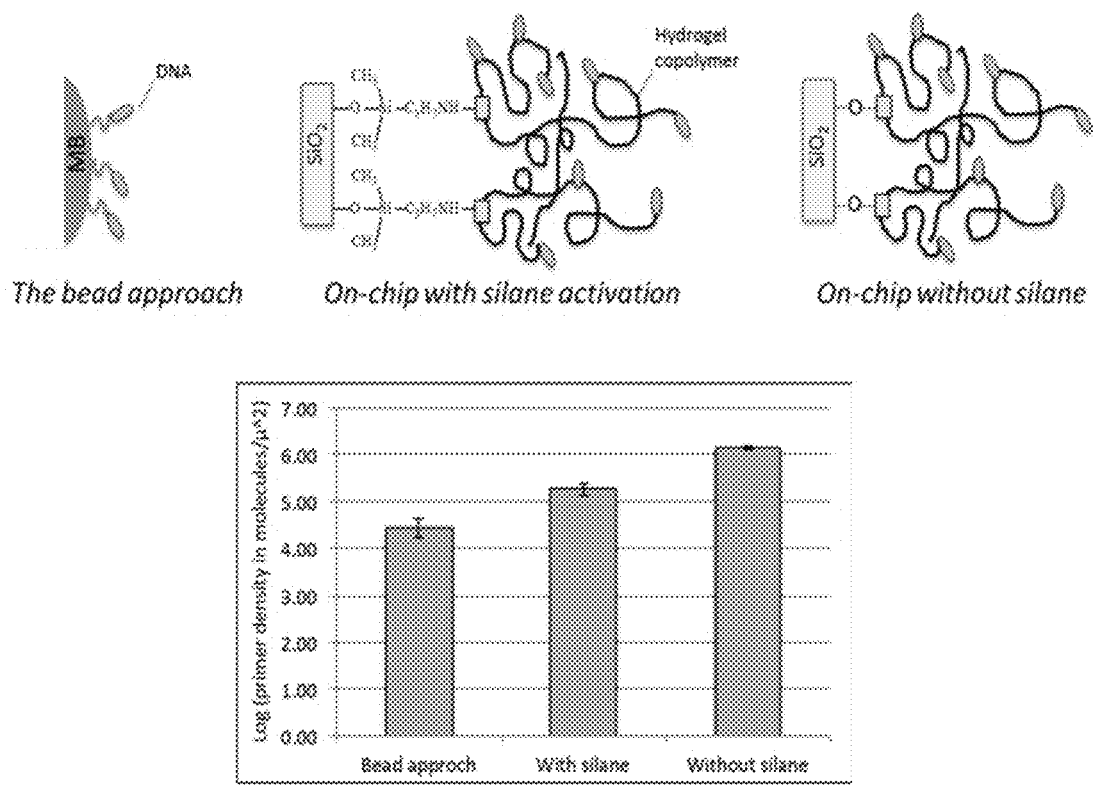
FIG. 25 schematically illustrates primer density of primer conjugated supports both with and without silane activation.

Polymer grafting may be achieved both with and without the use of a silane to activate the substrate surface. FIG. 25 shows improved primer density of multiple substrate surfaces prepared both with and without the use of a silane. Primer density may be found to be higher in the absence of a silane. In the absence of the silane group, rather than the polymeric material forming an amide bond with the aminosilane coupling agent, the polymeric material may couple directly to the support surface through ester bond formation. It is unexpected to achieve a higher primer density result from the absence of the aminosilane coupling agent and that the ester linkages survive multiple 100 millimolar (mM) NaOH washes.

The primer may participate in an amplification reaction. During the amplification reaction, the primer may form clonal colonies or the primer may cover the entire surface of the support and form a lawn-type coverage. The primer may be seeded at a concentration ranging from 1 pM to 4000 pM. The seeding density may be critical for the formation of clonal colonies. For example, if the seeding density is too high and primers are too close together a lawn-type coverage will form of mixed colonies, which may not permit the use of a confined amplification approach. If the seeding density is too low, the support will not be utilized effectively. After seeding, the templates may undergo an amplification reaction. A variety of amplification reactions may be used, but methods of choice may include methods that use a confined amplification scheme or amplification schemes that may be combined with a confinement approach. Examples of amplification schemes include, polymerase chain reaction, recombinase polymerase amplification, invader amplification, bridge amplification, and wildfire amplification.

Figure 26A:
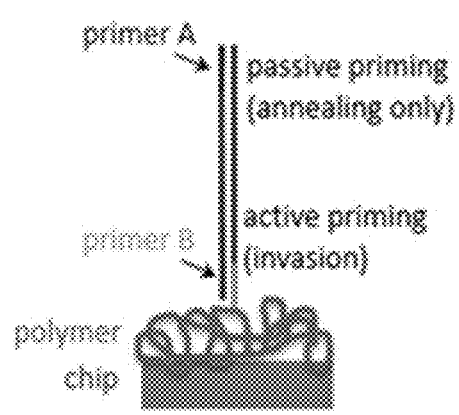
FIGS. 26A-26C schematically illustrate immobilized primer arrangements with regard to the polymer coated support and method of building confinement into the amplification reaction.
Figure 26B:
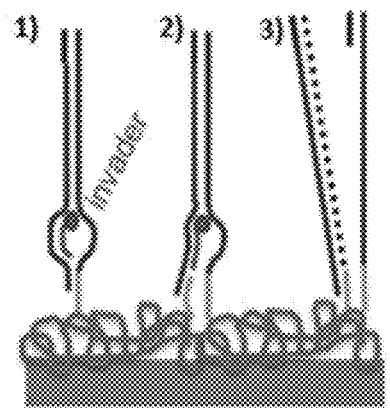
Figure 26C:
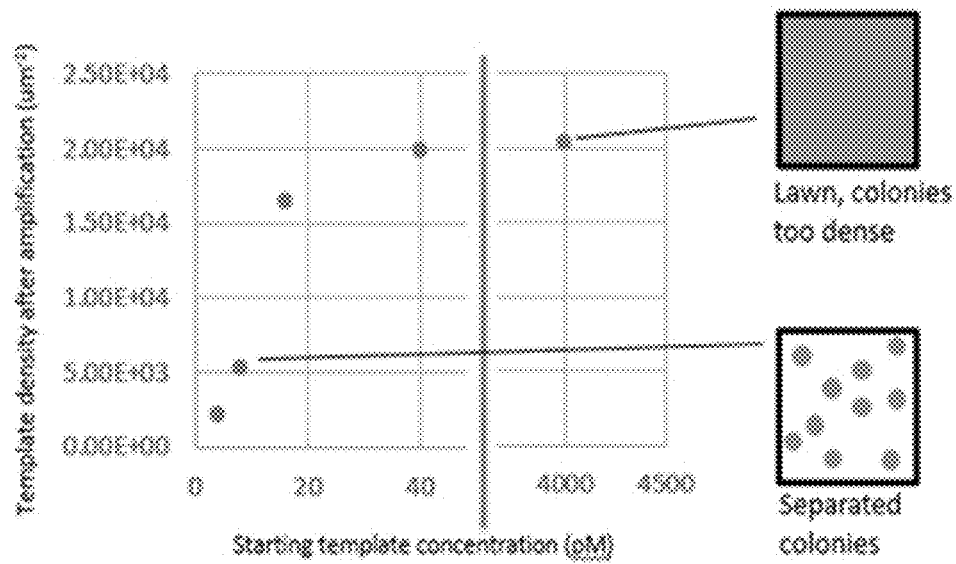

The immobilized primer arrangement with regard to the polymeric coated support and an example use of confinement in the system is shown in FIGS. 26A-26C. FIGS. 26A and 26B show a schematic for invader amplification, a surface confined amplification method. Briefly, a non-extendable invader may facilitate opening of the duplex of a target nucleic acid in close proximity to the support surface. Opening the duplex of the target nucleic acid may allow for hybridization of the template with a surface immobilized primer, which may lead to a primer extension and amplification. FIG. 26C shows the template density after amplification, as a function of starting template concentration, from a concentration titration experiment. In this example, a seeding concentration from 3 pM to 4000 pM is used. From 40 pM to 4000 pM the system may be saturated (i.e., a lawn of templates is expected to be formed) and little change in amplification level is observed. At lower seeding concentrations the amplification level may drop off, which may be explained by the formation of distinct colonies.

Figure 27:
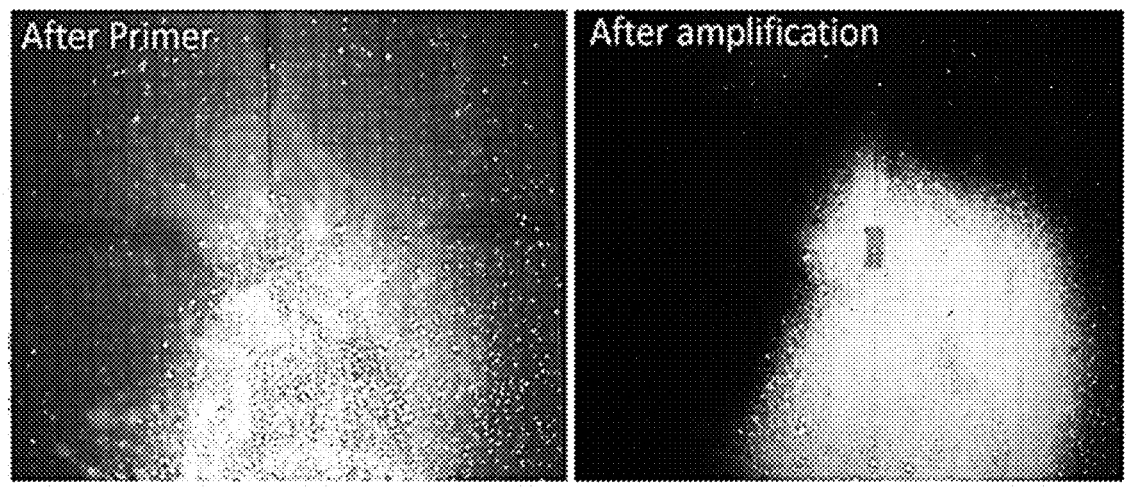
FIG. 27 shows visualization of the primer density before and after an amplification reaction.

Primer seeding density and amplification may be visualized using FAM-PicoGreen visualization. FIG. 27 shows an example of FAM-PicoGreen visualization both after primer seeding and after amplification.

The sequencing reaction may generate an electrochemical signal. The signal may be indicative of individual nucleic acid bases. The electrochemical signal may include impedance, potentiometric, cyclic voltammetric, spectroscopic, or amperometric signal. In other cases, the signal may be monitored using non-electrochemical techniques. Non-electrochemical techniques may include fluorescent spectroscopy, surface plasmon resonance, or cantilever techniques.

The electrodes may be coupled to a Debye layer (or double layer) during sequencing. The nucleic acid to be sequenced may also be within the Debye layer so that the sequencing reaction may occur within the layer. Incorporation of nucleotides into the nucleic acid molecules within the Debye layer may generate a measureable signal. The measureable signal may be an electrochemical signal or an impedance signal. The signal may be measured during a transient or steady state condition.

Figure 28:
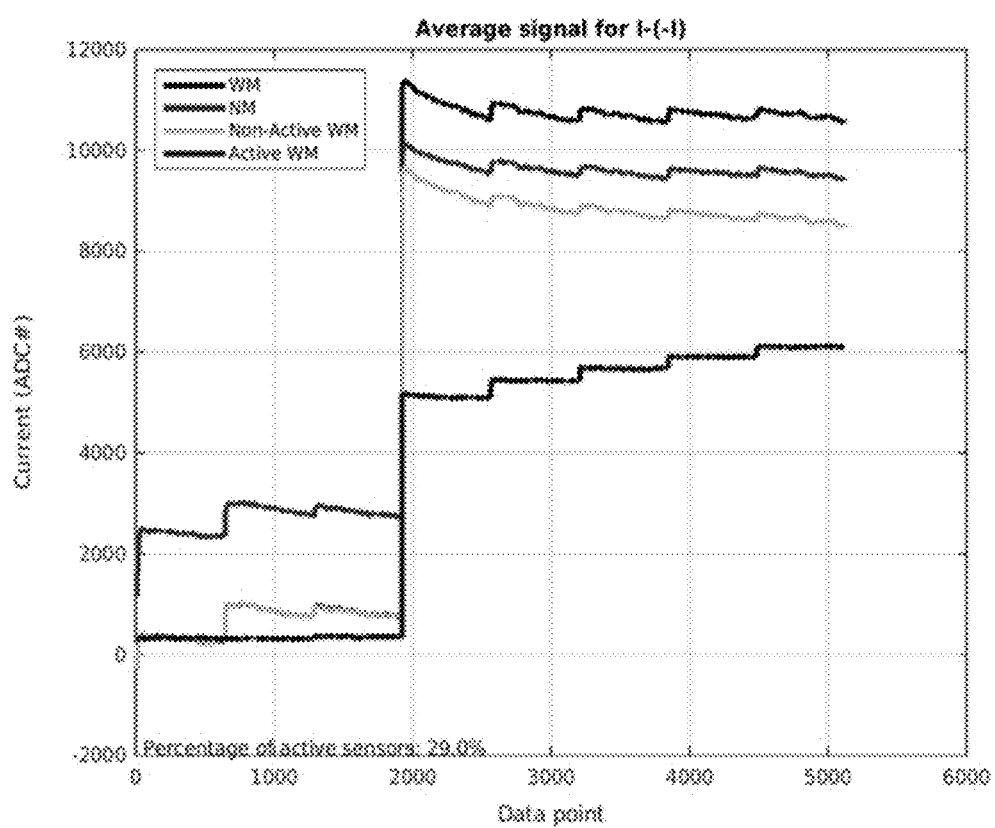
FIG. 28 shows electronic detection of primer extension and nucleic acid incorporation for templates amplified on a support surface.

Primer extension may be monitored via electronic detection. FIG. 28 shows an example result of electronic detection of primer extension and nucleotide incorporation for nucleic acid templates amplified on a support surface. The nucleic acid templates amplified on the support surface may be bound to a primer and polymerase and exposed to a solution containing all four nucleotides. The solution containing all four nucleotides is called the Run-Off mix. FIG. 28 shows the jump in the electronic signal following introduction of the Run-Off mix onto the support. The multiple traces in FIG. 28 may denote the jumps in electronic signal observed for different sets of sensors or jump signals following correction with a reference or background signal. The jump in electronic signal may demonstrate primer extension due to nucleotide incorporation.

Figure 29:
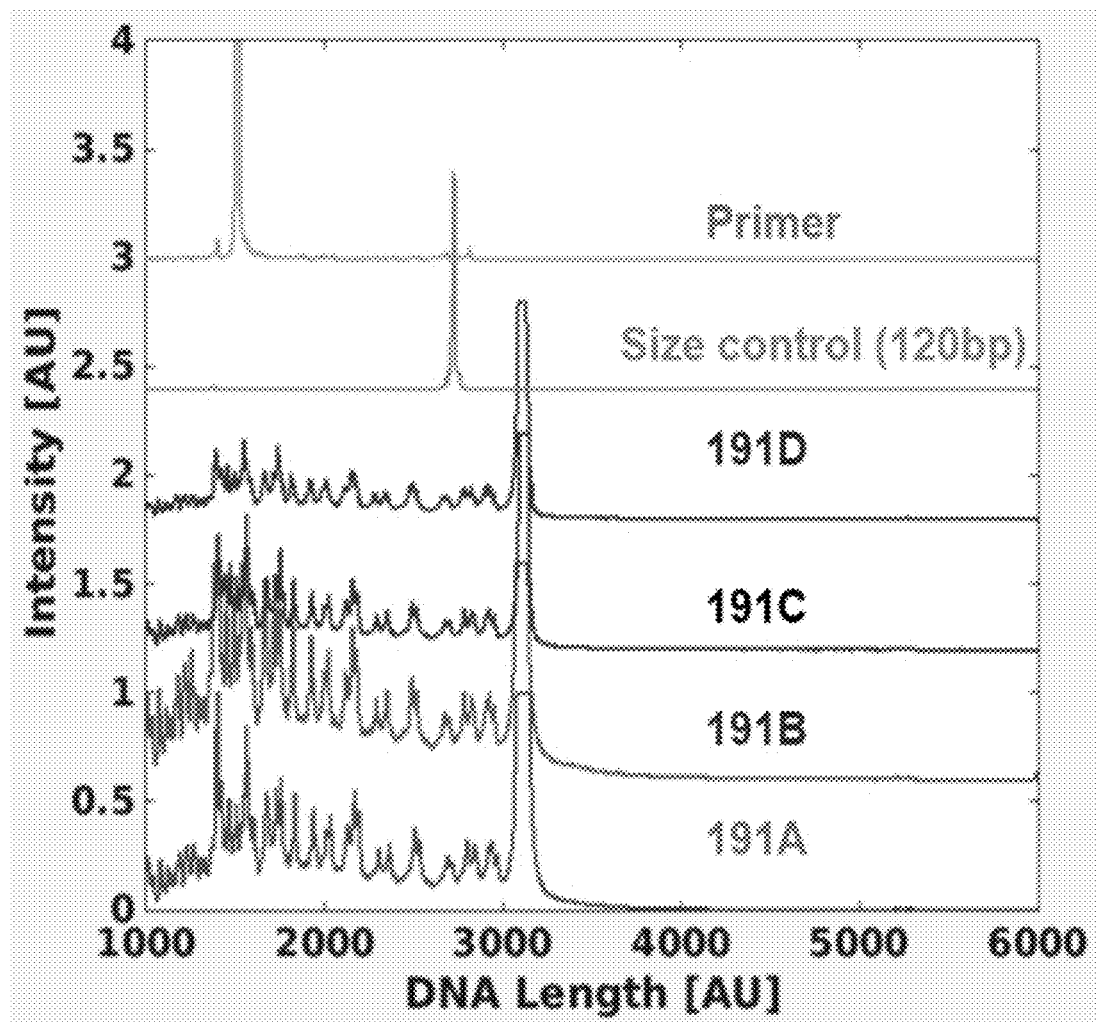
FIG. 29 shows capillary electrophoresis readout of extension of FAM-labeled primers during a sequencing experiment.

Primer extension may also be verified via capillary electrophoresis. FIG. 29 shows the capillary electrophoresis readout of the extension of a FAM-labeled primer during a run-off or sequencing experiment. The extended strand may be melted off using sodium hydroxide following the run-off or sequencing reaction and may be run on a capillary electrophoresis. Four supports (191A, 191B, 191C, and 191D) are extended using run-off or sequencing and show complete extension. The size of the extended strand is larger than the size of the 120 base pair control, which is expected based on the size of the amplification template. The smaller peaks present may be close to the noise level of the system.

Figure 30A:
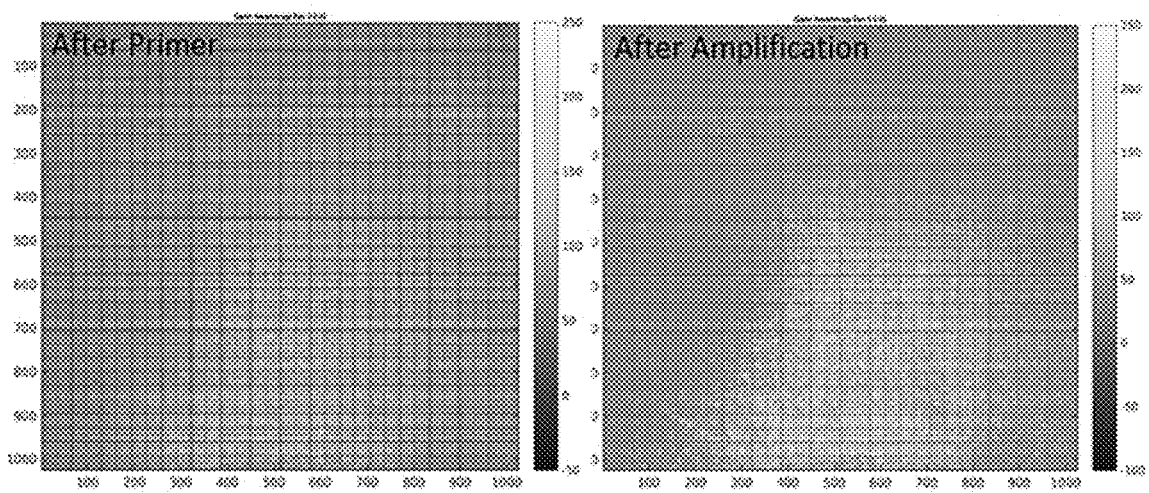
FIGS. 30A and 30B show visualization of primer density and electronic detection of nucleic acid incorporation on a support surface.
Figure 30B:
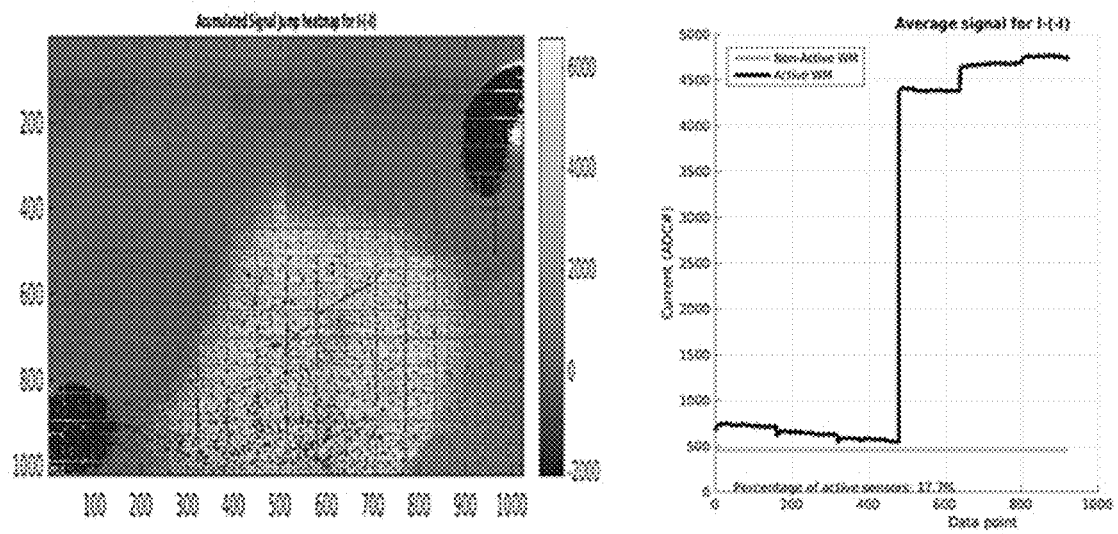

An example of monitoring the support from conjugation of the primer to run-off or sequencing experiments is shown in FIGS. 30A and 30B. FIG. 30A shows FAM-PicoGreen micrographs both after primer conjugation and after target amplification. FIG. 30B shows the cumulative FAM-PicoGreen micrograph and the electronic signal due to the run-off or sequencing experiment.

Methods for Redox Mediated Sequencing

A redox mediator moiety can be any species that comprises one or more components (e.g., functional groups) that can participate in a redox reaction, such as, for example, reduction or oxidation. In an oxidation reaction, a redox mediator moiety donates one or more electrons to another species, such that the redox mediator moiety loses the one or more elections to another species, resulting in an oxidized redox mediator moiety. Moreover, in a reduction reaction, a redox mediator moiety can accept one or more electrons from another species, such that the redox mediator moiety gains the one or more electrons from the other species, resulting in a reduced redox mediator moiety. In some cases, a redox mediator moiety can donate an electron(s) in an oxidation reaction, but cannot readily gain an electron(s) from another species in a reduction reaction. In other cases, a redox mediator moiety can receive an electron(s) in a reduction reaction, but cannot readily donate an electron(s) to another species in an oxidation reaction. Still, in other cases, a redox mediator moiety can both donate an electron(s) to another species in an oxidation reaction and gain an electron(s) from another species in a reduction reaction. Moreover, the charge of a redox mediator moiety will vary depending upon its oxidation state. Depending upon its oxidation state, a redox mediator moiety may be positively charged, neutral or negatively charged.

The cycle of oxidation and/or reduction of a given redox mediator moiety and its oxidized and/or reduced forms can occur cyclically such that an electron(s) is repeatedly transferred back-and-forth between a redox mediator moiety and another species. For example, in the case of a redox mediator moiety that donates an electron(s) in an oxidation reaction, the redox mediator moiety can donate its electron(s) to an additional species to form an oxidized redox mediator moiety and a reduced additional species. The oxidized redox mediator moiety can then receive an electron(s) from the reduced additional species in a reduction reaction, thus, regenerating the redox mediator moiety. In another example, in the case of a redox mediator moiety that accepts an electron(s) from an additional species in a reduction reaction, the redox mediate moiety can accept an electron(s) from the additional species to form a reduced redox mediator moiety and an oxidized additional species. The reduced redox mediator moiety can then donate an electron(s) back to the oxidized additional species to regenerate the redox mediator moiety. In the case of a redox mediator moiety that can readily donate and accept an electron(s), both types of cycling can occur. During cycling of an electron(s) between species, a redox mediator moiety may go from neutral to negatively charged or vice versa; from positively charged to neutral or vice versa; from one positive charge to a higher positive charge (e.g., +1 to +2); from one negative charge to a higher negative charge (e.g., −1 to −2); from one positive charge to a lower positive charge (e.g., +2 to +1); or from one negative charge to a lower negative charge (e.g., −2 to −1).

A redox mediator moiety can comprise an organic compound, an organometallic compound, a nanoparticle, one or more metals, another suitable material and combinations thereof. In some cases nanoparticles, each having plurality of redox active molecules are used as a redox mediator moiety. In some cases, a redox mediator molecule is water soluble, which can aid in its participation in aqueous phase reactions and/or detection schemes.

Non-limiting examples of a redox mediator moiety include a ferrocene derivative, such as alkyl ferrocene, ferrocene acetate, alkyl ferrocene dimethylcarboxamide, acetyl ferrocene, propoyl ferrocene, butyryl ferrocene, pentanoyl ferrocene, hexanoyl ferrocene, octanoyl ferrocene, benzoyl ferrocene, 1,1'-diacetyl ferrocene, 1,1'-dibutyryl ferrocene, 1,1'-dihexanoyl ferrocene, ethyl ferrocene, propyl ferrocene, n-butyl ferrocene, pentyl ferrocene, hexyl ferrocene, 1,1'-diethyl ferrocene, 1,1'-dipropyl ferrocene, 1,1'-dibutyl ferrocene, 1,1'-dihexyl ferrocene, cyclopentenyl ferrocene, cyclohexenyl ferrocene, 3-ferrocenoyl propionic acid, 4-ferrocenoyl butyric acid, 4-ferrocenylbutyric acid, 5-ferrocenylvaleric acid, 3-ferrocenoyl propionic acid esters, 4-ferrocenoyl butyric acid esters, 4-ferrocenyl butyric acid esters, 5-ferrocenylvaleric acid esters, dimethylaminomethyl ferrocene, 1,1 dicarboxyferrocene, carboxyferrocene, and vinyl-ferrorcene; a porphyrin derivitive, such as hydroporphyrins, chlorins, bacteriochlorins, isobacteriochlorins, decahydroporphyrins, corphins, porphyrins phthalocyanine, pyrrocorphin, and metal-complexed porphyrins including Magnesium porphyrin, Zinc porphyrin, and Iron porphyrin; a quinone derivitive, such as 2,5-dichloro-1,4-benzoquinone, Methylene Blue, Methyl-1,4-benzoquinone, Anthraquinone, and 1,4-dihydroquinone; 1,4-dihydroxy-2-naphthoic acid; and a nanoparticle, such as a CdS nanoparticle and ZnS nanoparticles.

As described elsewhere herein, a redox mediator can be coupled with a nucleotide. A redox mediator moiety can be coupled with a nucleotide either covalently or non-covalently, directly or indirectly. In some cases, a redox mediator moiety is attached to a phosphate group of a nucleotide (e.g., terminal phosphate or gamma-phosphate). In some cases, a plurality of redox mediator moieties can be associated with a nucleotide. Moreover, in some cases, a nucleotide can include about 2 redox mediator moieties, about 4 redox mediator moieties, about 6 redox mediator moieties, about 8 redox mediator moieties, about 10 redox mediator moieties, about 15 redox mediator moieties, about 20 redox mediator moieties, about 30 redox mediator moieties, about 50 redox mediator moieties or more. In some cases, a nucleotide can be associated with least about 2 redox mediator moieties, at least about 4 redox mediator moieties, at least about 6 redox mediator moieties, at least about 8 redox mediator moieties, at least about 10 redox mediator moieties, at least about 15 redox mediator moieties, at least about 20 redox mediator moieties, at least about 30 redox mediator moieties, or at least about 50 redox mediator moieties.

In an aspect, the present disclosure provides a method for sequencing a nucleic acid molecule. The method can include tethering a template nucleic acid molecule in proximity to a sensor. The method can further include creating an elongation complex tethered in proximity to the sensor, where the elongation complex comprises a nucleic acid polymerase associated with the template nucleic acid molecule and an oligonucleotide (e.g., primer) that is hybridized to the template nucleic acid molecule. An elongation complex can also include a nucleotide that is subsequently incorporated into the oligonucleotide. The method can further include contacting the elongation complex with a solution comprising nucleotides such that a nucleotide that is complimentary to the template nucleic acid molecule at a position adjacent to the oligonucleotide becomes associated with the elongation complex, where the nucleotides are associated with a redox mediator moiety. The method can further include detecting the redox mediator moiety with the sensor when the nucleotide is associated with the elongation complex. The method can further include incorporating the nucleotide into the oligonucleotide, thereby releasing the redox mediator moiety from the nucleotide. The operations described here can be repeated through one or more cycles to sequence the template nucleic acid molecule.

In some cases, a plurality of clonal template nucleic acid molecules is tethered in proximity to the sensor. Clonal surface amplification can be can be used to multiply the number of copies of a template nucleic acid molecule at a given sensor site. Suitable methods for amplification are described in U.S. Pat. No. 5,641,658, U.S. Patent Publication No. 2013/0231254A1, U.S. Patent Publication No. 2013/0225421A1, U.S. Patent Publication No. 2013/0281307A1, U.S. Patent Publication No. 2016/0032371A1, and U.S. Patent Publication No. 2012/0156728A1, each of which is entirely incorporated herein by reference.

Figure 34A:
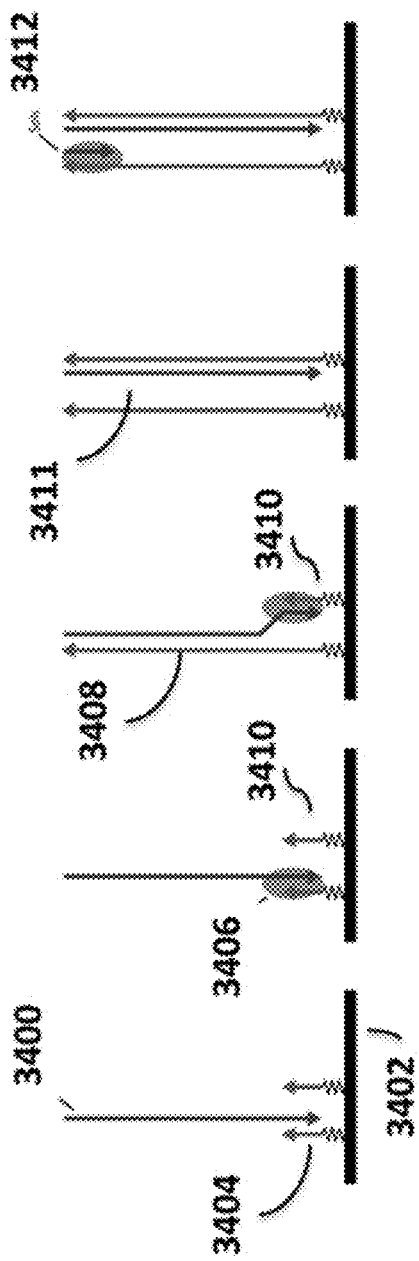
FIGS. 34A and 34B show an example clonal amplification method.

FIG. 34A schematically depicts an example process for clonal amplification, sometimes referred to as "polymerase walking". As shown in FIG. 34A, a single-stranded nucleic acid template 3400 can be seeded onto a surface 3402 (e.g., adjacent to a sensor, on the sensor) comprising a first primer 3404 complementary to a segment (e.g., 3'-segment or 5'-segment) of the nucleic acid strand. A polymerase (e.g., a strand-displacing polymerase) 3406 can be added and the first primer 3404 can be extended in a primer extension reaction, resulting in synthesis of a first complementary strand 3408. The immobilized end of the single-stranded nucleic acid template 3400 is in base-pairing equilibrium with surface-immobilized first primer 3404 and additional copies of the first primer 3404, represented in FIG. 34A as a second primer 3410. Accordingly, the immobilized end of the single-stranded nucleic acid template 3400 can dehybridize from the first primer 3404 and hybridize with the second primer 3410, such that the single-stranded nucleic acid template 3400 is hybridized to both the first complementary strand 3408 and the second primer 3410. The polymerase 3406 then extends the second primer 3410 in a primer extension reaction, displacing the first complementary strand 3408, leaving first complementary strand 3408 single-stranded. Moreover, a second complementary strand 3411 hybridized with the single-stranded nucleic acid template 3400 is generated.

Figure 34B:
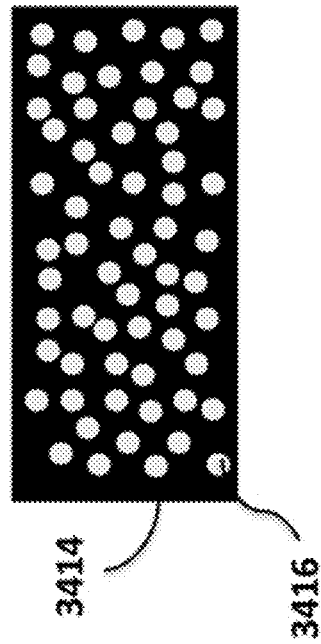

A free primer 3412 can then be added and hybridize with the non-surface immobilized end of the displaced first complementary strand 3408 and subsequently be extended by the polymerase in a primer extension reaction to generate a third complementary strand 3411. The various stages of the scheme can be repeated for additional cycles, resulting in exponential amplification of the original single-stranded nucleic acid. Where single-stranded template nucleic acid molecules of a nucleic acid molecule library are seeded to different regions of the surface 3402 such that each region only receives, on average, at most 1 single-stranded template nucleic acid molecule 3400 per region, the amplification can be clonal such that the surface 3402 is covered with a plurality of distinct colonies. Clonality is achieved because there are no released synthesized strands during the various stages of the scheme. In some cases, colonies produced by the scheme do not comingle (e.g., grow into each other), which can permit better than Poissonian seeding concentrations of nucleic acid template. An example surface 3414, on which various clonal colonies 3416 of nucleic acids are present, is schematically depicted in FIG. 34B.

A template nucleic acid immobilized on a surface in suitable proximity to a sensor or on a sensor and may be a member of a population (e.g., a clonal population, including a clonal population of template nucleic acid molecules generated as described elsewhere herein) of template nucleic acid molecules. The template nucleic acid may be immobilized on the surface using reversible covalent, irreversible covalent, or reversible non-covalent coupling as described elsewhere herein. Examples of non-covalent coupling include hybridization and binding pair interactions. The template nucleic acid can be sequenced using redox-mediated nucleic acid sequencing. In such a sequencing scheme, a primer can be bound to the template nucleic acid molecule and a nucleic acid polymerase can incorporate nucleotides that are provided to the template nucleic acid molecule and include a coupled redox mediator moiety that is detectable by the sensor. The sensor detects the redox mediator moiety via repeated exchange (e.g., donation/accepting, oxidation/reduction) of electrons between the sensor and the redox mediator moieties. Signals generated at the sensor and indicative of these electron exchanges are detected by electronic components electrically coupled to the sensor to determine that a nucleotide associated with the redox moiety is incorporated. Sequencing of a clonal population of many copies of a template nucleic acid can provide suitable signal-to-noise ratios, as a higher number of exchanges may be measureable due to parallel incorporation of a redox mediator moiety across the population.

In some cases, a template nucleic acid molecule or a population of template nucleic acid molecules is separately and sequentially exposed to each of a set of different types of nucleotides (e.g., nucleotides having the base of A, T or U, C or G), with a washing step in-between application of different types of nucleotides. As it is known at any given point, which particular nucleotide is in contact with the template nucleic acid or population of template nucleic acid molecules, observed signal can be correlated to an incorporation of that particular nucleotide. In some cases, each different type of nucleotide is associated with a different redox mediator moiety, where each different redox mediator moiety is indicative of its associated nucleotide type. In other cases, two or more of the different type of nucleotides is associated with the same redox mediator moiety. In some cases, all of the different types of nucleotides are associated with the same redox mediator moiety. In cases where different types of nucleotides comprise the same redox mediator moiety, separation of contacts with different nucleotides permits detection of the same redox mediator across different nucleotides exposed to the template nucleic acid molecule or population of template nucleic acid molecules. Only one nucleotide is present at any given time and the identity of the nucleotide is known.

In other cases, a template nucleic acid molecule or population of template nucleic acid molecules is simultaneously exposed to a set of different types of nucleotides. In such cases, each type of nucleotide is associated with a different redox mediator moiety. Each different redox mediator moiety can give rise to a different signal that can be used to identify a particular nucleotide that is incorporated. Additional methods of redox-mediated sequencing can found in U.S. Patent Publication No. 2013/0109577, each of which is entirely incorporated herein by reference.

Any suitable type of sensor can be used for redox-mediated sequencing. In some cases, the surface is associated with or comprises a sensor. In some cases, the sensor is a nanogap electrode. A nanogap electrode can have two electrodes separated from each other by a "diffusion distance". In some cases the electrodes are about 10,000 nanometers (nm), about 1,000 nm, about 500 nm, about 100 nm, about 50 nm, about 10 nm, or about 5 nm apart. In some instances, the electrodes are less than about 10,000 nanometers nm, less than about 1,000 nm, less than about 500 nm, less than about 100 nm, less than about 50 nm, less than about 10 nm, or less than about 5 nm apart.

In some cases, the sensor comprises a single electrode that has its polarity switched at a time interval. In some cases, the time interval is about 5 nanoseconds (ns), about 10 ns, about 50 ns, about 100 ns, about 500 ns, about 1 millisecond (ms), about 5 ms, about 10 ms, about 50 ms, or about 100 ms. In some cases, the time interval is at most about 5 nanoseconds (ns), at most about 10 ns, at most about 50 ns, at most about 100 ns, at most about 500 ns, at most about 1 millisecond (ms), at most about 5 ms, at most about 10 ms, at most about 50 ms, or at most about 100 ms. In some cases, the time interval is at least about 5 nanoseconds (ns), at least about 10 ns, at least about 50 ns, at least about 100 ns, at least about 500 ns, at least about 1 millisecond (ms), at least about 5 ms, at least about 10 ms, at least about 50 ms, or at least about 100 ms.

In some cases, a surface is associated with or comprises a plurality of sensors, each sensor having a tethered nucleic acid template to-be-sequenced. In some cases, a surface is a surface of a sensor. In some cases, each sensor may be associated with a clonal population of template nucleic acid molecules. There can be any suitable number of sensors, including about 50 sensors, about 100 sensors, about 500 sensors, about 1000 sensors, about 5000 sensors, about 10000 sensors, about 50000 sensors, about 100000 sensors, about 500000 sensors, about 1000000 sensors, about 5000000 sensors, about 10000000 sensors, about 50000000 sensors, or more. In some instances, there are at least about 50 sensors, at least about 100 sensors, at least about 500 sensors, at least about 1000 sensors, at least about 5000 sensors, at least about 10000 sensors, at least about 50000 sensors, at least about 100000 sensors, at least about 500000 sensors, at least about 1000000 sensors, at least about 5000000 sensors, at least about 10000000 sensors, at least about 50000000 sensors, or more. In some cases, each of the sensors are individually addressable (i.e., capable of being individually controlled and/or providing an individual signal).

In some cases and in addition to the template nucleic acid molecule or population of template nucleic acid molecules, the polymerase used for nucleotide incorporation during sequencing is also bound to the surface or sensor such that incorporation of nucleotides occurs in closer proximity to the sensor. A polymerase may be bound to the surface or sensor covalently or non-covalently. Non-covalent binding can be achieved, for example, via binding of members of a binding pair (e.g., biotin/streptavidin). The surface or sensor can be modified with one member of the pair and the polymerase modified with the other member of the pair. Binding of the two members of the pair tethers the polymerase to the surface or sensor. Moreover, binding of the polymerase to the surface or sensor effectively tethers an elongation complex comprising the polymerase, a sequencing primer and a nucleotide to-be-incorporated in proximity to the sensor. Closer proximity of the elongation complex positions a redox mediator moiety associated with a nucleotide of the elongation complex closer to the sensor. Closer proximity of the redox mediator moiety to the sensor can improve electron transfer between the two species, resulting in more accurate and/or more sensitive signal detection during sequence. In some cases, a member of an elongation complex (e.g., polymerase) is tethered to the surface or sensor prior to the formation of the elongation complex. In some cases, a member of an elongation complex (e.g., polymerase) is tethered to the surface or sensor after the formation of the elongation complex.

A nucleotide can be associated with an elongation complex (whether tethered or free) for any suitable period. In some cases, the period available for detection is about 5 milliseconds (ms), about 10 ms, about 50 ms, about 100 ms, about 1000 ms, or about 5000 ms. Moreover, the period available for detection may vary depending upon, for example, whether a tethered polymerase/elongation complex is used, the particular template being sequenced, etc. In some cases, the period available for detection is at least about 5 milliseconds (ms), at least about 10 ms, at least about 50 ms, at least about 100 ms, at least about 1000 ms, or at least about 5000 ms. In some cases, the period available for detection is between about 10 and about 500 milliseconds (ms).

Figure 35:
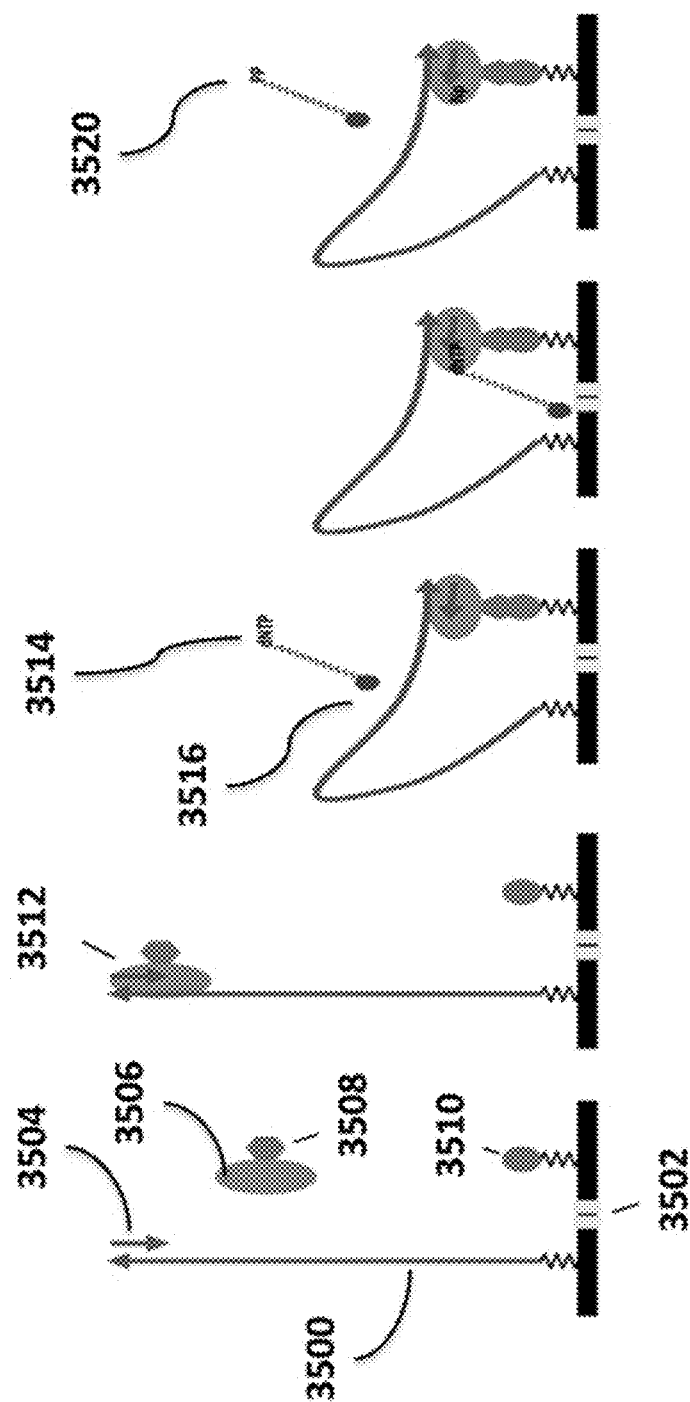
FIG. 35 schematically depicts an example method for sequencing a nucleic acid molecule using redox mediators.

An example redox-mediated sequencing method is schematically depicted in FIG. 35. With reference to FIG. 35, an immobilized template nucleic acid 3500 to be sequenced is provided on a surface associated with a sensor 3502 (e.g., a surface in proximity to the sensor 3502, a surface of the sensor 3502). For simplicity, only a single copy of the template nucleic acid 3500 is shown, however there can be a plurality of copies, including at least about 10 copies, at least about 100 copies, at least about 1000 copies, at least about 10000 copies, at least about 100000 copes, or at least about 1000000 copies. A primer 3504 is hybridized to the template nucleic acid 3500 at the distal end of the template nucleic acid 3500 relative to the sensor (as shown), at the proximal end, or any point between the distal and proximal end. The bound primer-template complex is then contacted with a polymerase that can be associated with a first member 3508 of a binding pair, such as one member of the biotin-streptavidin binding pair. The template nucleic acid 3500, polymerase 3506 and primer 3504 form an elongation complex 3512, which in some cases can include additional co-factors.

The surface is modified with a second member 3510 of the binding pair, such as the other member of the biotin-streptavidin binding pair not bound to the polymerase. Via motion of the template nucleic acid 3500 and its associated elongation complex, the polymerase 3506 binds to the second member 3510 via its first member 3508 and is positioned in proximity to the sensor 3502. Alternatively, tethering of the polymerase 3506 to the surface may be achieved with other non-covalent strategies or may be achieved covalently. Tethering of the polymerase 3506 to the surface positions the elongation complex near the sensor 3502, such that when nucleotides associated with redox mediator moieties are bound by the elongation complex, the redox mediator moieties are in close proximity and concentrated near the sensor 3502.

Following formation tethering of the elongation complex (which can result in looping of the template nucleic acid 3500 as shown in FIG. 35), the template nucleic acid molecule and associated elongation complex can be contacted with separate, sequential solutions comprising a particular type of nucleotide 3514 associated with a redox mediator moiety 3516. With each solution, nucleotides bind where appropriate, and after washing to remove unbound nucleotides, any nucleotide incorporation can be measured by the sensor 3502 and the process repeated with the next nucleotide solution. The cycle repeats until the template nucleic acid 3500 is sequenced. As shown in the example of FIG. 35 nucleotide 3514 (e.g., in the form of nucleoside triphosphates (dNTP's)) is coupled with redox mediator moiety 3516 via a linker. In some cases, the redox mediator moiety 3516 is attached to the terminal phosphate of the nucleotide 3514 and is released upon incorporation of the nucleotide 3514 as it is incorporated. The redox mediator moiety 3516 then diffuses away from the sensor 3502 once released 3520.

EXAMPLES

Example 1. The Preparation of Oil Phase for W/O Emulsification

The emulsion may be prepared using a prepared oil phase in water. The oil phase used for preparing the W/O emulsions can be prepared by mixing 4.007 g (12.2 wt %) of light mineral oil from Sigma-Aldrich, 4.802 g (14.6 wt % of ABIL WE09 from Evonik, and 24.0 g (73.2 wt %) of Tegosoft DEC from Evonik.

Example 2. The Preparation of W/O Emulsion

W/O emulsions can be prepared with the following two-step process. First a micro emulsion is prepared. 1 ml of the oil phase described in 'Example 1' is pipetted into a 2 milliliter (mL) polypropylene screw cap tube. 100 microliter (µL) of TE, pH8 (10 mM Tris (adjusted to the specified pH with HCl) and 1 mM EDTA) is added to the same tube and emulsified using a Mini-BeadBeater at 1680 oscillations/minute for 1 minute. In a second step the so-called macro emulsion is prepared. 300 µL of TE, pH 8 is pipetted to the previously generated micro emulsion and emulsification is performed using the following Mini-BeadBeater settings: 1000 oscillations/minute for 30 seconds.

Example 3. Emulsification Using Obstacle Arrays

Directing the emulsion through an obstacle array may enable control of droplet size. An example of using an obstacle array for emulsification is illustrated in FIGS. 16A-16D. An obstacle array with round obstacles (40 µm diameter, 40 µm tall, offset within a row 80 µm, offset between rows is 60 µm). Microfluidic chips were produced using injection molding. A portion of the Brass mold is shown in FIG. 16A. FIG. 16B shows the injection molded polypropylene part. Effectiveness of the obstacle array is assessed. FIG. 16C show a crude emulsion was generated by four pulses of vortexing (setting 8) 300 µl of aqueous phase (15 mM Tris buffer pH8, 60 mM Potassium Acetate, 3.3% PEG 3500) and 700 µl of oil/surfactant mixture (73.2% Tegosoft DEC, 14.6% ABIL WE09, 12.2% light mineral oil). Formation of large emulsion droplets, very heterogeneous in size was verified by light microscopy. FIG. 16D shows the crude emulsion after processing through the obstacle array. The pressure to direct the crude emulsion through the obstacle array was 40 pounds per square inch (PSI) of pressure. Performance of the obstacle array is measure by light microscopy.

Example 4. Screening of Organic Solvents to Break/Crash a W/O Emulsion

The emulsion may be disrupted through the use of a disrupting agent. As shown in Table 1, various water-miscible organic solvents are screened to break/crash the W/O emulsion in order to obtain a clear solution from which the magnetic beads can be separated and washed with an aqueous medium. In order to obtain a homogeneous clear solution, the solution was heated at 50° C. The addition Tween-20 in the "Breaking/Crashing" solvent, especially the triethylene glycol, can eliminate the heating and result in a homogeneous clear solution immediately after mixing, as shown in Table 2. An additional advantage of using triethylene glycol is its low vapor pressure and its odorless and non-toxic characteristics.

TABLE 1

Screening of water miscible organic solvents in which the oil phase is miscible.

| Breaking solvent | bp (° C.) | Vapor pressure (mmHg/20 C) | Breaking solvent (µL) | W/O Emulsion (µL) | Immediate after mixing |
|---|---|---|---|---|---|
| 2-Butanol | 98 | 12.5 | 100 | 100 | Cloudy |
| Ethylene glycol | 198 | 0.08 | 200 | 100 | Cloudy |
| Ethylene glycol monobutyl ether | 172 | 1.0 | 200 | 100 | V. slightly cloudy |
| Ethylene glycol mono-t-butyl ether | 151 | 4.7 | 200 | 100 | Slightly cloudy |
| Diethylene glycol monobutyl ether | 231 | 30.0 | 200 | 100 | V. slightly cloudy solution |
| Propylene glycol | 187 | 0.08 | 200 | 100 | V. cloudy |
| Triethlene glycol | 127 | 0.01 | 200 | 100 | Clear major bottom layer |
| Dimethyl formamide | 153 | 2.7 | 200 | 100 | Cloudy |
| Dimethyl acetamide | 166 | 2.0 | 200 | 100 | Cloudy |
| Dimethyl sulfoxide | 189 | 0.42 | 200 | 100 | Cloudy |
| N-methyl pyrrolidone | 202 | 0.29 | 200 | 100 | Slightly cloudy solution |

TABLE 2

The effect of Tween-20 to break/crash a W/O emulsion.

| Breaking solvent | Breaking solvent (µL) | Tween-20 (µL) | W/O Emulsion (µL) | Consistency immediately after mixing |
|---|---|---|---|---|
| Triethylene glycol | 200 | 13 | 100 | Clear solution |
| Ethylene glycol monobutyl ether | 200 | 13 | 100 | V. slightly cloudy solution |
| N-methyl pyrrolidone | 200 | 13 | 100 | Slightly cloudy solution |
| Diethylene glycol monobutyl ether | 200 | 13 | 100 | Slightly cloudy solution |

Example 5. The Preparation of Tetrabutylammonium Dodecylsulfate (TBADS)

One disrupting agent is tetrabutylammonium (TBADS). To prepare TBADS, 13.1 g (~13.0 mL or 1.7 meq×13=22 meq) of Dowex 50WX8 Hydrogen form is packed into a chromatographic column (1.3 cm ID and 20 cm in length). The column is rinsed with ~50 mL of DI water until pH of the eluent reaches pH 5.5 (initial pH≤4). Sodium dodecyl sulfate (SDS) is dissolve in deionized (DI) water at a ratio of 2.0227 g (7.0 milliequivalents, i.e., 7.01 millimole (mm)) of SDS to 5 milliliters (mL) of DI water. The SDS solution is tranfered into the column and eluted with 50 mL of DI water. The final pH of eluent is 5.5 and the pH of the combined eluent is 2.5. To the Dodecyl sulfuric acid eluent, 45% tetrabutylammonium hydroxide is added dropwise until pH reaching to 7 (~4.3 mL). The reaction solution is condensed by a spin-yap and subsequently freeze-dried to give 3.0 g (5.9 mmol, 84% yield) of viscous transparent oil at ambient temperature

Example 6. The Use of Triethyleneglycol/TBADS to Break W/O Emulsions

The conventional method to break a W/O emulsion and deactivate the enzymes uses four steps. It is desirable to combine the four steps into a single step process. Because SDS is insoluble in non-aqueous solvents, it may be useful to convert it into tetrabutylammonium salt (TBADS). TBADS is miscible in triethylene glycol and the oil phase (see Example 4). The TBADS breaking/crashing medium is prepared by mixing triethylene glycol, Tween-20 and TBADS as illustrated in Table 3. Entries 3 and 4 in Table 3 give homogeneous clear solutions immediately after vortexing for 5 sec.

TABLE 3

The use of a new TBADS breaking/crashing medium to break W/O emulsions.

| | Triethylene glycol (μL) | Tween-20 (μL) | TBADS (μL) | W/O emulsion (μL) | Immediately after mixing |
|---|---|---|---|---|---|
| 1 | 200 | 13 | 5 | 100 | Cloudy |
| 2 | 200 | 13 | 5 | 200 | Cloudy |
| 3 | 200 | 13 | 10 | 100 | Clear solution |
| 4 | 200 | 13 | 10 | 200 | Clear solution |
| 5 | 200 | 13 | 0 | 100 | Cloudy |
| 6 | 200 | 13 | 0 | 200 | Cloudy |

Example 7. Validation—Testing of the Amplified Magnetic Beads Obtained from the Crashed W/O Emulsion A TBADS-containing emulsion breaking medium can be prepared according to Table 4. Emulsification and confined Recombinase Polymerase Amplification on magnetic beads can be performed by formation of a micro emulsion, assembling of the amplification reaction, formation of the macro emulsion creating confined amplification reaction droplets, amplification and incubation of the emulsion, centrifugation of the emulsion containing the amplified beads, and removal of the supernatant (clear oil phase). Breaking of the emulsion is performed according the conventional method using 2-Butanol as a benchmark and with the TBADS-containing emulsion breaking medium. A 400 μl aliquot of TBADS-containing emulsion breaking medium is added to the emulsion/bead mixture. After vortexing for ~30 s, the mixture is diluted by adding 600 μL of tris ethylenediaminetetraacetic acid (TE) buffer, pH 8. After an additional vortexing step and a brief spin in a table top micro centrifuge, the beads are collected using a magnet. A magnetic bead pellet will eventually form at the side wall of the screw cap tube. At this point the entire supernatant is removed and discard. The beads are washed with 1 mL TET (10 mM Tris (adjusted to the specified pH 8 with hydrochloric acid), 1 mM ethylenediaminetetraacetic acid (EDTA), and 0.05% Triton X-100). Bead purity and workflow performance is assessed using the Flow Cytometer assays. Based on the flow cytometer data (Table 5) breaking emulsion with TBADS-containing medium does not alter performance when compared the benchmark 2-butanol breaking procedure.

TABLE 4

TBADS-containing emulsion breaking medium.

| | Vol (mL) | v/v % |
|---|---|---|
| Triethylene Glycol | 10.00 | 89.7% |
| Tween-20 | 0.65 | 5.8% |
| TABDS | 0.50 | 4.5% |

TABLE 5

Validation of the TBADS-containing emulsion breaking medium.

| Bead, Library, workflow step | Protocol used | P1 Events/μL | % single | % amplified | Mean F1 ampl | CV F1 ampl | % max amplified | Mean F1 max ampl | Cv F1 max ampl |
|---|---|---|---|---|---|---|---|---|---|
| PMK26-63, PhiX-60i, amplification | 2-Butanol | 769 | 91% | 21% | 7,608.16 | 32.08% | 17.88% | 8,332.08 | 18% |
| PMK26-63, PhiX-60i, amplification | 2-Butanol | 667 | 94% | 19% | 7,446.40 | 34.42% | 15.65% | 8,334.98 | 20% |
| PMK26-63, PhiX-60i, amplification | TBADS | 625 | 90% | 22% | 7,259.34 | 34.55% | 17.93% | 8,111.31 | 19% |
| PMK26-92, PhiX-60i, amplification | 2-Butanol | 625 | 96% | 18% | 8,395.48 | 34.33% | 15.06% | 9,229.57 | 19% |
| PMK26-92, PhiX-60i, amplification | 2-Butanol | 556 | 97% | 16% | 8,447.45 | 32.19% | 14.09% | 9,257.26 | 18% |

TABLE 5-continued

Validation of the TBADS-containing emulsion breaking medium.

| Bead, Library, workflow step | Protocol used | P1 Events/μL | % single | % amplified | Mean F1 ampl | CV F1 ampl | % max amplified | Mean F1 max ampl | Cv F1 max ampl |
|---|---|---|---|---|---|---|---|---|---|
| PMK26-92, PhiX-60i, amplification | TBADS | 400 | 92% | 19% | 8,496.69 | 31.93% | 16.28% | 9,238.96 | 18% |
| PMK26-63, PhiX-60i, enrichment | 2-Butanol | 769 | 93% | 92% | 7,046.24 | 29.82% | 75.36% | 7,723.93 | 17% |
| PMK26-63, PhiX-60i, enrichment | 2-Butanol | 588 | 93% | 93% | 7,110.26 | 29.32% | 77.45% | 7,735.86 | 18% |
| PMK26-63, PhiX-60i, enrichment | TBADS | 455 | 92% | 93% | 6,950.07 | 29.51% | 75.70% | 7,591.50 | 17% |
| PMK26-92, PhiX-60i, enrichment | 2-Butanol | 526 | 96% | 90% | 8,088.79 | 26.38% | 80.56% | 8,563.23 | 17% |
| PMK26-92, PhiX-60i, enrichment | 2-Butanol | 455 | 97% | 96% | 8,038.04 | 26.09% | 85.20% | 8,504.85 | 17% |
| PMK26-92, PhiX-60i, enrichment | TBADS | 588 | 94% | 92% | 8,046.14 | 28.63% | 82.45% | 8,534.02 | 17% |

Example 8: Preparation of a Fifteen Base Primer Conjugated Support

Preparation of a fifteen base primer conjugated support is performed inside an assembled chamber comprising an outlet and an inlet port. The support is initially cleaned by rinsing with an excess of deionized (DI) water, methanol, and isopropanol injected from a wash bottle. After rinsing, the support is soaked in an aliquot of 0.3 M sodium hydroxide (NaOH) dissolved in isopropanol for 30 minutes on an orbital shaker at ambient temperature. The NaOH-isopropanol solution is removed and a fresh aliquot of 0.3 M NaOH in isopropanol is introduced and incubated on an orbital shaker for additional 30 minutes at ambient temperature followed by rinsing with an excess of DI water, isopropanol, and blow-dried with nitrogen. The support is silylated by incubating with a solution comprising an aliquot of 2% solution of 3-aminoproptldimethylethoxysilane in anhydrous acetonitrile on an orbital shaker for 30 minutes at ambient temperature. After removal of the silane solution, a fresh aliquot is introduced and incubated for additional 30 minutes, followed by rinsing with acetonitrile and blow-dried with nitrogen. The support is heated on a 60° C. hot plate for two minutes. Polymer grafting is performed by incubating the silylated support with a solution comprising an aliquot of 0.5% w/v solution of 1:1 (or 4:1) mole ratio of poly(dimethylacrylamide-co-pentafluorophenylacrylate) in acetonitrile containing 0.5% w/v of tributylamine on an orbital shaker for 60 minutes at ambient temperature. Following polymer grafting, the support is rinsed with acetonitrile and DI water. Primer conjugation is performed by incubating the polymer grafted support with a solution comprising an aliquot of 15% w/v sodium salt of the fifteen base primer and 1.5% w/v of triethylamine in DI water on an orbital shaker at ambient temperature for 18 hours. Following conjugation, the support is rinsed with Tris-EDTA-Triton (TET) buffer (Tris-EDTA (TE) buffer containing 0.1% Triton X-100), TE buffer, and annealing buffer. The support is stored with storage buffer (1× TE buffer containing 0.05% Triton X-100 and 0.01% sodium azide) at 4° C.

Example 9: Hybridization-Dehybridization (Hyb-DeHyb) Assay Determination of Primer Loading Primer loading is determined using a Hyb-DeHyb assay. The assay is performed by first washing the support, which is located inside a chamber comprising an outlet and an inlet port, is with 2×150 μL of Annealing Buffer and blow-dried with nitrogen. Following washing, the support is incubated with a 20 μL aliquot of 5 mM of FAM Anti-B at 70° C. for 2 minutes prior to cooling the sample to ambient temperature in the dark for 2 minutes. The residual FAM Anti-B solution is removed and the support is rinsed with 2×100 μL TET buffer (10 mM TE buffer plus 0.1% Triton X-100, pH 8) followed by rinsing with 2×100 μL of 10 mM TE buffer, pH 8. Residual buffer is removed and the outlet port of the chamber is plugged with a 200 μL pipette tip. Using a 200 μL pipette tip, an aliquot of 10 μL of freshly prepared 100 mM of sodium hydroxide is dispensed into the chamber through the inlet of the chamber, ensuring that the chamber is free of air bubbles and the inlet remains plugged with the pipette tip. The support is incubated for 1.5 minutes and the 100 mM NaOH solution is retrieved through the inlet port and dispensed into 30 μL of 0.3 M aqueous solution of 3-(N-morpholino) propanesulfonic acid (MOPS). Injection of 10 μL of 100 mM NaOH is repeated three more times and for each time the 100 mM NaOH rinse is dispensed into the same 30 μL of 0.3 M MOPS solution, resulting in a mixture of four 10 μL aliquots of 100 mM NaOH rinses and one 30 μL aliquot of 0.3 M of MOPS. To this mixture, 130 μL of 10 mM TE buffer is added, resulting in a total volume of 200 μL. The sample is run in QuBit AF488 and the Green relative fluorescence unit (RFU) number is read. Using a previously established calibration, the amount of fifteen base primer can be determined. The chamber is rinsed with 10 mM TE buffer to ensure residual NaOH has been removed.

Example 10: FAM-PicoGreen Visualization of Polymer/Primer Coating

A polymer/primer coating may be visualized using FAM-PicoGreen. Visualization may be performed by first hybridizing FAM Anti-B onto the fifteen base primers according to the protocol described in Example 10. The chamber is then rinsed with TET buffer. Following rinsing, 4 μL of PicoGreen solution (100× dilution in TE of original PicoGreen reagent) is injected into the chamber 3 times with 2 minutes of incubation in the dark. The chamber is then flooded with 400 μL of loading buffer and a fluorescent micrograph is taken. Following imaging, the chamber is rinsed and the TET buffer is removed with a pipette. Following removal of the loading buffer, the chamber is soaked with a 50 μL aliquot of 100 mM NaOH solution for 2 minutes, rinsed with an excess of TET buffer, flooded with storage buffer, and stored in a water vapor saturated container at 4° C.

Example 11: Fluorescent Micrographs from FAM-PicoGreen Visualization

Fluorescent micrographs from FAM-PicoGreen visualization may be used to determine primer loading density. An example fluorescent micrograph is shown in FIGS. 31A and 31B which shows a FAM-PicoGreen fluorescent micrograph of a support surface-modified according to the procedure outlined in Example 9 and having 0.5% w/v of polymer for coupling prior to conjugation with the fifteen base primer. PicoGreen intercalator is applied to the FAM-Anti-B hybridized primer and imaged using a epifluorescence microscope and a filter cube corresponding to green fluorescence. Imaging is followed by the hybridization-dehybridization (Hyb-DeHyb) assay to determine primer loading density on the surface. FIG. 31A and FIG. 31V show that the primer conjugation chemistry is relatively stable under alkaline conditions. Rinsing the primer conjugated support with 1.0 M NaOH solution results in no significant change in primer density, which decreases form 2.69E+05 to 2.05E+05 primer molecules/$\mu^2$ after rinsing.

Example 12: Preparation of a Reactive Copolymer of N,N-Dimethylacrylamide (DMA) and Pentafluorophenylacrylate (PFPA)

Reactive copolymers of N,N-dimethylacrylamide (DMA) and pentafluorophenylacrylate (PFPA) may be prepared in various molar ratios and the following procedure is applicable for the preparation of a variety of molar ratios of the reactive copolymer. The reactive copolymer works as a linker attaching the biomolecule (e.g., DNA primer) covalently onto the amino-silylated surface of a support through amide bond formation. The polymerization vessel comprises a three-necked 500-mL round bottom flask equipped with a 2" TEFLON stir blade, a 24/40 to 14/20 ground glass adapter, a 14/20 water-cool condenser, rubber septum for 14/20 and 24/40 joints, one 12" 18-gauge SS syringe needle for nitrogen purging, and one 2" 18-gauge SS syringe needle for venting into a mineral oil bubbler. The polymerization flask is charged with an aliquot of 30 mL of anhydrous acetonitrile, 4.34 g (43.77 millimoles) of N,N-dimethylacrylamide (DMA), 10.41 g (43.73 mmol) of pentafluorophenylacrylate (PFPA), and 0.010 g (0.040 mmol) of Vazo-52. The reaction mixture is purged at ambient temperature by gentle bubbling of ultrapure nitrogen at ~60 mL/min for 30 minutes with constant stirring at 125 rpm. The reaction flask is then immersed into an oil bath at 55° C. for 19 hours with ultrapure nitrogen bubbling at a flow rate of ~15-20 mL/min and constant stirring at 120 rpm. At the end of 19 hours, the reaction mixture is highly viscous. The solvent is removed with a Rota-Evaporator at a 60° C. water bath temperature for 60 minutes to give a solid mass of polymer. The polymer product is re-dissolved in 30 mL of anhydrous tetrahydrofuran (THF). With constant stirring, 20 mL of n-hexane is added dropwise, turning the solution milky. The polymer in the THF/hexane mixture is added in a fine stream to 1000 mL of n-hexane in a 2 L glass Erlenmeyer flask under a nitrogen blanket while stirring vigorously with a 2" TEFLON stirring blade on a TEFLON stirring shaft. After precipitation, the polymer is stirred for an additional 10 minutes under a nitrogen blanket, and the supernatant is discarded. To the precipitated polymer, 500 mL of fresh n-hexane is added, and stirred gently for 10 minutes. The precipitated polymer is redissolved in 30 mL of THF followed by a second precipitation from n-hexane and washed with an excess of n-hexane. The polymer is then transferred into a large mouth 500 mL glass bottle and dried under vacuum at 60° C. for 24 hours to give 9.90 g of poly(DMA-co-PFPA) with a 82.5% yield.

Example 13: On Support Amplification

An amplification reaction may be performed on the support by first washing the support with strip buffer, followed by wash buffer, followed by annealing buffer. The seeding template is injected with a given concentration in annealing buffer, see FIG. 26C. The template is annealed by incubating the support for 10 min at 70° C., followed by cooling to room temperature in ambient air. Following annealing, the support is washed with high salt buffer. After washing, the amplification mixture, which includes the invader amplification protein mixture, 0.5 µM A15 solution primer, 1.6 µM Invader IB, and 1 mM dNTP, is injected into the support chamber and incubated at 42° C. for 30 min. After amplificaiton, the support is extensivily washed, the complement DNA strand is stripped, and the support is tested for template loading. The strip buffer comprises 100 mM NaOH, 0.05% Triton X-100. The wash buffer comprises TE pH8.0, 0.05% Trition X-100. The annealing buffer comprises TE pH8, 100 mM NaCl, 0.05% Trition X-100. The high salt Buffer comprises TE pH8, 500 mM sodium chloride (NaCl), 0.05% Trition X-100.

Example 14: Sequencing Primer Annealing to Nucleic Acid Template and Polymerase Binding Prior to sequencing, the sequencing primer can to be annealed to the nucleic acid template followed by polymerase binding. To anneal the sequencing primer, the support is first treated with 100 mM NaOH in order to remove any complementary bound strands present following amplification. This is done by treating the support with 5 µL of freshly prepared 100 mM NaOH twice for 2 mins each followed by washing with 0.3 M MOPS solution and then washing with TE buffer. The support is then washed twice with 100 µL of annealing buffer. The sequencing primer solution comprises a final concentration of 15 µM sequencing primer in annealing buffer. For each support, 12 µL of sequencing primer solution is prepared. The support is first washed with 4 µL of sequencing primer solution, followed by covering the support surface with tape that does not leave adhesive residue, to prevent evaporation, and incubating at 50° C. The total incubation time is 20 mins at 50° C. and 4 µL of sequencing primer solution is introduced at 0 mins, 7.5 mins, and 15 mins, alternating the introduction of the solution between the inlet and outlet of the chamber. In an alternate protocol for sequencing primer binding, a 20 µL solution of 15 micromolar (µM) sequencing primer is introduced into the chip inlet using a 200 µL pipette tip while a 200 µL pipette tip is present at the outlet. The chip is incubated at 70° C. for 10 min followed by cooling to room temperature using air cooling. Following 20 mins of sequencing primer annealing, the support is washed with 100 µL of TE buffer 3 times to remove any unbound primer. The support is then washed twice with 20 µL of 1× isothermal amplification buffer (ISO), once each from the inlet port and the outlet port. Polymerase incubation is performed with a final Bst2 concentration of 36 units/µL in 1×ISO solution, starting from a 120,000 units/mL original stock Bst2 solution. 12 μL of the Polymerase solution is used per support and the Polymerase solution is introduced at 0 mins, 7.5 mins and 15 mins alternating between the inlet port and outlet, for a total incubation time of 20 mins.

Example 15: Sequencing and Run-Off Experiments

Sequencing can be performed on supports to read the nucleic acid sequence of interest or to detect the amplification of a nucleic acid template of interest. The simplest way to detect for amplification of a template is to perform a 'Run-Off' experiment where a single nucleotide bottle is prepared such that it contains 100 μM of each dNTP, i.e. 400 μM total dNTP in a salt buffer B1 (3 mM magnesium chloride ($MgCl_2$), 3 mM tris(hydroxymethyl)aminomethane (TRIS) pH 8, 0.01% Triton). Electronic impedance measurements are made prior to the introduction of the nucleotides and after introduction of nucleotides. The observed impedance change corresponds to the incorporation of nucleotides and extension of the sequencing primer. Similarly, sequencing can be performed by individual introduction of nucleotides, 100 μM each, in different bottles and measurement of impedance before and after introduction of the nucleotide. In some examples, the concentration of nucleotides is less than or greater than 100 μM. Sufficiently large changes in impedance signal correspond to incorporation of a specific nucleotide at a specific sensor location.

Example 16: Sensor Electrical Measurement of Primer Adhesion

In addition to Hyb-DeHyb and PicoGreen visualization, primer conjugation may be verified by electrical measurement before and after primer addition. Polymer addition, primer addition, and biological reactions modify the electrical properties of the medium around the sensors and result in a measureable signal.

Example 17: Surface Activation of Support Surface by Acryloxysilylation

To facilitate coupling of the polymeric material to the support, the support surface may be activate with acryloxysilylation. Activation is performed by sonicating a glass support with surface-digitized gold electrodes in a 0.1% Triton X-100 solution for 15 minutes. The support is then rinsed with DI water and dried at 110° C. The cleaned slide is sonicated in RCA1/RCA2 for 15 minutes, rinsed with an excess of DI water, and stored under DI water until use. The support is dried at 110° C. for 5 minutes prior to use. To 50 mL of 95% ethanol (EtOH), 16.6 μL of 1.0 M acetic acid (AcOH) is added. The pH is 4.5-5.0. To the acidified EtOH, 1.25 mL of 3-acryloxypropyl trimethoxysilane is added and mixed by rotation at ambient temperature for 2 minutes. The pre-treated support is immersed into the silylation agent for 10 minutes with occasional agitation. The support is removed, rinsed with 95% ethanol briefly, and blow-dried with nitrogen. The support is annealed at 110° C. for 2 minutes. In some embodiments, the 3-acryloxypropyl trimethoxysilane may be replaced by 3-acryloxypropyl dimethylethoxysilane. This technique may be applicable to silicon and glass substrates with or without digitized electrodes.

Example 18: Fluorosilylation of Glass Coverlid to be Used as a Release

A fluorosilylated glass coverlid may be used during polymerization to prevent the polymer product from adhering to the coverlid. Fluorosilylation is performed by pretreatment of a glass coverlid as described in Example 18. Following pretreatment, a solution of 1.25 mL of (Heptadecafluoro-1,1,2,2-tetrahydrodecyl)trimethoxysilane in 50 mL of 95% ethanol is prepared in a polypropylene 50-mL Falcon tube. The pH of the solution is adjusted by adding 16.6 μL, of 1.0 M AcOH and mixed by rotation for 2 minutes. The pre-treated glass coverlid is immersed into the silylation solution for 10 minutes with occasional agitation. The glass coverlid is removed, rinsed with 95% ethanol briefly, and dried with nitrogen. The Fluorosilylated glass coverlid is cured at 110° C. for 10 minutes.

Example 19: Pre-Polymer Solution and Polymerization of Porous Polymer Monoliths (PPM)

Polymerization of the porous polymer monolith (PPM) is performed using a pre-polymer solution. The pre-polymer solution comprises 1995 mg of pentafluorophenyl acrylate, 365 mg of divinylbenzene, 19.7 mg of benzophenone, and 19.3 mg of Ethyl 4-(dimethylamino)benzoate. This pre-polymer solution is mixed with pentadecane porogen in 1:1 v/v ratio prior to dispensing onto the acryloxysilane activated substrate surface, prepared in Example 18. The fluorinated cover slide, prepared in Example 19, is placed with the fluorinated surface down onto the pre-polymer to form a thin layer. The assembly is exposed to ultraviolet (UV) light for polymerization. After polymerization, the fluorinated cover slip is removed and the PPM thin film is washed with an excess of pentadecane and blow-dried with nitrogen.

Example 20: Polymerization of BRAPA Containing Hydrogels and Primer Conjugation

Polymerization of the BRAPA containing hydrogel is performed by first washing the support with methanol, followed by 1 N NaOH, and DI water last. Following washing, the support is dried with nitrogen and placed within a chamber. A solution of 3.3 w/w % acrylamide, 0.33 w/w % BRAPA, 0.1 w/w % ammonium persulfate, and 0.23 w/w % tetramethylethylenediamine is injected into the chamber and incubated at ambient temperature for 90 minutes. The support is then washed with water and incubated at ambient temperature with a freshly reduced dimethyl sulfoxide solution of thiobenzoated primer. After conjugation, the support is washed with water and incubated with a quenching solution, such as a potassium acetate solution.

Example 21: Thin Layer Cell for Hyb-DeHyb Assay

The Hyb-DeHyb assay is performed in a thin layer cell. FIG. 32 shows the construction of a thin-layer cell for Hyb-DeHyb assay to measure the amount of HP1 hybridized onto the PPM-bonded DNA primer. The flow cell is fabricated using a silicon gasket (BioRad Frame-Seal Incubation Chambers, 265 μL volume, 1.5 mm×17 mm×28 mm). Three rectangular gaskets are placed on top of each other in between a microscope slide and a flexible plastic coverslip. The addition of reagents for a Hyb-Dehyb assay and retrieval of de-hybridization products are performed using syringes and 27-gauge stainless steel syringe needles through the 1.5 mm thick gasket.

Example 22: Detection of Surface Hybridized HP1 Oligo on PPM

Figure 33:
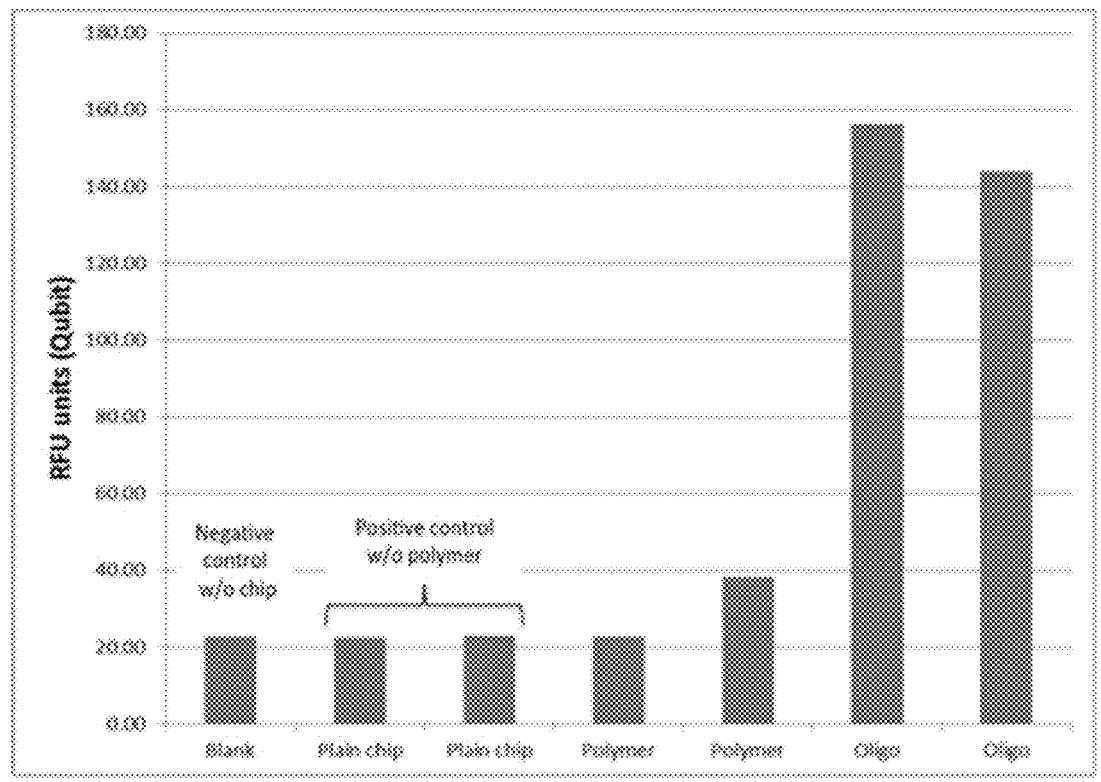
FIG. 33 shows detection of primer oligos surface conjugated to the PPM thin film.

The amount of surface conjugated oligo may be detected using a Hyb-Dehyb assay. FIG. 33 shows the results of Hyb-DeHyb assay to measure the amount of HP1 oligo hybridized onto the PPM thin film by QuBit. A thin-layer cell with a glass support, PPM polymer thin film, and surface hybridized DNA template oligo are annealed with an 'HP1' template-specific fluorescent FAM probe. 100 µL of 2 uM FAM probe in annealing buffer is annealed to the oligo template, using an annealing protocol involving increasing the temperature to 95° C., followed by slowly ramping down to 25° C. The thin-layer cell is then washed three times with TE buffer to remove non-specifically bound probe, followed by washing with water. Finally, the bound probe is extracted by incubation with 100 mM NaOH, over 2 incubations of ~12.5 µL for 2 min each. The eluted solution is neutralized with 15 µL of 0.3 M MOPS solution, followed by addition of 160 µL of TE buffer. The fluorescence values were measured using a Qubit reader. The plain support and polymer-only support show fluorescence levels comparable to background, while the 'HP1' oligo supports show a high fluorescence indicating specific template hybridization.

Example 23: Redox-Mediated Sequencing

An example system used for redox-mediated nucleic acid sequencing is described below. The system includes nanogap electrodes and one of the four nucleotide triphosphates (A, G, T, or C) carrying one or more redox mediator moieties on their gamma phosphates. The one or more redox mediator moieties are linked to gamma phosphates by 10 nm linkers. Sequencing (e.g., sequencing-by-synthesis) is performed as described herein by cycling through the four nucleotide triphosphates for incorporation to template nucleic acids via the action of a polymerase. Cognate nucleotide triphosphates are bound by initiation complexes for 10-500 milliseconds (ms) before cleavage of the alpha-beta phosphate bond (and incorporation of the nucleotide monophosphate). During this time, redox mediator moieties diffuse to the nanogap electrodes multiple times (e.g., about 1,000 times if diffusion time is 20 nanoseconds (nsec)) resulting in 1,000 oxidation-reduction cycles and transfer of 1,000 electrons per mediator (e.g., 1,000λ amplification by redox cycling). Each colony of template nucleic acid molecules contains 10,000 template strands with a total number of electrons transferred approximately 10 million or about 1.7 picocoulombs (pC). Electron transfer occurs over a 20 ms period and the magnitude of the generated current pulse is 83 picoamperes (pA. The current pulse can scale with number of redox mediator moieties. For example, if nucleotide triphosphates carry 10 redox mediator moieties, then the generated current pulse is 830 pA. After triphosphate cleavage, pyrophosphate (carrying redox mediator moieties) diffuses away from the surface thereby terminating signal generation.

Devices, methods and systems of the present disclosure can be combined with or modified by other devices, systems and/or methods, such as, for example, those described in PCT Patent Application No. PCT/US2011/054769, PCT Patent Application No. PCT/US2012/039880, PCT Patent Application No. PCT/US2012/067645, PCT Patent Application No. PCT/US2014/027544, PCT Patent Application No. PCT/US2015/020130, PCT Patent Application No. PCT/US2015/026135, and U.S. Pat. No. 9,399,217, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for sequencing a nucleic acid template, comprising:
    (a) contacting a nucleic acid template with a sensing fluid containing a population of nucleotides, wherein said nucleic acid template is hybridized to a primer that is coupled to a bead, which bead is positioned proximate to a sensor in a sensor array, wherein said sensor comprises at least two electrodes, wherein said sensing fluid has a sensing fluid bulk conductivity and a surface of said bead has a surface conductivity to provide a Dukhin number that is less than 1 such that (i) a conductivity measurement by said at least two electrodes with said bead positioned proximate to said sensor is substantially similar to (ii) another conductivity measurement by said at least two electrodes without said bead positioned proximate to said sensor;
    (b) using said at least two electrodes of said sensor to detect a conductivity change within a Debye layer of said bead upon incorporation of at least one nucleotide of said population of nucleotides into a growing nucleic acid strand, which growing nucleic acid strand is derived from said primer and is complementary to said nucleic acid template, which conductivity change is detected based at least in part on an electrical current change through said Debye layer;
    (c) washing said sensor array to remove unincorporated nucleotides of said population of nucleotides from said sensor array; and
    (d) repeating (a)-(c) to obtain sequence information for said nucleic acid template.

2. The method of claim 1, wherein an electrode of said at least two electrodes is exposed to said sensing fluid.

3. The method of claim 1, wherein (b) further comprises detecting a change in impedance within said Debye layer of said bead upon incorporation of said at least one nucleotide.

4. The method of claim 3, wherein said change in impedance within said Debye layer is detected at steady state.

5. The method of claim 1, wherein said at least two electrodes are positioned within said Debye layer of said bead.

6. The method of claim 1, wherein said sensing fluid has a solute concentration between about 0.15 millimolar and about 6 millimolar.

7. The method of claim 1, further comprising, prior to (b):
    (i) contacting said sensor array with a probe fluid, wherein said probe fluid has a probe fluid bulk conductivity that is at least about 50 times greater than or at least about 50 times less than said surface conductivity of said surface of said bead; and (ii) using said sensor to detect signals that are indicative of a presence of said bead in proximity to said sensor.

8. The method of claim 7, wherein an additional Dukhin number determined from said probe fluid bulk conductivity and said surface conductivity of said surface of said bead is substantially less than 1.

9. The method of claim 7, wherein an additional Dukhin number determined from said probe fluid bulk conductivity and said surface conductivity of said surface of said bead is substantially greater than 1.

10. The method of claim 7, wherein (b), (c), and (d) are performed only at sensors of said sensor array at which signals indicative of bead occupancy are observed.

* * * * *